United States Patent [19]

McCullagh et al.

[11] Patent Number: 4,568,666

[45] Date of Patent: Feb. 4, 1986

[54] CARBOXYLALKYL PEPTIDE DERIVATIVES

[75] Inventors: Keith G. McCullagh, Princes Risborough; Harry J. Wadsworth, High Wycombe; Michael M. Hann, Watlington, all of United Kingdom

[73] Assignee: G. D. Searle & Co., Skokie, Ill.

[21] Appl. No.: 662,129

[22] Filed: Oct. 18, 1984

[51] Int. Cl.<sup>4</sup> ..................... A61K 37/00; C07C 103/52
[52] U.S. Cl. ............................... 514/20; 260/112.5 R
[58] Field of Search ................... 514/20; 260/112.5 R

[56] References Cited

U.S. PATENT DOCUMENTS 4,374,829  2/1983  Harris et al. ..................... 514/20

Primary Examiner—Delbert R. Phillips
Attorney, Agent, or Firm—Stuart L. Melton

[57] ABSTRACT

This invention encompasses novel carboxyalkyl peptide derivatives which are collagenase inhibitors.

10 Claims, No Drawings

CARBOXYLALKYL PEPTIDE DERIVATIVES

BACKGROUND OF THE INVENTION

This application is a continuation-in-part application of prior copending application Ser. No. 599307, filed Apr. 12, 1984, now U.S. Pat. No. 4,511,504.

This invention relates to novel compounds having pharmacological activity, to the production thereof, to compositions containing them, and to their use in the treatment or management of conditions or diseases, e.g., rheumatoid arthritis, in which collagenase promoted collagen breakdown is a causative factor.

We have now found a group of compounds which act as inhibitors of mammalian collagenase which initiates collagen breakdown. Extensive proteolytic enzyme promoted degradation of articular cartilage is associated with joint destruction in rheumatoid arthritis. Collagen is one of the major components of the protein matrix of joint cartilage and bone. Histological observations of rheumatoid lesions have established that such lesions are characterized by the proliferation of synovial lining cells with subsequent neovascularization and infiltration by lymphocytes, macrophages and plasma cells, collectively referred to as soft tissue or "pannus". The importance of such soft tissue in cartilage erosion has been well demonstrated.

Evanson and coworkers, for example, found that large amounts of neutral collagenase are produced by pannus tissue [Evanson, J. M., et al., Arthritis & Rheum., 27, 2639-2651, 1968]. More recently, others have confirmed that neutral collagenase plays an important degradative role in the arthritic joints of experimental animals [see Cambray, et al., Rheumatol Int. 1, 11-16 and 17-20, 1981] and in humans [Cawston, et al., Arthritis & Rheum., 27, 285-290, 1984].

A mono-specific antiserum to purified synovial collagenase has been used to localize the enzyme in rheumatoid tissues [Wooley, et al., Eur. J. Biochem., 69, 421-428, 1976]. Immunoreactive collagenase was detected in high density at the cartilage-pannus junction—the site of joint erosion—but not in the cartilage matrix or synovial tissue remote from the cartilage-pannus junction [Wooley, et al., Arthritis & Rheumatism, 20, 1231-1349.] Wooley, et al., (Science, 200, 773-775, 1978) have further identified a sub-population of synovial cells responsible for collagenase production.

Thus, the foregoing observations have provided conclusive evidence that collagenase is directly involved in the cartilage erosion process seen in rheumatoid arthritis. Accordingly, the compounds of the present invention which specifically inhibit mammalian collagenase are pharmacologically useful in the treatment of rheumatoid arthritis and related diseases in which collagenolytic activity is a contributing factor, such as corneal ulceration, peridontal disease, tumor invasion, dystrophic epidermolysis bullosa, etc.

These compounds have substantially no angiotensin converting enzyme (ACE)-inhibiting activity. ACE inhibitors are described in European Appl. No. A-0012401. ACE is a carboxydipeptidase—it cleaves a peptide substrate two residues from the C-terminus. Consequently the C-terminal carboxylic acid is a prime recognition site for both substrates and inhibitors; removal of this ionic binding group drastically reduces inhibitory potency. Collagenase, on the other hand, is an endopeptidase and, as such, has no prerequisite for this binding interaction. Additionally, the structure of collagen differs essentially from angiotensin-I which is a decapeptide and is cleaved at a phenylalanine-histidine bond to give an octapeptide (angiotensin-II) and a dipeptide (histidylleucine). Collagen is much more complex, in being a triple helix, each strand of the helix containing of the order of 1,000 amino acid residues, the sequence of amino acids around the site cleaved by collagenase being completely different from that around the cleavage site of Angiotensin I. Collagenase cleaves this triple helix at a single locus on each chain approximately two-thirds of the way along the chain from the N-terminus. The amide bond which is cleaved by collagenase is either a glycine-leucine or a glycine-isoleucine bond.

BRIEF DESCRIPTION OF THE INVENTION

The present invention provides compounds of the general formula I:

$$A^1-A^2-Y-(CH_2)_n-\underset{H}{\overset{COR^1}{C}}-NH-\underset{O}{\overset{R^2\ R^3}{\underset{\|}{C}}}-A^3 \qquad I$$

and pharmaceutically acceptable salts thereof in which $n = 1-4$ $R^1$ represents hydroxy, alkoxy, aralkoxy or hydroxyamino;

$R^2$ represents hydrogen or alkyl;

$R^3$ represents
hydrogen,
alkyl,
substituted alkyl wherein the substituent may be one or more of the groups selected from hydroxy, alkoxy, aryloxy, aralkoxy, mercapto, alkylthio, arylthio, alkylsulphinyl (e.g. $SOCH_3$), alkylsulphonyl (e.g. $SO_2CH_3$), carboxy, carboxamido (e.g. $CONH_2$), carboxyalkyl (e.g. $CO_2CH_3$), carboxyaralkyl (e.g. $CO_2CH_2Ph$), aralkoxycarbonylamino (e.g. $NHCOOCH_2Ph$), amino, dialkylamino, acylamino (e.g. $NHCOCH_3$), aroylamino (e.g. $NHCOPh$) and trihalomethyl (e.g. $CF_3$),
aralkyl,
substituted aralkyl wherein the substituent on the aryl moiety may be one or more groups selected from halogen (e.g. fluorine, chlorine, bromine, iodine), alkyl, hydroxy, alkoxy, aralkoxy, amino, aminomethyl ($CH_2NH_2$), cyano, alkylamino, dialkylamino, carboxy, sulphonamido, alkylthio, nitro and phenyl,
or heteroaralkyl;

Y represents $NR^4$ wherein $R^4$ represents H or alkyl; or for certain values of $A^1$, $A^2$ may alternatively be a direct chemical bond.

When Y represents $NR^4$,
$A^1$ represents a group of formula $R^5$ wherein
$R^5$ may be
hydrogen,
alkyl,
aralkyl,
aryl,
substituted aryl wherein the substituent may be one or more groups selected from halogen alkyl, hydroxy, alkoxy, aralkoxy, aralkoxyamino, aminomethyl, cyano, acylamino, dialkylamino, carboxy, sulphonamido, alkylthio, nitro and phenyl, acyl (e.g. CH₃CO),
aroyl (e.g. PhCO),
aralkylacyl (e.g. PhCH₂CO),
alkoxycarbonyl (e.g. (CH₃)₃OCO),
or aralkoxycarbonyl (e.g. PhCH₂OCO);

$A^1$ may also represent a group of the formula:

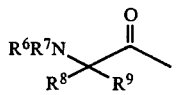

wherein
$R^6$ represents a group having the meanings defined above for $R^5$;

$R^7$ and $R^8$ which may be the same or different represent hydrogen, alkyl or aralkyl; or $R^7$ and $R^8$ may together represent an alkylene chain of 2–4 carbon atoms so to form with the adjacent nitrogen atom a nitrogen-containing ring having 4–6 atoms;

$R^9$ represents
hydrogen,
alkyl,
substituted alkyl wherein the substituent is exactly as defined for this moiety above,
aralkyl,
substituted aralkyl wherein the substituent is exactly as defined for this moiety above,
or heteroaralkyl;

$A^2$ represents a group of the formula

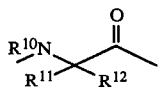

wherein
$R^{10}$ and $R^{11}$ which may be the same or different represent groups having the meanings given above for $R^7$ or together represent an alkylene chain of 2–4 carbon atoms so as to form with the adjacent nitrogen a nitrogen-containing ring having 4 to 6 atoms;

$R^{12}$ represents a group having the meanings given above for $R^9$.

Additionally, $A^1$ and $A^2$ taken together may represent
hydrogen,
alkyl,
aralkyl,
heteroaralkyl,
alkylsulphonyl,
arylsulphonyl,
aralkylsulphonyl,
or a group $R^{13}CO$ wherein $R^{13}$ represents
hydrogen,
alkyl,
alkoxy,
aryl,
aralkyl,
aralkoxy,
substituted aryl (as defined in $R^3$), substituted aralkyl (as defined in $R^3$) and substituted aralkoxy wherein the substituent on the aromatic moiety of the aralkoxy is as defined for aralkyl
phenethenyl (PhCH=CH—),
phenethynyl (PhC≡C—),
alkylamino,
arylamino,
aralkylamino,
or dialkylamino;

In a further aspect of this invention, Y may also represent a direct chemical bond. In this instance, $A^1$ and $A^2$ taken together represent
hydrogen,
alkyl,
aryl,
alkoxy,
aralkoxy,
substituted aryl (as in $R^3$) and substituted aralkoxy (as in $R^3$) wherein the substituent on the aromatic moiety of the aralkoxy is as defined for aralkyl,
hydroxy,
mercapto,
alkylthio,
arylthio,
aralkylthio,
carboxy,
or carboxyalkyl;

$A^3$ represents a group of the formula
$R^{14}$
or

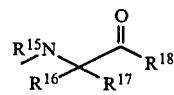

wherein
$R^{14}$ represents amino,
alkylamine,
dialkylamino,
hydroxyamino,
or aralkylamino,
and $R^{15}$, $R^{16}$ and $R^{17}$ which may be the same or different represent groups having the meaning given above for $R^{10}$, $R^{11}$ and $R^{12}$ respectively and $R^{18}$ represents
amino,
alkylamino,
dialkylamino,
substituted alkylamino wherein the substituent is amino, hydroxy, alkoxy, carboxy, carboxamido, carboxyalkyl, alkylthio, alkylsulphinyl or alkylsulphonyl,
hydroxyamino,
alkoxyamino,
aralkylamino,
alkoxy,
aralkoxy,
or alkylaminoalkoxy.

all with the exception that when $A^3$ is alkylamino one of $R^2$ and $R^3$ is not hydrogen and the other alkyl or hydroxyalkyl.

DETAILED DESCRIPTION OF THE INVENTION

The term alkyl as used herein to designate a group or a part thereof includes reference to both straight and branched alkyl groups and to cycloalkyl groups which may contain from 1 to 10, preferably 1 to 6, carbon atoms in the case of straight or branched chain non-cyclic alkyl groups (for example methyl, ethyl, propyl, isopropyl) and from 3 to 10, preferably 3 to 7 in the case of cyclic alkyl groups (for example cyclopentyl, norbornyl).

By the term aryl, is meant phenyl or naphthyl.

The terms aralkyl and aralkoxy include in particular those groups containing 1 to 4 carbon atoms in the alkyl portion, and those groups in which aryl has the meaning just given.

By the term heteroalkyl we mean in particular groups containing 1 to 4 carbon atoms in the alkyl moiety. The term heteroaryl includes for example, pyridyl, thienyl, furyl, indolyl, imidazolyl and thiazolyl.

Typical pharmaceutically acceptable addition salts are those derived from mineral and organic acids such as hydrochloric, hydrobromic, hydroiodic, p-toluene sulphonic, sulphuric, perchloric, acetic, benzoic, trifluoroacetic and the like.

There are several chiral centres in the compounds according to the invention because of the presence of asymmetric carbon atoms. These centres may be racemised or in any optically active form. We have found surprisingly that those compounds in which the chiral centre indicated below by an asterisk in the group shown is in the R form are preferred.

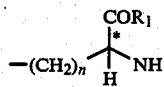

Certain groups of compounds according to the invention are preferred, these including the following. A group of preferred compounds are those in which the group $A^3$ has the following meaning

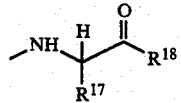

in which $R^{17}$ represents substituted alkyl (wherein the substituent is alkoxy, aralkoxy, alkoxycarbonylamino, aralkoxycarbonylamino, carboxyalkyl or carboxyaralkyl); or substituted aralkyl (wherein the aryl substituent is one or more groups selected from alkyl, alkoxy, alkyl thio or aralkoxy). In this preferred group of compounds, $R^3$ should have the meanings described hereinafter but excluding aralkyl or heteroalkyl. Within this definition of $A^3$, there is a preferred subclass of compounds in which $A^1+A^2$ taken together represent H, Y is a direct chemical bond, $R^2$ represents H, and $R^3$ represents alkyl or substituted alkyl where the substituent(s) is one or more trifluoromethyl groups. Therefore this first sub-class of preferred compounds may be defined by the formula

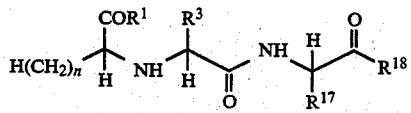

wherein $R^3$ and $R^{17}$ are as defined above. A most preferred set of compounds within this group are those in which $R^{17}$ is benzyloxymethyl (PhCH$_2$OCH$_2$—), 1-benzyloxyethyl (PhCH$_2$OCH(CH$_3$)—), 4-benzyloxyphenylmethyl (4—PhCH$_2$OC$_6$H$_4$CH$_2$—) or 4-methoxyphenylmethyl (4—CH$_3$OC$_6$H$_4$CH$_2$—).

In a second preferred sub-class of compounds within the preferred definition of $A^3$, Y represents $NR^4$, and $A^1+A^2$ represent a group $R^{13}CO$ wherein $R^{13}$ represents alkyl,
aryl,
aralkyl,
aralkoxy,
substituted aryl, substituted aralkyl and substituted aralkoxy wherein the substituent on the aromatic moiety is exactly as defined hereinbefore,
alkylamino,
arylamino,
aralkylamino
or dialkylamino.

Therefore this second sub-class of preferred compounds may be defined by the formula

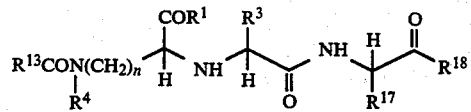

Particularly preferred examples are those in which $R^4$ is H and $R^3$, $R^{17}$ and $R^{18}$ are as defined for the first preferred sub-class of compounds. A most preferred series of compounds within this sub-class is where n is 2, $R^{13}$ is benzyloxy (PhCH$_2$O), substituted benzyloxy (where the aromatic substituent is selected from 4-chloro, 2-chloro, 4-methyl, 4-nitro or 4-amino), benzylamino (PhCH$_2$NH), phenyl or substituted phenyl (where the aromatic substituent is selected from 4-chloro, 2-chloro, 4-methyl, 4-nitro or 4-amino).

A further preferred embodiment of the invention is a compound of the formula

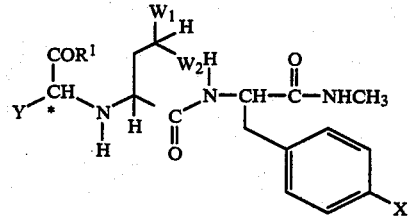

and the pharmaceutically acceptable acid addition salts thereof wherein x represents hydrogen, alkoxy or benzyloxy; y represents a radical selected from alkyl, alkylthioalkyl,

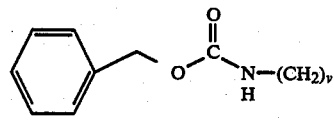

wherein v is 2 or 3,

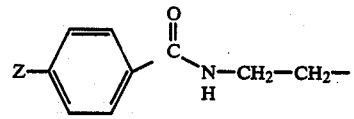

wherein z represents hydrogen or nitro; $W_1$ and $W_2$ represent methyl or trifluoromethyl; and $R^1$ represents hydroxy or alkoxy and the stereochemistry of the carbon marked by the asterisk is R.

A still further especially preferred embodiment of the invention are compounds of the formula:

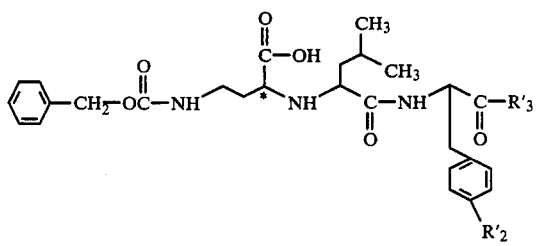

and the pharmaceutically acceptable acid addition salts thereof wherein $R'_2$ represents hydroxy, alkoxy, cycloalkoxy, aralkoxy or substituted alkoxy wherein the substituent is selected from alkylaminocarbonyl or the group

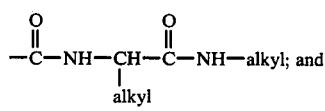

$R'_3$ represents alkylamino or aralkylamino and the stereochemistry of the carbon atom marked by the asterisk is R, S or a diastereomeric mixture thereof with R configuration being preferred.

The compounds according to the invention exhibit inhibitory action against collagenase. This was determined following the procedure of Cawston and Barrett, Anal. Biochem., 99, 340–345 (1979) whereby the 1 mM of the inhibitor being tested or dilutions thereof are incubated at 37° C. for 16 hours with native collagen and collagenase (buffered with Tris HCl—CaCl$_2$; pH 7.6). The collagen is acetyl $^{14}$C collagen. The samples are centrifuged to sediment undigested collagen and an aliquot of the radiactive supernatant removed for assay on a scintillation counter as a measure of hydrolysis. The collagenase activity in the presence of 1 mM inhibitor, or a dilution thereof, is compared to activity in a control devoid of inhibitor and the results reported as that inhibitor concentration effecting 50% inhibition of the collagenase. Table II illustrates the activity of compounds of this invention.

For use in treatment of rheumatoid arthritis the compounds of this invention can be administered by any convenient route preferably in the form of a pharmaceutical composition adapted to such route and in a dose effective for the intended treatment. In the treatment of arthritis administration may conveniently be by the oral route or by injection intraarticularly into the affected joint. The daily dosage for a 70 kilogram mammal will be in the range of 10 milligrams to 1 gram.

The compounds of this invention can be formulated in compositions such as tablets, capsules or elixirs for oral administration or in sterile solutions or suspensions for parenteral administration. About 10 to 500 mg of a compound according to the invention is compounded with a physiologically acceptable vehicle, carrier, excipient, binder, preservative, stabilizer, flavour, etc., in a unit dosage from as called for by accepted pharmaceutical practice. (See for example, Remington's Pharmaceutical Science Mach Publishing Co., Easton, Penn. 1965). The amount of active substance in these compositions or preparations is such that a suitable dosage in the range indicated is obtained.

The compounds according to the invention may be made by methods which are generally known in peptide chemistry for analogous compounds. In particular it is to be understood that reactive groups not involved in a particular reaction (e.g., amino, carboxy, hydroxy etc.,) may be protected by methods standard in peptide chemistry prior to reactions of other groups and subsequently deprotected.

The intermediates of use in the production of the end-products are either known compounds or can be made by known methods, as described in the Examples.

The following description of the preparative methods indicates generally the routes which may be used for the production of the compounds according to the invention.

PROCESS 1, ROUTE A

This process involves reductive amination

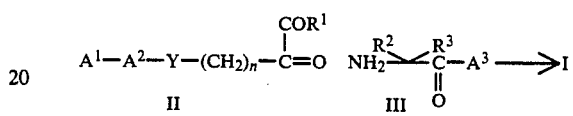

A keto acid (or derivative) of formula II is condensed with a peptide of formula III. This condensation is conveniently carried out in a suitable solvent (e.g. aqueous tetrahydrofuran, methanol) at a pH between 6 and 7 in the presence of sodium cyanoborohydride which effects reduction to give the desired compound of formula I. Alternatively, II and III may be reacted in the solvent medium to form a Schiff's Base as an intermediate and this may then be reduced catalytically to yield the desired compound of formula I for example by hydrogenation in the presence of Raney Nickel or palladium on charcoal.

As an alternative to Process 1, Route A, the compound of formula II can be condensed with an amino acid of formula IV below (or protected derivative thereof) under the same conditions as given in Process 1 to yield an intermediate of formula V. This intermediate is then subsequently coupled with an amino acid or peptide derivative of the formula $A^3$ to give the compound of formula I.

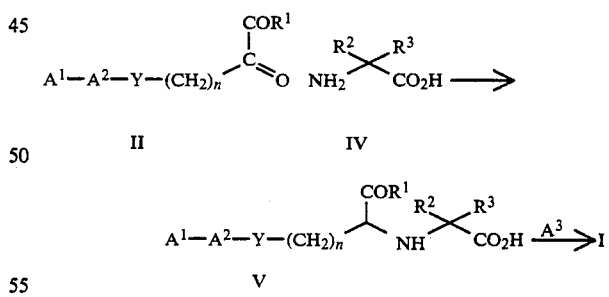

The known processes for peptide bond formation referred to above and also in the following processes encompass reactive group protection during the coupling reaction, e.g., for amines employing N-t-butyloxycarbonyl or N-benzyloxycarbonyl followed by their removal. Condensing agents are typically those useful in peptide chemistry such as dicyclohexylcarbodiimide, water soluble carbodiimide [N-ethyl-N$^1$-(3-dimethylaminopropyl)-carbodiimide], diphenyl phosphoryl azide or V may be activated via the intermediary of active esters such as those derived from 1-hydroxybenzotriazole, 4-nitro phenol, 4-picolyl alcohol.

PROCESS 1 ROUTE B (where $R^4=H$)

In an alternative reductive amination process as shown below, the starting materials providing the groups $A^1$-$A^2$ on the one hand and the group $A^3$ on the other are reversed. Otherwise the process is the same as Process 1 Route A. This process is applicable to the production of compounds in which $R^4$=H.

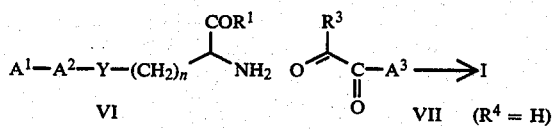

The amino acid (or derivative) VI is condensed with the ketone (VII) under the conditions given in Route A.

As an alternative to Process 1, Route B the synthesis can be performed in a step wise manner by condensing VI with the keto acid (or derivative) VIII to yield the intermediate IX. By known processes (summarised above), IX can then be condensed with an amino acid or peptide derivative $A^3$ to give I.

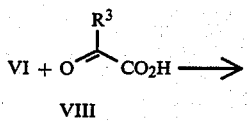

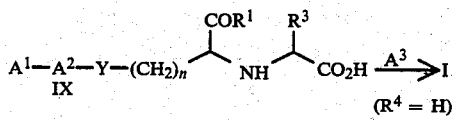

PROCESS 2 ROUTE A

This process is essentially an alkylation.

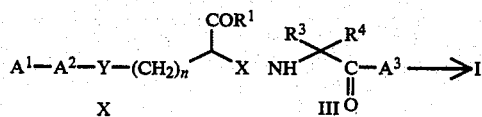

In this process the peptide III is alkylated with the appropriate α-haloacid (or derivative) X or α-sulphonyloxy acid in a suitable solvent (e.g., $CH_2Cl_2$, $CH_3CN$, etc.) in the presence of a base (e.g. triethylamine).

As an alternative to this process, the synthesis can be performed in a stepwise fashion firstly to produce an intermediate IX which is then condensed by standard processes above with a peptide derivative $A^3$ to give the compound of formula I, as described above for the alternative for Process 1, Route A.

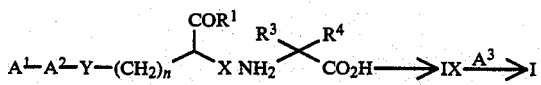

PROCESS 2 ROUTE B

In an alternative alkylation shown below the starting materials providing the groups $A^1$-$A^2$— on the one hand and $A^3$ on the other are reversed. Otherwise the method is the same as Process 2, Route A.

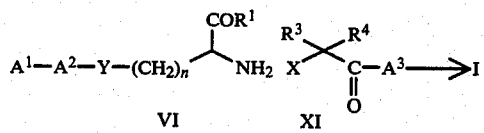

The amino acid (or derivative) VI is alkylated with the α-haloacetyl or α-sulphonyloxyacetyl peptide derivative XI under the conditions described in Route A.

As an alternative to Process 2, Route B the synthesis can be performed in a stepwise fashion by condensing an amino acid (or derivative) VI with a substituted α-haloacetic acid or α-sulphonyloxy acetic acid (XII) to yield the intermediate IX which by standard processes is condensed with a peptide derivative $A^3$ to give the compound of formula I

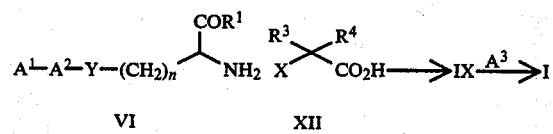

It should be noted that when $A^1$ and/or $A^2$ represent amino acid residues, that these residues may be introduced by standard coupling procedures at any convenient stage of the synthesis.

The starting materials which are required for the above processes are either known in the literature, or can be made by standard processes from known starting materials, or are described in the Examples.

When $R^1$ in I represents hydroxy, these compounds may be derived from those described above (wherein $R^1$=alkoxy or aralkoxy) by hydrolysis in a suitable solvent (such as aqueous methanol) containing a base such as sodium or lithium hydroxide. Alternatively, when $R^1$=aralkoxy (such as $PhCH_2O$), this group may be removed by hydrogenolysis.

As mentioned above there are various potentially asymmetric centres in the amide derivatives of this invention. In particular the carbon atom which bears the groups $(CH_2)_n$, $COR^1$ and NH is asymmetric as is that which bears the groups NH, $COA^3$, $R^2$ and $R^3$ (when $R^2$ and $R^3$ are not simultaneously hydrogen). The above synthesis can utilize racemates, enantiomers or diastereoisomers or starting materials, the products can therefore exist in racemic or optically active forms. The invention therefore encompasses the racemic form as well as any other optically active forms. As noted above, however, and in contrast to inhibitors of other zinc metalloproteinases (such as angiotensin converting enzyme), the preferred isomer has R-stereochemistry at the carbon atom bearing the groups $(CH_2)_n$, $COR^1$ and NH whilst having the stereochemistry of the natural amino acids at the other asymmetric centres.

The compounds according to the invention include pharmaceutically acceptable salts of the compounds of formula I. Such salts may include acid addition salts as well as amine salts, etc., and the processes described above for the production of the compounds may include as a final step the conversion of the compound I into such a salt, or the compound may be isolated as such salt.

It is understood that the compounds which bind most effectively to collagenase have $R^1$ equal to either hydroxy or hydroxyamino. When $R^1$ is alkoxy or aralkoxy, these compounds function as orally active prodrugs of the parent carboxylic acids; once absorbed these esters are rapidly hydrolysed by non specific plasma esterases to yield the active species.

In order that the invention may be more fully understood the following Examples are given by way of illustration and should not limit the invention in spirit or scope. All temperatures herein are degrees C.

EXAMPLE 1

N-(1-Methoxycarbonylethyl)-L-leucyl-L-valine N-Hexylamide

N-(Tertiarybutyloxycarbonyl)-L-leucyl-L-valine N-Hexylamide (2 g) was treated with trifluoroacetic acid (20 ml) at room temperature for forty-five minutes. The excess trifluoroacetic acid was removed in vacuo and the residue dissolved in methanol (20 ml). The solution was adjusted to pH7 with triethylamine. Dried 3 A molecular sieve (10 g), sodium cyanoborohydride (0.75 g) and methyl pyruvate (1.5 g) were added and the reaction mixture stirred at room temperature for 2 days. The reaction mixture was then filtered and the filtrate concentrated in vacuo to a gum. The residue was taken up in dichloromethane and the organic phase washed in turn with saturated sodium hydrogen carbonate solution and then 1M citric acid solution and dried over sodium sulphate. The material isolated after evaporation of the dichloromethane was chromatographed on silica, developed in a gradient of 20% ethyl acetate in hexane to 60% ethyl acetate in hexane. Elution with 40% ethyl acetate hexane afforded N[1-(S)-methoxycarbonylethyl]-L-leucyl-L-valine N-hexylamide (0.4 g), which crystallised from methanol/water as needles m.p. 70°–71° C.; $[\alpha]_D^{20} = -31.4°$ (c=0.2, MeOH); (Found: C,63.0; H,10.2; N,10.5. $C_{21}H_{41}N_3O_4$ requires C,63.1; H,10.3; N,10.5%); $\lambda_{max}$ (Nujol): 3400, 1740 and 1610 cm$^{-1}$; (a) δ (CDCl$_3$) 0.9 (15H, m, 2×CH(CH$_3$)$_2$ and CH$_2$CH$_3$); 1.3(3H, d, J=6 Hz, CH$_3$CH); 1.2–2.4 (12H, m, 2×CH(CH$_3$)$_2$, CHCH$_2$CH and (CH$_2$)$_4$); 3.0–3.4 (5H, m, 3×CH and CH$_2$NH); 3.7 (3H, s; CH$_3$—O), 4.3(1H, t, J=8 Hz, NH); 6.94 (1H,m,NH) and 7.85 (1H, d, NH).

Elution with 50% ethyl acetate hexane afforded N[1-(R)-methoxycarbonylethyl]-L-leucyl-L-valine N-hexylamide, (0.5 g) which crystallised from methanol/water as needles m.p. 98°–101° C.; $[\alpha]_D^{20} = -43°$ (C=0.2, MeOH); (Found: C,62.7; H,10.2; N,10.5. $C_{21}H_{41}N_3O_4$ requires C,63.1; H,10.3; N,10.5%); $\nu_{max}$ (Nujol) 3250, 3060, 1730 cm$^{-1}$; δ(CDCl$_3$) 0.9 (15H,m, 2×(CH(CH$_3$)$_2$ and CH$_2$CH$_3$); 1.3 (3H,d,J=6 Hz, CH$_3$ CH); 1.2–2.4 (12H,m, 2×CH(CH$_3$)$_2$, CHCH$_2$CH and (CH$_2$)$_4$); 3.0–3.3 (4H,m, 2×NHCHCO, CH$_2$); 3.44(1H,q,J=7 Hz, val α-CH); 3.7(3H,s CH$_3$—O); 4.28 (1H, q, J=7 Hz,NH); 7.16 (1H,m,NH); and 7.92 (1H,d, J=8 Hz,NH).

The N-(t-butyloxycarbonyl)-L-leucyl-L-valine N-hexylamide used as a starting material was prepared as follows:

N-Tertiarybutyloxycarbonyl-L-valine N-hexylamide (15 g) in dichloromethane (30 ml) was treated with trifluoroacetic acid (30 ml) at room temperature for 45 minutes. The excess trifluoroacetic acid was removed in vacuo and the residue redissolved in dichloromethane. The solution was adjusted to pH7 with triethylamine, N-tertiarybutyloxycarbonyl-L-leucine (13 g), 1-hydroxybenzotriazole (7 g) and DCC (10 g) were added and the reaction mixture stirred at room temperature overnight. The reaction mixture was filtered and the organic phase washed with aqueous sodium hydrogen carbonate, 1M citric acid and then water, dried over sodium sulphate and concentrated in vacuo to a gum. The gum was chromatographed on silica developed in a gradient of 20% ethyl acetate to 50% ethyl acetate in petrol to afford N-tertiarybutyloxycarbonyl-L-leucyl-L-valine N-hexylamide (19 g) which crystallised from ether hexane as needles; m.p. 115°–116° C.; (Found: C,63.2; H,10.3; N,10.1. $C_{22}H_{43}N_3O_4 \cdot 1/4H_2O$ requires C,63.2; H,10.5; N 10.1%); $\nu_{max}$ (nujol) 3300, 3080, 1680, 1630 and 1520 cm$^{-1}$; δ(CDCl$_3$) 0.9 (15H,m, 2×CH(CH$_3$)$_2$ and CH$_2$CH$_3$); 1.1–2.3 (12H,m, (CH$_2$)$_4$, CH$_2$CH(CH$_3$)$_2$, CHCH(CH$_3$)$_2$); 1.45 (9H,s,C(CH$_3$)$_3$); 3.25 (2H,m,NHCH$_2$); 4.12 (1H,m, α-CH from leucyl residue); 4.2 (1H,t, J=5 Hz., α-CH from valyl residue); 5.07 (1H,m,NH); 6.55 (1H,m,NH) and 6.80 (1H,d,J=10 Hz, NH).

The N-t-butyloxycarbonyl-L-valine N-hexylamide required as a starting material in the preparation above was synthesised as follows:

Tertiarybutyloxycarbonyl-L-valine (25 g) in dichloromethane (200 ml) was treated with 1-hydroxybenzotriazole (15.5 g) hexylamine (11.6 g) and DCC (26 g) at room temperature for 2 days. The solution was filtered and the organic phase washed with aqueous sodium hydrogen carbonate, aqueous citric acid (1M) and water, dried over sodium sulphate and concentrated in vacuo to afford tertiary butyloxycarbonyl-L-valine N-hexylamide (28 g) which crystallised from methanol-water as needles; m.p. 74°–76° C.; (Found: C,63.8; H,10.6; N,9.4. $C_{16}H_{32}N_2O_3$ requires C,64.0; H,10.7; N,9.32%); $\nu_{max}$(Nujol): 3280 and 1630 cm$^{-1}$; δ(CDCl$_3$) 0.8–1 (9H,m, 3×CH$_3$); 1.3 (8H,m,(CH$_2$)$_4$); 1.45 (9H,s, (CH$_3$)$_3$C); 2.1 (1H,m,CH(CH$_3$)$_2$); 3.3 (2H,m, NHCH$_2$); 3.9 (1H,dd, J=8 Hz and 5 Hz., α-CH); 5.2 (1H,d, J=8Hz, CONH) and 6.26 (1H,m,NH).

EXAMPLE 2

N-[1-(R)-Methoxycarbonylethyl]-L-leucyl-O-benzyl-L-tyrosine N-methylamide

N-Boc-O-benzyl-L-tyrosine methylamide (3 g, 7.7 mM) was dissolved in 1:1 TFA/CH$_2$Cl$_2$ (100 ml). After 15 min. the solvent was removed in vacuo and the residue taken up in H$_2$O (100 ml), neutralised with NaHCO$_3$ and extracted into CH$_2$Cl$_2$ (3×100 ml). The organic extract was dried and evaporated in vacuo to yield a white solid (2.2 g). This material in CH$_2$Cl$_2$ (50 ml) and DMF (5 ml) was treated at 0° with N-[1-(R)-methoxycarbonylethyl]-L-leucine (1.3 g, 6 mM), 1-hydroxybenzotriazole (960 mg, 6.4 mM) and dicyclohexylcarbodiimide (1.3 g, 6.5 mM) and the mixture allowed to warm to room temperature over 2 h. After a further 12 h the reaction mixture was filtered, washed with sat. NaHCO$_3$ and then brine, dried and then evaporated in vacuo to yield a solid, 2.5 g (68%). Recrystallisation from CH$_2$Cl$_2$/hexane gave the title compound; m.p. 65°–68°; $[\alpha]_D^{20} = -3.3°$ (C=0.2, MeOH); (Found: C, 66.72; H, 7.61; N, 8.72. $C_{27}H_{37}N_3O_5$ requires C, 67.02; H, 7.71; N, 8.69%); $\nu_{max}$ (nujol) 3280 br, 1735, 1635 and 1510 cm$^{-1}$; δ(CDCl$_3$) 0.87 and 0.9 (each 3H, each d, J=4 Hz. and 2.5 Hz, (CH$_3$)$_2$CH); 1.1(1H,m, (CH$_3$)$_2$CH$_2$CH); 1.3 (3H,d,J=8.5 Hz., CH$_3$CH); 1.45 (2H,m, (CH$_3$)$_2$CH$_2$CH); 1.58 br (1H,s, CHNHCH, exch); 2.77 (3H,d,J=6 Hz, NHCH$_3$); 3.0 (1H,dd,J=12 and 8 Hz, CH$_2$C$_6$H$_4$); 3.07 (1H,m, (CH$_3$)$_2$CH$_2$CH); 3.18 (1H,dd,J=12 and 6 Hz, CHCH$_2$C$_6$H$_4$); 3.38 (1H,q,J=8.5 Hz, CH$_3$CH); 3.68 (3H,s,OCH$_3$), 4.62

(1H,q,J=7 Hz, NHCH(CH$_2$C$_6$H$_4$)CO); 5.02 (2H,s, OCH$_2$C$_6$H$_5$); 6.71 br (1H,q,J ca 5 Hz, exch. NHCH$_3$); 6.89 and 7.12 (each 2H, each d, each J=8 Hz, C$_6$H$_4$); 7.4 (5H,m,C$_6$H$_5$) and 7.75 (1H,d, J=9 Hz, exch, CONHCHCO); m/e 484 (100%, [M+1]$^+$), 381 (27) and 172 (28).

The syntheses for the two starting materials required in the preparation above are described in the following paragraphs.

(a) N-t-Butyloxycarbonyl-O-benzyl-L-tyrosine N-Methylamide

N-t-Butyloxycarbonyl-O-benzyl-L-tyrosine (7.4 g, 20 mM), 1-hydroxybenzotriazole (3 g, 20 mM), methylamine hydrochloride (1.3 g, 20 mM) and N-methyl morpholine were dissolved in CH$_2$Cl$_2$ (200 ml) and cooled to 0° C. Dicyclohexylcarbodiimide (4.2 g, 20 mM) was added and the reaction allowed to warm to room temperature over 4 h. After a further 12 h the reaction mixture was filtered; the filtrate was washed with sat NaHCO$_3$, 3N citric acid and brine, dried and evaporated in vacuo to give the required N-methylamide which was recrystallised from CH$_2$Cl$_2$ and hexane (4.5 g, 58%); m.p. 165°–172°; $[\alpha]_D^{20}$ = +15.2° (C=0.2, MeOH); (Found: C, 68.85; H, 7.43; N, 7.39. C$_{22}$H$_{28}$N$_2$O$_4$ requires C, 68.73; H, 7.34; N, 7.29%); $\nu_{max}$ (nujol) 3330, 1685, 1672, 1655 and 1520 cm$^{-1}$; $\delta$(CDCl$_3$) 1.4 (9H,s, (CH$_3$)$_3$C); 2.91 (3H,d, J=5 Hz, NHCH$_3$); 3.0 (2H,m,CH$_2$C$_6$H$_4$); 4.26 (1H,q, J=7.5 Hz, NHCH(CH$_2$)CO); 5.04 (2H,s, OCH$_2$C$_6$H$_5$); 5.08 br (1H,s, exch, NH); 5.84 br (1H,s,exch); 6.91 and 7.09 (each 2H, each d, each J=8 Hz., C$_6$H$_4$) and 7.4 (5H,m,C$_6$H$_5$); m/e 385 (68%, [M+1]$^+$), 329 (100), 285 (66) and 267 (58).

(b) N-[1-(R)-Methoxycarbonylethyl]-L-luecine

This was prepared in two steps from L-leucine benzyl ester as illustrated below:

L-Leucine benzyl ester, para-toluene sulphonic acid salt (120 g, 0.3M) was dissolved in dry methanol (300 ml) and the pH (moist pH paper) adjusted to 6 using Et$_3$N and acetic acid. Methyl pyruvate (62.4 g, 0.6M) in dry methanol (10.0 ml) and 3 Å molecular sieves were added; the mixture was cooled to 5° and then NaBH$_3$CN (100 g, 1.58M) in methanol (600 ml) added. After stirring for 3 days the reaction mixture was filtered and evaporated in vacuo. The residual white solid was partitioned between H$_2$O (500 ml) and CH$_2$Cl$_2$ (4×200 ml); the organic phase was evaporated to a yellow oil and then partitioned between hexane (250 ml) and 1M oxalic acid (4×250 ml). The aqueous phase was neutralised with NaHCO$_3$ and extracted into CH$_2$Cl$_2$ (4×250 ml). The organic phase was dried and evaporated in vacuo to yield a yellow oil (90 g), which was chromatographed on SiO$_2$ using a gradient of EtOAc in hexane as eluant. The faster running diastereoisomer, N-[1-(R)-methoxycarbonylethyl]-L-leucine benzyl ester, was isolated as an oil (22 g, 20%); $[\alpha]_D^{20}$ = –49.5° (C=0.2, MeOH); (Found: C, 66.06; H, 8.19; N, 4.75. C$_{17}$H$_{26}$NO$_4$ requires C, 66.42; H, 8.19; N, 4.54); $\nu_{max}$ (nujol) 1735 cm$^{-1}$; $\delta$(CDCl$_3$) 0.89 and 0.92 (each 3H, each d, each J=3.5 Hz., (CH)$_3$)$_2$); 1.29 (3H,d,J=7 Hz; CH$_3$); 1.5 (2H,m,CH$_2$CH); 1.74 (2H,m,NH and CH$_2$CH(CH$_3$)$_2$); 3.34 (1H,q, J=7 Hz, CHCH$_3$), 3.39 (1H,t,J=7 Hz, CH$_2$CH(NH)CO); 3.69 (3H, s, C$_6$H$_3$); 5.15 (2H,m,OCH$_2$C$_6$H$_5$) and 7.35 (5H,s,C$_6$H$_5$); m/e 308 (100%; [M+1]$^+$); 232 (53) and 172 (44).

The slow running diastereoisomer, N-[1-(S)-methoxycarbonylethyl]-L-leucine benzyl ester, was isolated as an oil (11.3 g, 10%); $[\alpha]_D^{20}$=1.73° (C=0.2, MeOH); (Found: C, 66.42; H, 8.30; N, 4.54. C$_{17}$H$_{26}$NO$_4$ requires C, 66.42; H, 8.19; N, 4.55%) $\Gamma_{max}$ (film) 1730 cm$^{-1}$; $\delta$(CDCl$_3$) 0.87 and 0.9 (each 3H, each d, each J=5.5 Hz, (CH$_3$)$_2$CH); 1.27 (3H,d,J=7 Hz, CH$_3$CH); 1.49 (2H,m, (CH$_3$)$_2$—CHCH$_2$); 1.74 (1H, heptet, J=7 Hz, (CH$_3$)$_2$CH); 2.2 br (1H,s,NH), 3.3 (2H,m,CHNHCH), 3.65 (3H,s,OCH$_3$); 5.13 (2H,s,OCH$_2$C$_6$H$_5$) and 7.35 (5H,s,C$_6$H$_5$); m/e 308 (100%, [M+1]$^+$) and 172 (100).

The R-benzyl ester (13 g, 42 mM) was dissolved in methanol (300 ml) and hydrogenated over 10% palladium on charcoal at atmospheric pressure. The catalyst was removed by filtration through celite and the filtrate evaporated in vacuo to yield a white gum, which was crystallised from MeOH/Et$_2$O to give the required leucine derivative as a white crystalline solid (7.5 g, 82%); mp 150°–151°; (Found: C, 55.27; H, 8.72; N, 6.43. C$_{10}$H$_{19}$NO$_4$ requires C, 55.3; H, 8.81; N, 6.45%); $[\alpha]_D^{20}$ 8.4 (C=0.2, MeOH); $\nu_{max}$ (nujol) 3400 br, 2500 br and 1755 cm$^{-1}$; $\delta$(d$^6$DMSO) 0.85 (6H, m, (CH$_3$)$_2$CH$_2$); 1.17 (3H,d,J=7 Hz, CH$_3$CH); 1.38 (2H,m, (CH$_3$)$_2$CHCH$_2$); 1.74 (1H, heptet, J=6 Hz, (CH$_3$)$_2$CH); 3.14 (1H, t, J=7 Hz, NHCH(CH$_2$)CO$_2$H); 3.29 (1H,q,J=7 Hz, CH$_3$CH) and 3.6 (3H,s,OCH$_3$); m/e 218 (100%, [M+1]$^+$), 172 (27) and 158 (17).

EXAMPLE 3

N-[2-N-[N-(2,4-Dinitrophenyl)-L-prolyl-L-leucyl-]amino-1-(R)-methoxycarbonylethyl]-L-leucyl-O-benzyl-L-threonine N-Methylamide This was prepared starting from methyl N-t-butyloxycarbonyl-N-benzyloxycarbonyl(R)-2,3-diaminopropionate and benzyl 4-methyl-2-oxo-pentanoate in the steps described in the following paragraphs.

(a) N-[2-N-(t-Butyloxycarbonyl)amino-1-(R)-methoxycarbonylethyl]-L-leucine Benzyl ester To a stirred solution of methyl N-t-butyloxycarbonyl-N-benzyl oxycarbonyl-(R)-2,3-diaminopropionate (25 g) in THF (150 ml) and acetic acid (8 ml) was added palladised charcoal (10%, 2 g) and the mixture hydrogenated at 25° and 760 mmHg for 2 h. The catalyst was removed by filtration and to the filtrate was added THF (50 ml), benzyl 4-methyl-2-oxopentanoate (50 g, from the corresponding acid by treatment at reflux with benzyl alcohol in the presence of para-toluene sulphonic acid and azeotropic removal of water) in THF (50 ml) and finally water (70 ml). The pH of the rapidly stirred solution was adjusted to 6.5 with triethylamine and sodium cyanoborohydride (4.5 g) was added portionwise over 0.5 h. The pH was maintained at 6.5 by periodic addition of acetic acid. After 16 h at 20°, a further portion of sodium cyanoborohydride (2 g) was added and stirring continued for 24 h. The reaction mixture was concentrated in vacuo and the residue was partitioned between CH$_2$Cl$_2$ (200 ml) and water (100 ml). The aqueous layer was washed with fresh CH$_2$Cl$_2$ (2×100 ml) and the combined organic extracts washed successively with 3N-citric acid solution water and finally saturated aqueous sodium hydrogen carbonate solution and then dried over MgSO$_4$. The oil isolated from the CH$_2$Cl$_2$ was purified by chromatography on silica eluting with CH$_2$Cl$_2$ in an increasing ethyl acetate gradient to give the required benzyl ester (9.6 g) as an oil which slowly crystallised, m.p. 59.5°–61° (from etherhexane); $[\alpha]_D^{25}$=22.1° (C=1.1, MeOH); (Found: C, 62.40; H, 8.08; N, 6.57. C$_{22}$H$_{34}$N$_2$O$_6$ requires C, 62.54; H, 8.11; N, 6.36%); $\nu_{max}$ (CHCl$_3$) 1730 and 1705 cm$^{-1}$;$\delta$ (CDCl$_3$) 0.89 (6H, t, J=6.3 Hz, CH(CH$_3$)$_2$);

1.43 (9H,s, C(CH₃)₃); 1.50 (2H, m, C$\underline{H}$₂CH); 1.76 (2H,m,CH₂C$\underline{H}$(C$\underline{H}$₃)₂ and NH); 3.35 (4H,$\underline{m}$,CH₂N and 2×α-C$\underline{H}$); 3.$\overline{67}$ (3H,s,OCH₃); 4.98 br (1H,s,NHCOO), 5.12 (2$\underline{H}$,d, J=11.5 Hz, CH₂Ph) and 7.36 (5H, m,C₆H₅); m/e 423 ([M−1]+).

(b) N-[2-N-(t-Butyloxycarbonyl)amino-1-(R)-methoxycarbonylethyl]-L-leucyl-O-benzyl-L-threonine N-Methylamide The foregoing benzyl ester (6 g) in methanol (50 ml) was hydrogenated at S.T.P. over 10% palladised charcoal (100 mg) for 0.5 h. The catalyst was removed by filtration and the material recovered from the methanol was recrystallised from methanol-ether to give the intermediate carboxylic acid (4.5 g), m.p. 147°–148°. A portion of this material (2.8 g) in CH₂Cl₂ (100 ml) and DMF (20 ml) was treated at 0° with 1-hydroxybenzotriazole (1.3 g), and N-ethyl-N'-(3-dimethylaminopropyl)carbodiimide hydrochloride (1.61 g). After 0.5 h at 0°, L-O-benzyl-threonine N-methylamide (1.86 g) in CH₂Cl₂ (10 ml) was added and the mixture allowed to warm to 20° over 1 h. After 36 h at 20°, the reaction mixture was washed in turn with saturated sodium hydrogen carbonate solution, 3N-citric acid solution and finally brine and then dried and evaporated in vacuo. Crystallisation of the resulting oil from ether-pentane gave N-[2-N-(t-butyloxycarbonyl)amino-1-(R)-methoxycarbonylethyl]-L-leucyl-O-benzyl-L-theronine N-methylamide (3 g), m.p. 95°–97°; (Found; C, 60.42; H, 8.20; N, 10.44. C₂₇H₄₄N₄O₇ requires C, 60.43; H, 8.26; N, 10.44%); δ (CDCl₃) 0.94 (6H,d, J=6.2 Hz., CH(CH₃)₂); 1.13 (3H,d,J=6.4 Hz, CHC$\underline{H}$₃); 1.43 (9$\overline{H}$,s,C(CH₃)₃); 1.54−1.85 (3H,m,C$\underline{H}$₂CH); 1.95 broad (1H,s, NH); 2.82 (3H,d, J=4.8 Hz, N$\underline{H}$CH₃); 3.1−3.62 (4H,m,NCH₂, OCH and αCH), 3.65 (3$\overline{H}$,s,OCH₃), 4.3 (1H,m,α-C$\underline{H}$), 4.45 (1$\underline{H}$,dd, J=6.3 and 2.3 Hz, α-C$\underline{H}$); 4.54 and 4.$\overline{62}$ (each 1H, each d, each J=11.6 Hz, C$\overline{H}$₂Ph); 5.05 broad (1H,s, NHCOO), 7.05 (1H,m,N$\underline{H}$CH₃), 7.32 (5H,m,C₆H₅) and 7.88 (1H,d, J=8.4 Hz, N$\overline{H}$).

(c) N-[2-N-[N-(2,4-Dinitrophenyl)-L-prolyl-L-leucyl]amino-1-(R)-methoxycarbonylethyl]-L-leucyl-O-benzyl-L-threonine N-Methylamide To a stirred solution of the foregoing t-butyloxycarbonyl protected peptide (536 mg) in CH₂Cl₂ (3 ml) was added trifluoroacetic acid (3 ml) at 0°. The solution was allowed to warm to 20° and then stirred at this temperature for 2 h. The residue after evaporation of the organic solvents was taken into CH₂Cl₂ and the solution washed with saturated sodium hydrogen carbonate solution, dried (Na₂SO₄) and evaporated in vacuo to yield N-[2-amino-1-(R)-methoxycarbonylethyl]-L-leucyl-O-benzyl-L-threonine N-methylamide (330 mg). This material in CH₂Cl₂ (10 ml) was added to a solution of N-[N-(2,4-dinitrophenyl)-L-prolyl]-L-leucine (330 mg) in CH₂Cl₂ (10 ml) containing 1-hydroxybenzotriazole (132 mg) and N-ethyl-N'-(3-dimethylaminopropyl)carbodiimide hydrochloride (191 mg) stirred at 5°. After 16 h at 4° the solvent was removed in vacuo and the residue in ethyl acetate washed in turn with water, saturated sodium hydrogen carbonate solution and finally 3N-citric acid solution. The material isolated from the ethyl acetate was recrystallised from CH₂Cl₂— ether to give the required peptide (440 mg), m.p. 138°–142°; (Found: C, 57.34; H, 6.92; N, 13.61. C₃₉H₅₆N₈O₁₁ requires C, 57.62; H, 6.94; N, 13.78%); ν$_{max}$ (CHCl₃) 3295, 1730 and 1635 cms⁻¹; δ(CDCl₃) 0.95 (12H,m, 2×CH(CH₃)₂); 1.14 (3H,d,J=6.3 Hz, C$\underline{H}$₃CH); 1.3−2.15 and $\overline{2.45}$ (10H,m,CH₂CH₂ and 2×C$\underline{H}$₂CH); 2.74 (3H,s,NHCH₃); 3.3 (3H,m,CH₂N and C$\underline{HO}$); 3.56 (3H,m,CH₂$\overline{N}$ and α-C$\underline{H}$); 3.63 (3H,s,OCH₃); 4.06, 4.25 and 4.56 (1H,2H and 1H respectively, each m, 4×αC$\underline{H}$); 4.43 and 4.55 (each 1H, each d, J=11.7 Hz, CH₂Ph); 7.00 (1H,d, J=9.5 Hz, 6-H in C₆H₃); 7.28 (5H,s,C₆H₅); 8.16 (1H,dd, J=9.5 and 2.8 Hz, 5-H in C₆H₃) and 8.54 (1H,d, J=2.8 Hz, 3-H in C₆H₃); m/e 813 ([M+1]+).

O-Benzyl-1-threonine N-methylamide used in step (b) above was prepared from N-t-butyloxycarbonyl-O-benzyl-L-threonine N-methylamide by exposure to trifluoroacetic acid in CH₂Cl₂. This in turn was prepared from N-t-butyloxycarbonyl-O-benzyl-L-threonine and methylamine using the procedure described in Example 2 for the tyrosine analogue.

N-[N-(2,4-Dinitrophenyl)-L-prolyl]-L-leucine used as starting material in stage (c) was prepared from N-(2,4-dinitrophenyl)-L-proline and leucine methyl ester using the coupling procedure involving N-ethyl-N'-(3-dimethylaminopropyl)carbodiimide hydrochloride as the condensing agent in the presence of 1-hydroxybenzotriazole (as illustrated in Example 3) followed by hydrolysis of the methyl ester with 2N-sodium hydroxide solution (see Example 5).

Methyl Nβ-t-butyloxycarbonyl-Nα-benzyloxycarbonyl-(R)-2,3-diaminopropionate, used as the starting material in stage (a), was prepared as follows:

To a stirred suspension of N-benzyloxycarbonyl-(R)-2,3-diaminopropionic acid [19.5 g; from Nα-benzyloxycarbonyl-D-asparagine exactly as described for the L-isomer in Synthesis, 266, (1981)] in dry methanol (60 ml) at −20° was added thionyl chloride (30 g) dropwise over 40 min. The reaction mixture was allowed to warm to 20° over 1 h and then heated at 50° for 1 h. The residue after removal of the solvent was recrystallised from methanol-ether to give methyl Nα-benzyloxycarbonyl-R-2,3-diaminopropionate hydrochloride (22.5 g); m.p. 170°–172°; (Found: C, 49.86; H, 5.89; N, 9.53. C₁₂H₁₇N₂O₄Cl requires C, 49.91; H, 5.93; N, 9.70%); ν$_{max}$ (Nujol) 3305, 1735 and 1688 cm⁻¹; δ (d⁶ DMSO) 3.00–3.32 (2H,m,CH₂NH₂); 3.7 (3H,s,OCH₃); 4.45 (1H,m,α-C$\underline{H}$); 5.09 (2H,s,CH₂Ph); 7.36 (5H,s,C₆H₅); 7.95 (1H,d,$\overline{J}$=7.5 Hz, NHCOO) and 8.28 broad (3H,s, NH₃); m/e 253 ([M+1]+). A portion of this material (22.5 g) in DMF (150 ml) was treated with Et₃N until the pH was 10. Di-t-butyl dicarbonate (16.8 g) was added to the solution stirred at 5°. After a further 2 h at 20°, the reaction mixture was filtered and evaporated in vacuo and the residue partitioned between ether and water. The aqueous layer was extracted twice more with fresh ether and the combined organic extracts washed in turn with ice cold 1N-hydrochloric acid, saturated sodium hydrogen carbonate solution and finally water. The oil isolated from the ether was crystallised from ethyl acetate-hexane to give methyl Nβ-t-butyloxycarbonyl-Nα-benzyloxycarbonyl-(R)-2,3-diaminopropionate (22.5 g); m.p. 89°–91°; (Found: C, 57.86; H, 6.95; N, 7.93. C₁₇H₂₄N₂O₆ requires C, 57.94; H, 6.86; N, 7.95%); ν$_{max}$ (CHCl₃) 3600 and 1700 cm⁻¹; δ 1.4 (9H,s, C(CH₃)₃); 3.5 broad (2H, s, CH₂N); 3.72 (3H, s, OCH₃); 4.4 (1H, α-C$\underline{H}$); 5.09 (2H, s, CH₂Ph); 5.2 broad (1H,s, NHCOO); 6.06 (1H, d, J=7.3 Hz, NHCOO) and 7.32 (5H, s, C₆H₅).

EXAMPLE 4

N-[1-(R)-Methoxycarbonylethyl]-L-leucyl-O-benzyl-L-tyrosine N-Methylamide

Leucine benzyl ester para-toluene sulphonic acid salt (113 g) in dry acetonitrile (800 ml) was treated with methyl 2-bromopropionate (62.7 ml) and N-methyl morpholine (100 ml) under reflux for 16 h. The reaction mixture was concentrated in vacuo and the residue in ethyl acetate washed with brine, dried ($Na_2SO_4$) and evaporated. Chromatography of the resulting oil on silica in 1:4 ethyl acetate-hexane gave N-[1-(R)-methoxycarbonylethyl]-L-leucine benzyl ester (45 g) as the faster running fraction. This material was treated exactly as described above in Example 2 to give the title compound.

EXAMPLE 5

N[1-(R)-Carboxyethyl]-L-leucyl-O-benzyl-L-tyrosine N-Methylamide

The methyl ester (1.5 g, 3.1 mM) from Example 2 was dissolved in methanol (20 ml) and treated with 1N sodium hydroxide (3.5 ml, 3.5 mM). After 18 h, the pH was adjusted to 5 with acetic acid and the solvent removed in vacuo to yield a white solid. Recrystallisation first from water and then from methanol-ether yielded the N-[1-(R)-carboxyethyl]-L-leucyl-O-benzyl-L-tyrosine N-methylamide as a white powder (1.02 g), m.p. 195°; $[\alpha]_D^{20}=+7.2°$ (C=0.2, MeOH); (Found: C, 63.76; H, 7.64; N, 8.57. $C_{26}H_{35}N_3O_5.H_2O$ requires C, 64.05; H, 7.65; N, 8.62%); $\nu_{max}$ (Nujol) 3540 (br), 3330 and 1680 cm$^{-1}$; δ (d$^6$DMSO) 0.82 (3H,d, J=6 Hz, $(CH_3)_2$CH); 0.87 (3H,d, J=6 Hz, $(CH_3)_2$CH); 1.13 (3H,d, J=7 Hz., $CH_3$CH); 1.24 (2H,t, J=6 Hz., $CHCH_2$CH: 1.59 (1H,m, $(CH_3)_2CHCH_2$); 2.63 (3H,d, J=5 Hz, $NHCH_3$); 2.72 (1H,dd, J=11 and 12 Hz, $CHCH_2C_6H_4$); 2.8 (1H,q, J=7 Hz, $CH_3CH(NH)CO_2H$); 2.95 (1H,dd, J=12 and 5 Hz, $CHCH_2C_6H_4$); 3.21 (1H,t, J=7.5 Hz, $NHCH(CH_2CH(CH_3)_2CO)$; 4.53 br (1H,m, $NHCH(CH_2C_6H_4)CO$); 5.08 (2H,s,$C_6H_4OCH_2C_6H_5$); 6.93 and 7.17 (each 2H, each d, each J=7.5 Hz, $C_6H_4O$); 7.48 (5H,m,$C_6H_5$); 7.98 br (1H,q, J=5 Hz, $NHCH_3$, exch) and 8.1 (1H,d, J=9 Hz., CHCONHCH, exch); m/e 470 (88% [M+1]$^+$), 452 (51), 424 (29), 285 (100) and 158 (49).

EXAMPLE 6

N[1-(R)-Carboxyethyl]-L-Leucine N-Phenethylamide

N[1-(R)-Ethoxycarbonylethyl]-L-Leucine N-phenethylamide (710 mg, 2.1 mM) was dissolved in MeOH (50 ml) and treated with 1N NaOH (3 ml, 3 mM) at room temperature. After 12 h, the reaction mixture was acidified with AcOH and evaporated in vacuo to a solid which was washed with $H_2O$ and dried to yield the title compound (400 mg); m.p. 201°-205°; (Found: C, 66.44; H, 8.55; N,9.11; $C_{17}H_{26}N_2O_3$ requires C,66.64; H,8.55; N,9.14%); $\nu_{max}$ (Nujol) 3330, 1660 and 1530 cm$^{-1}$; δ (d$^6$DMSO) 0.825 (6H,t,J=6.2 Hz, $(CH_3)_2$CH), 1.15 (3H,d, J=6.8 Hz, $CH_3$CH), 1.29 (2H,m,$CH_2$CH), 1.55 (1H, heptet,J=7 Hz, $CH(CH_3)_2$), 2.71 (2H,t,J=7 Hz, $CH_2C_6H_5$), 3.0 (1H,q,J=7 Hz, $CHCH_3$), 3.14 (1H,t,J=7 Hz, α-$CH$), 3.32 (2H,q,J=6 Hz, $NHCH_2CH_2$), 7.12 (5H,m,$C_6H_5$), 7.5 (2H,br S,OH and $CHNHCH$) and 8.15 (2H,t,J=5 Hz, $NHCH_2$).

The N[1-(R)-ethoxycarbonylethyl]-L-leucine N-phenethylamide required in the preparation above was synthesised as follows:

N[1-(R)-Ethoxycarbonylethyl]-L-leucine (1.39 g, 6 mM), N-ethyl-N'-(3-dimethylaminopropyl)-carbodiimide hydrochloride (1.16 g, 6 mM), 1-hydroxybenzotriazole (0.93 g, 6 mM) and phenethylamine (0.7 g, 6 mM) were dissolved in DMF (50 ml) at −6°. N-Methylmorpholine (0.62 g, 6.2 mM) was added and the reaction mixture allowed to warm to room temperature. After 12 h the solvent was removed in vacuo. The residue in EtOAc (150 ml) was washed with $H_2O$ (2×100 ml), dried and evaporated in vacuo to yield an oil which was purified by chromatography on $SiO_2$ in EtOAc to give N[1-(R)-ethoxycarbonylethyl]-L-leucine N-phenethylamide as an oil (1.84 g). For analysis, a portion of this material was dissolved in MeOH, treated with anhydrous HCl in $Et_2O$ and evaporated in vacuo to yield the corresponding hydrochloride as a foam; (Found: C,60.28; H,8.54; N,7.35; $C_{19}H_{30}N_2O_3.HCl.0.4H_2O$ requires C,60.35; H,8.48; N,7.41%); $[\alpha]_D^{20}=+9.4°$ (c=0.2, MeOH); $\nu_{max}$ (Nujol) 3400 (br), 3100 (br), 2510 (br), 2400 (br), 1740, 1670 and 1550 cm$^{-1}$; δ CDCl$_3$ 0.92 and 0.95 (6H, each d, each J=7 Hz, $(CH_3)_2$CH), 1.27 (3H, t, J=6.5 Hz, $CH_3CH_2$), 1.28 (3H,d,J=7 Hz, $CH_3$CH), 1.3-1.7 (3H,m,$CH_2$CH), 2.85 (2H,t,J=6 Hz,$CH_2CH_2C_6H_5$), 3.21 (1H,dd,J=10 Hz and 4 Hz, α-$CH$), 3.27 (3H,q,J=6.5 Hz, $CH_3CH$), 3.54 (2H,q,J=7 Hz, $NHCH_2CH_2$), 4.16 and 4.18 (2H, each q, each J=6.5 Hz, $OCH_2CH_3$) and 7.25 (6H,m,$C_6H_5$ and NHCO).

The starting material required in the preparation given above was synthesised in two steps from leucine benzyl ester as follows:

(a) N[1-(R)-Ethoxycarbonylethyl]-L-Leucine Benzylester

L-Leucine benzyl ester (186.65 g, 0.843M), ethyl 2-bromopropionate (153.1 g, 0.846M) and N-methylmorpholine (165 ml, 1.5M) were dissolved in dry $CH_3CN$ (800 ml) and refluxed for 12 h. The solvent was removed in vacuo and the residue partitioned between $H_2O$ (21) and EtOAc (3×11). The organic phase was washed with brine, dried and evaporated in vacuo. The resulting oil was chromatographed on $SiO_2$ in 7.5% EtOAc in hexane to give the title compound (70 g) as the faster running fraction; (Found: C,67.02; H,8.42; N,4.25; $C_{18}H_{27}NO_4$ requires C,67.26; H,8.47; N,4.36); $\nu_{max}$ film 1730 cm$^{-1}$; δ (CDCl$_3$) 0.88 and 0.9 (each 3H, each d, each J=6.5 Hz, $CH(CH_3)_2$) 1.23 (3H,t,J=7 Hz,$CH_3CH_2O$), 1.27 (3H,d,J=7 Hz,$CH_3$CH), 1.5 (2H,m,$CHCH_2$), 1.7 (1H, heptet, J=7 Hz, $CH(CH_3)_2$), 2.2 (1H, br s,NH), 3.32 (2H,m, $CHNHCH$), 4.10 and 4.12 (each 1H, each q, each J=7 Hz, $OCH_2CH_3$), 5.12 (2H,s, $OCH_2C_6H_5$) and 7.34 (5H,s, $C_6H_5$); m/e 322 (100%, [m+1])$^+$, 260 (15), 186 (26) and 112 (28).

(b) N[1-(R)-Ethoxycarbonylethyl]-L-leucine

N[1-(R)-Ethoxycarbonylethyl]-L-leucine benzyl ester (69.09 g, 0.215M) was dissolved in MeOH (300 ml) and hydrogenated at 1 atmosphere over 5% palladium on charcoal (5 g). After 1.5 h, the catalyst was removed by filtration and the filtrate evaporated in vacuo to yield a solid (46.8 g) which was recrystallised from MeOH-/Et$_2$O to yield the title compound (24 g); m.p. 149°-150°; $[\alpha]_D^{20}=8.8°$ (C=1.4, MeOH); (Found: C,57.14; H,9.06; N,6.02; $C_{11}H_{21}NO_4$ requires C,57.12; H,9.15; N,6.06%); $\nu_{max}$ (Nujol) 3090 (br), 2300 (br), 1755 and 1560 cm$^{-1}$; δ (d$^6$DMSO) 0.86 and 0.87 (6H, each d, each J=6.5 Hz, $(CH_3)_2$CH), 1.19

(6H,m,OCH$_2$CH$_3$ and CHCH$_3$), 1.36 (2H,m, CHCH$_2$CH), 1.74 (1H, heptet, J=6.5 Hz, CH$_2$C$\underline{\text{H}}$(CH$_3$)$_2$), 3.14 (1H,t,J=6.2 Hz, δ-C$\underline{\text{H}}$), 3.27 (1H,q,$\overline{\text{J}}$=6.8 Hz,NHCHCH$_3$) and 4.07 (2$\overline{\text{H}}$,q,J=7 Hz,OCH$_2$CH$_3$); m/e 23$\overline{2}$ (100%, [m+1]+), 186 (3) and 158 (7).

EXAMPLE 7

N[1-(R)-Carboxy-3-methylthiopropyl]-L-leucyl-O-methyl-L-tyrosine N-methylamide This was prepared from D-methionine methyl ester hydrochloride, 2-oxo-4-methylpentanoic acid and O-methyl-2-tyrosine in the steps described in the following paragraphs.

(a) N[1-(R)-Carbomethoxy-3-methylthiopropyl]-L-leucyl-O-methyl-L-tyrosine N-methylamide D-Methionine methyl ester hydrochloride (10 g, 50 mM) and 2-oxo-4-methylpentanoic acid t-butyl ester (9.3 g, 50 mM) were dissolved in THF (75 ml) and H$_2$O (25 ml). The pH was adjusted to 6.5 with N-methylmorpholine, NaCNBH$_3$ (630 mg, 10 mM) was added, followed after 2 h by a further portion (400 mg). After 18 h the reaction mixture was evaporated in vacuo and then partitioned between EtOAc (100 ml) and sat.NaHCO$_3$ solution (2×100 ml). The oil isolated from the organic layer was chromatographed on SiO$_2$ using a gradient of 5-10% EtOAc in hexane. The faster running fraction afforded the required isomer as an oil (1.4 g). δ (CDCl$_3$) 0.96 (6H,m, (CH$_3$)$_2$CH), 1.5 (9H,m, (CH$_3$)$_3$C), 1.4-2.0 (5H,m, CH$_2$C$\underline{\text{H}}$ and SCH$_2$CHCH), 2.1 (3H,S,CH$_3$S), 2.62 (2$\overline{\text{H,m}}$, SCH$_2$CH$_2$), 3.$\overline{17}$ and 3.38 (each 1H, t, each J=7 Hz, C$\underline{\text{H}}$NHCHO and 3.7 (3H,s,OCH$_3$)]. The slower running isomer was also obtained as an oil (1.2 g). δ (CDCl$_3$) 0.95 (6H,m, (CH$_3$)$_2$CH), 1.5 (9H,s, (CH$_3$)$_3$C), 1.5-2.1 (5H,m, SC$\underline{\text{H}}_2$CH$_2$CH and CH$_2$CH), 2.09 (3H,s,CH$_3$S), 2.6 (2H,m,SC$\underline{\text{H}}_2$CH$_2$), 3.08 and 3.22 (each 1H, each dd, each J=7 Hz, CHNHC$\underline{\text{H}}$) and 3.7 (3H,s,OCH$_3$)].

The faster runnng t-butyl ester (2.9 g, 9 mM) from above was dissolved in TFA (50 ml) and H$_2$O (0.5 ml). After 3 h the mixture was evaporated in vacuo, toluene (50 ml) was added and the solution was reevaporated in vacuo. The resulting oil was dissolved in CH$_2$Cl$_2$ (100 ml) and the pH adjusted to 7 (moist pH paper). O-Methyl-L-tyrosine N-methylamide (2.0 g, 10 mM) and 1-hydroxybenzotriazole (1.5 g, 10 mM) were added. The reaction mixture was cooled to 0°, treated with dicyclohexylcarbodiimide (2.1 g, 10 mM) and then allowed to warm slowly to room temperature. After 18 h, the mixture was filtered and the filtrate washed with H$_2$O and sat. NaHCO$_3$ solution. After drying, the solvent was removed in vacuo to yield an oil which was chromatographed on SiO$_2$ in 1:1 EtOAc/hexane. The relevant fractions yielded, after recrystallisation from Et$_2$O/hexane, the title compound (1.4 g); m.p. 108°-111°; (Found: C,58.62; H,7.91; N,8.85; C$_{23}$H$_{35}$N$_3$O$_5$S requires C,59.07; H,7.97; N,8.96%); ν$_{max}$ (Nujol) 3380 (br), 1740, 1610 and 1560 cm$^{-1}$; δ (CDCl$_3$) 0.86 and 0.87 (each 3H, each d, each J=6 Hz, (CH$_3$)$_2$CH), 1.15 and 1.4 (each 1H, each m, CH$_2$CH($\overline{\text{CH}}_3$)$_2$), 1.6 (1H,m,CH), 1.90 (2H,m,SCH$_2$C$\underline{\text{H}}_2$), 2.08 (3H,s,CH$_3$S), 2.5 (2H,m, SCH$_2$), 2.77 (3H,d,J=6 Hz, NHCH$_3$), 3.05 (3$\underline{\text{H}}$,m,CH$_2$C$_6$H$_5$ and α-C$\underline{\text{H}}$) 3.47 (1H,t,J=5 $\overline{\text{Hz}}$, α-C$\underline{\text{H}}$), 3.7 (3H,$\underline{\text{s}}$,OCH$_3$), 3.8 (3$\underline{\text{H,s}}$,CO$_2$CH$_3$), 4.63 (1H,q,J=7 Hz, α-C$\underline{\text{H}}$), 6.69 (1H,brq,J=6 Hz, NHCH$_3$), 6.82 and 7.13 (each 2H, each d, J=9 Hz, $\overline{\text{C}}_6$H$_4$) and 7.53 (1H,d,J=9 Hz, CONHCH); m/e 684 (100%, [m+1]+) and 232 (27).

(b) N[1-(R)-Carboxy-3-methylthiopropyl]-L-leucyl-O-methyl-L-tyrosine N-Methylamide N[1-(R)-Carbomethoxy-3-methylthiopropyl]-L-leucyl-O-methyl-L-tyrosine N-methylamide (100 mg, 0.2 mM) was dissolved in MeOH (10 ml) and treated with 1N NaOH (0.25 ml, 0.25 mM). After 18 h another portion of 1N NaOH (0.5 ml, 0.5 mM) and H$_2$O (2 ml) were added. After a further 18 h the reaction mixture was acidified with AcOH and evaporated in vacuo. The resulting white solid was chromatographed on C$_{18}$-Silica eluting with a gradient of 10% to 40% MeOH in H$_2$O. The relevant fractions were pooled and evaporated in vacuo; the residue was recrystallised from hot H$_2$O to yield the title compound (20 mg); m.p. 170-180; (Found: C,56.88; H,7.49; N,9.05; calculated for C$_{22}$H$_{35}$N$_3$O$_5$S,.0.6H$_2$O: C,56.90; H,7.86; N,9.0 5%); ν$_{max}$ (Nujol) 3340, 1650 and 1625 cm$^{-1}$; δ (d$^6$DMSO) 0.82 (6H,t,J=7 Hz, (CH$_3$)$_2$CH), 1.17 and 1.5-1.9 (5H, m, CHCH(CH$_3$)$_2$ and SCH$_2$CH$_2$), 2.04 (3H, s,CH$_3$S), 2.3 (2$\overline{\text{H}}$, m, —SCH$_2$), 2.6 (3$\overline{\text{H}}$, d, J=5 Hz, NHCH$_3$), 2.6-2.95 (3H, m, CH$_2$C$_6$H$_4$ and α-CH),), 3.14 (1$\overline{\text{H}}$, t, J=7 Hz, α-CH), 3.7$\overline{\text{(3}}$H, s, OCH$_3$), 4.$\overline{25}$ (1H, m, —CH), 6.8 and 7.12 ($\overline{\text{2}}$×2H, each d, each J=9 Hz, C$_6$H$_4$), 7.88 (1H, q, J=5 Hz, NHCH$_3$) and 8.18 (1H, d, J=9 Hz, NHCH); m/e 454 (1$\overline{\text{00}}$%, [m+1]+).

O-Methyl-L-tyrosine N-methylamide used in stage (a) above was prepared from Z-L-tyrosine as follows:

(i) Z-L-Tyrosine-O-methyl ether

Z-L-Tyrosine (150 g, 0.476M) was dissolved with stirring in dilute aqueous sodium hydroxide (42 g, 1.05M in 750 ml H$_2$O). Dimethyl sulphate (51 ml, 0.54M) was then added dropwise over 30 min. to this solution at room temperature. After 2 h further NaOH was added (4.2 g, 0.105M in 40 ml H$_2$O) followed by dimethyl sulphate (5.1 ml) after which the reaction was allowed to stir overnight at room temperature. The reaction was then acidified to pH 2, extracted with CH$_2$Cl$_2$ and the CH$_2$Cl$_2$ layer washed with aqueous sodium chloride, dried (MgSO$_4$) and concentrated in vacuo to yield the crude product. Recrystallisation from ethyl acetate/hexane gave the required methyl ether (155 g); m.p. 114°-115°; (Found: C, 65.84; H, 5.82; N, 4.22. C$_{18}$H$_{19}$NO$_5$ requires C, 65.64; H, 5.81; N, 4.25%); ν$_{max}$ (CHCl$_3$) 3412 and 1715 cm$^{-1}$; δ(CDCl$_3$) 3.1 (2H, m, CH$_2$C$_6$H$_4$); 3.76 (3H, s, OCH$_3$); 4.66 (1H, dd, J=8 and 3$\overline{\text{ H}}$z, α-C$\underline{\text{H}}$); 5.1 (2H, m, C$\underline{\text{H}}_2$C$_6$H$_5$); 5.23 (1H, d, J=8 Hz, N$\underline{\text{H}}$); 6.8 (2H, d, J=8.$\overline{\text{6 H}}$z, Tyr H-3, H-5); 7.05 (2H, d, J$\overline{\text{=}}$8.6 Hz, Tyr H-2, H-6); 7.33 (5H, broad s, C$_6$H$_5$); m/z 330 (68% [M+1]+), 285 (100% [M-CO$_2$H]$\overline{+}$).

(ii) N-(Benzyloxycarbonyl)-O-methyl-L-tyrosine N-Methylamide

To a stirred solution of N-(Benzyloxycarbonyl)-O-methyl-L-tyrosine (155 g, 0.471M) in dry CH$_2$Cl$_2$ was added 1-hydroxybenzotriazole (63.6 g, 0.471M) followed by a solution of DCC (97.2 g, 0.471M) in CH$_2$Cl$_2$ (100 ml) added slowly at 0° C. After warming to room temperature over 1 hr, a solution of methylamine (30 g) in CH$_2$Cl$_2$ (250 ml) was added dropwise to the reaction mixture which was then stirred overnight at room temperature. The reaction was then filtered, washed with saturated aqueous sodium bicarbonate (×2), dried (MgSO$_4$) and concentrated in vacuo to give a solid. Recrystallisation from ethyl acetate/hexane gave the desired amide (142 g); m.p. 167°-170°; (Found: C, 66.72; H, 6.58; N, 8.29. C$_{19}$H$_{22}$N$_2$O$_4$ requires C, 66.65; H, 6.48; N, 8.18%) $\nu_{max}$ (CHCl$_3$) 3440, 1710 and 1672 cm$^{-1}$; δ(CDCl$_3$) 2.70 (3H, d, J=5 Hz, NCH$_3$); 2.98 (2H, m, CH$_2$C$_6$H$_4$); 3.77 (3H, s, OCH$_3$); 4.30 (1H, dd, J=7.6 and 3 Hz, α-CH); 5.06 (2H, m, OCH$_2$C$_6$H$_5$); 5.43 (1H, m, OCONH); 5.84 (1H, m, CONH); 6.80 (2H, d, J=8.6 Hz, Tyr H-3 and H-5); 7.15 (2H, d, J=8.6 Hz, Tyr H-2 and H-6); 7.32 (5H, m, C$_6$H$_5$); m/e 343 (100%, [m+1]$^+$).

(iii) O-Methyl-L-tyrosine N-Methylamide

To a solution of N-(Benzylocycarbonyl)-O-methyl-L-tyrosine N-methylamide (15.6 g, 0.056M) in ethanol (200 ml) and DMF (200 ml) was added 10% Pd/C (1 g) and trifluoroacetic acid (4 ml). Hydrogen was then passed through the solution for 3 h after which the reaction was filtered and concentrated in vacuo. The residue was dissolved in H$_2$O (150 ml), neutralised with sodium bicarbonate and extracted into CH$_2$Cl$_2$ (150 ml×5). The combined organic extracts were dried (Na$_2$SO$_4$) and concentrated in vacuo to yield an oil which subsequently crystallised. Recrystallisation from ethyl acetate/hexane gave O-methyl-L-tyrosine N-methylamide (9.0 g), m.p. 90°–91°; (Found: C, 63.49; H, 7.71; N, 13.44 C$_{11}$H$_{16}$N$_2$OA requires C, 63.44; H, 7.74; N, 13.45%) $\nu_{max}$ (CHCl$_3$) 3350 and 1660 cm$^{-1}$; δ(CDCl$_3$) 1.3 (2H, br, NH$_2$); 2.64 (1H, dd, J=13.8 and 9.2 Hz, CHC$_6$H$_4$); 2.80 (3H, d, J=5 Hz, NCH$_3$); 3.18 (1H, dd, J=13.8 Hz and 4 Hz, CHC$_6$H$_4$); 3.55 (1H, dd, J=9 Hz and 4 Hz, α-CH) 3.78 (3H, s, OCH$_3$); 6.85 (2H, d, J=8,2 Hz, Tyr H-3 and H-5); 7.12 (2H, d, J=8,2 Hz, Tyr H-2 and H-6); 7.28 (1H, br, CONH).

EXAMPLE 8

N-[4-N-(benzyloxycarbonyl)amino-1-(R)-methoxycarbonylbutyl]-L-leucyl-O-methyl-L-tyrosine N-Methylamide To a solution of methyl 5-N-(benzyloxycarbonyl)amino-2-bromo-pentanoate (10.3 g, 0.03M), L-leucyl-O-methyl-L-tyrosine N-methylamide (9.6 g, 0.03M) and N-methyl morpholine in dry acetonitrile (100 ml) was added sodium iodide (4.5 g, 0.03M). The mixture was then stirred and heated under reflux for 24 hr. The cooled reaction mixture was then filtered and evaporated in vacuo to yield an oil. Chromatography on silica eluting with dichloromethane in an increasing ethyl acetate gradient gave the title compound (2.8 g); m.p. 124°–127°; (Found: C, 63.7; H, 7.52; N, 9.56. C$_{31}$H$_{44}$N$_4$O$_7$ requires C, 63.68; H, 7.58; N, 9.58%); $\nu_{max}$ (CHCl$_3$) 3400, 1718 and 1660 cm$^{-1}$; δ(CDCl$_3$) 0.85 and 0.87 (each 3H, each d, each J=6 Hz, CH)CH$_3$)$_2$) 1.0–1.85 (8H, m, NHCH$_2$CH$_2$, CH$_2$, CH$_2$CH and NH); 2.74 (3H, d, J=5 Hz, NCH$_3$); 2.96–3.42 (6H, m, NHCH$_2$, α-CH×2, CH$_2$C$_6$H$_4$); 3.66 (3H, s, OCH$_3$); 3.75 (3H, s, OCH$_3$); 4.6 (1H, dd, J=13 Hz and 6 Hz, α-CH); 5.0 (1H, m, OCONH); 5.1 (2H, s, CH$_2$C$_6$H$_5$); 6.71 (1H, br, CONH); 6.80 (2H, d, J=8.6 Hz, Tyr H-3 and H-5); 7.10 (2H, d, J=8.6 Hz, Tyr H-2 and H-6); 7.35 (5H, m, C$_6$H$_5$); 7.56 (1H, m, CONH); m/e 585 (100% [m+1]$^+$).

The starting materials used in this preparation were synthesised as follows:

(a) L-Leucyl-O-methyl-L-tyrosine N-methylamide

To a solution of BOC-L-Leucine (5.26 g, 0.021M) in CH$_2$Cl$_2$ (40 ml) and DMF (10 ml) stirred at 0° was added N-ethyl-N'-(3-dimethylaminopropyl)carbodiimide hydrochloride (4 g, 0.021M). After 15 min., N-methyl morpholine (0.021M) was added followed by, after a further 10 min. at 0°, a solution of O-methyl-L-tyrosine N-Methylamide (4.3 g, 0.019M) in CH$_2$Cl$_2$. The reaction mixture was allowed to warm to room temperature and stirred overnight. The reaction was then concentrated in vacuo, and the residue in CH$_2$Cl$_2$, washed in turn with H$_2$O (200 ml), saturated aq. NaHCO$_3$ (200 ml), dilute HCl (1M; 200 ml), saturated aq. NaHCO$_3$ (200 ml) and water (150 ml), dried (Na$_2$SO$_4$) and evaporated in vacuo to a solid. Recrystallisation from ethyl acetate/hexane gave N-(Tertiarybutoxycarbonyl)-L-leucyl-O-methyl-L-tyrosine N-methylamide as a white crystalline solid, (4.5 g), m.p. 159–161; (Found: C, 62.65; H, 8.33; N, 9.96. C$_{22}$H$_{35}$N$_3$O$_5$ requires C, 62.69; H, 8.37; N 9.97%). $\nu_{max}$ (CDCl$_3$) 3400, 1700 and 1662 cm$^{-1}$; δ(CDCl$_3$) 0.91 (6H, dd, J=7 and 14 Hz, CH(CH$_3$)$_2$); 1.37 (9H, s, OC(CH$_3$)$_3$); 1.47–1.7 (3H, m, CH$_2$CH(CH$_3$)$_2$); 2.71 (3H, d, J=4.7 Hz, NHCH$_3$), 2.98 and 3.14 (each 1H, each m, CH$_2$C$_6$H$_4$); 3.78 (3H, s, OCH$_3$); 4.0 and 4.61 (each 1H, each m, 2×α-CH); 4.86, (1H, br s, OCONH); 6.40 and 6.55 (each 1H, each br s, CONH×2); 6.82 (2H, d, J=8.4 Hz, Tyr H-3 and H-5); 7.08 (2H, d, J=8.4 Hz, Tyr H-2 and H-6); m/e 422 (70%, [m+1]$^+$), 365 (70%, [m−58]$^+$).

To a stirred solution of N-Tertiarybutoxycarbonyl)-L-leucyl-O-methyl-L-tyrosine N-methylamide (7.0 g, M) in CH$_2$Cl$_2$ (40 ml) cooled at 10° was added trifluoroacetic acid (70 ml) and the resulting solution stirred at room temperature for 1 h. The reaction was then concentrated in vacuo, and the residue dissolved in water, neutralised with sodium bicarbonate and extracted with CH$_2$Cl$_2$. The organic extracts were dried (Na$_2$SO$_4$), filtered and concentrated in vacuo to give L-leucyl-O-methyl-L-tyrosine N-methylamide (5.2 g); m.p. 128°–132°; (Found: C, 60.04; H, 8.72; N, 12.26; C$_{17}$H$_{27}$N$_3$O$_3$ requires C, 60.16; H, 8.61; N, 12.38%); $\nu_{max}$ (CDCl$_3$) 3325 and 1655 cm$^{-1}$; $[\alpha]_D^{20}$ =10.2° (C=2.00, MeOH); δ(CD$_3$OD) 0.88 and 0.92 (each 3H, each d; 1.2–1.4 (1H, m, CH$_2$CH(CH$_3$)$_2$); 1.44–1.8 (2H, m, CHCH(CH$_3$)$_2$); 2.73 (3H, d, J=5 Hz, NCH$_3$); 2.82–3.3 (4H, m, NH$_2$, CH$_2$C$_6$H$_4$); 3.46 (1H, m, CH); 3.76 (3H, s, OCH$_3$); 4.58 (1H, q, dd, J=8 and 3 Hz, α-CH); 6.56 (1H, br, CONH); 6.82 (2H, d, J=8.6 Hz, Tyr H-3 and H-5); 7.13 (2H, d, J=8.6 Hz, Tyr H-2 and H-6); 7.96 (1H, d, J=8 Hz, CONH); m/e 322 (100% [m+1]$^+$).

(b) Methyl 5-N-(Benzyloxycarbonyl)amino-2-bromopentanoate

To a stirred solution of ε-Z-ornithine (53.2 g, 0.1M) in dilute H$_2$SO$_4$ (2.5N, 500 ml) at 0° was added KBr (60 g, 0.5M). To this solution was then added portionwise sodium nitrite (7.6 g, 0.11M) whilst the reaction temperature was maintained at 0° by the addition of ice. After stirring for 1 h at 0° the reaction mixture was allowed to warm to room temperature over 2 h. Diethyl ether (500 ml) was then added and the aqueous layer was re-extracted with diethylether (500,; ×3). The combined ethereal extracts, were washed with water and then brine, dried (MgSO$_4$), filtered and concentrated to an oil in vacuo.

To the crude bromo-acid (45 g, 0.136M) in dry methanol (300 ml) cooled to −30° was added dropwise thionyl chloride (33.7 ml, 0.405M) at such a rate that the temperature did not exceed −15°. The reaction mixture was warmed to 10° over 2 h and stirred at room temperature for 30 min. and then at 40° for 30 min. The resulting solution was then concentrated in vacuo, dissolved in CH$_2$Cl$_2$ and washed in turn with water, saturated aq. NaHCO$_3$ and water. The residue isolated from the organic layer was chromatographed on silica in 5% ethylacetate in CH$_2$Cl$_2$ to give the title compound as an oil (10.3 g), (Found: C, 48.61; H, 5.61; N, 4.00. $C_{14}H_{18}BrNO_4$ requires C, 48.85; H, 5.27; N, 4.07%); $\delta(CDCl_3)$ 1.5–1.8 and 1.9–2.2 (each 2H, each m, $CH_2CH_2$), 3.23 (2H, q, J=6 Hz, $NCH_2$), 3.77 (3H, s, $OCH_3$), 4.25 (1H, dd, J=7 and 14 Hz, α-CH), 4.8–4.9 (1H, broad s, NH), 5.10 (2H, s, $OCH_2$) and 7.35 (5H, broad s, $C_6H_5$).

EXAMPLE 9

N-[4-N-(Benzyloxycarbonyl)amino-1-(R)-carboxybutyl]-L-leucyl-O-methyl-L-tyrosine N-Methylamide To a solution of the ester (650 mg, 1.14M) from Example 8 in methanol/water (10:1, 11 ml) was added dilute NaOH (1N, 2.3 ml). The reaction mixture was stirred for 6 h at room temperature, acidified with acetic acid and then concentrated to a semi-solid in vacuo. This was partitioned between ethyl acetate and water and the resulting solid was filtered, washed with water and ethyl acetate and dried in vacuo to give the title compound (585 mg); m.p. 164°–169°; (Found: C, 61.59; H, 7.24; N, 9.40. $C_{30}H_{42}N_4O_7$ requires C, 61.21; H, 7.53; N, 9.52%); $\nu_{max}$ (Nujol) 3320, 1690 and 1645 cm$^{-1}$; $\delta(d^6DMSO)$ 0.85 (6H, m, $CH(CH_3)_2$); 0.96–1.8 (7H, m, $CH_2CH(CH_3)_2$, $NHCH_2CH_2CH_2$); 2.57 (3H, d, J=5 Hz, $NCH_3$); 2.5–3.2 (6H, m, $NHCH_2$, $CH_2C_6H_4$, α-CH×2); 3.70 (3H, s, $OCH_3$); 4.42 (1H, m, α-CH); 5.0 (2H, s, $CH_2C_6H_5$); 6.78 (2H, d, J=8.6 Hz, Tyr H-3 and H-5); 7.10 (2H, d, J=8.6 Hz, Tyr H-2 and H-6); 7.20 (1H, m, CONH); 7.35 (5H, m, $C_6H_5$); 7.88 (1H, m, CONH); 8.18 (1H, m, CONH).

EXAMPLE 10

N-[4-N-[N-(Acetyl)-L-prolyl-L-leucyl]amino-1-(R)-carboxy butyl]-L-leucyl-O-methyl-L-tyrosine N-methylamide This was synthesised from Z-proline, leucine methyl ester and N-[4-N-(benzyloxycarbonyl)amino-1-(R)-methoxycarbonylbutyl]-L-leucyl-O-methyl-L-tyrosine N-methylamide as described in the following paragraphs:

(a) N-(Benzyloxycarbonyl)-L-prolyl-L-leucine Ethyl Ester

To a stirred solution of Z-L-proline (12.7 g, 0.051M) in $CH_2Cl_2$ (200 ml) cooled to 0° was added 1-hydroxy benzotriazole (7.0 g) followed by a solution of DCC (10.6 g) in $CH_2Cl_2$ (50 ml). After 30 min. at 0° L-leucine ethyl ester (10.0 g, 0.051 molM) was added followed by triethylamine (15 ml) and the reaction mixture was then left to stir and warm up to room temperature overnight. The reaction mixture was then filtered and washed in turn with saturated aq. $NaHCO_3$ (250 ml×3), $H_2O$ (250 ml), dilute aq. HCl (1 M, 250 ml×3) and water (250 ml×2). The organic layer was dried ($Na_2SO_4$), filtered and concentrated in vacuo to an oil which subsequently crystallised. Recrystallisation from ethyl acetate/hexane gave N-(benzyloxycarbonyl)-L-prolyl-L-leucine ethyl ester as a white crystalline solid, 15.5 g, (78%); m.p. 67°–68°; (Found: C, 64.55; H, 7.79; N, 7.22. $C_{21}H_{30}N_2O_5$ requires C, 64.61; H, 7.74; N, 7.17%); $\nu_{max}$ ($CHCl_3$) 1740 and 1680 cm$^{-1}$; $\delta(CDCl_3)$ 0.7–0.95 (6H, m, $CH(CH_3)_2$); 1.18 (3H, m, $OCH_2CH_3$); 1.3–1.95 and 2.05–2.25 (7H, m, $CH_2CH_2$, $CH_2CH(CH_3)_2$); 3.4 (2H, m, $CH_2N$); 4.05 (2H, m, $OCH_2CH_3$); 4.25 (2H, m, α-CH); 4.98 and 5.05 (together 2H, respectively q, J=7 Hz, and m, $CH_2C_6H_5$); 7.35 (5H, broad s, $C_6H_5$) and 8.26 (1H, m, CONH); m/e 391 (100%, [m+1]$^+$).

(b) N-Acetyl-L-proline-L-leucine Ethyl Ester

To a solution of N-(benzyloxycarbonyl)-L-prolyl-L-leucine ethyl ester (7.5 g, 0.02 mM) in methanol (100 ml) was added acetic acid and 10% Pd/C (0.8 g). After stirring under hydrogen for 3 h at room temperature the reaction was filtered and concentrated to an oil in vacuo. Trituation of the residue with ether and recrystallisation from ethyl acetate/hexane gave L-prolyl-L-leucyl ethyl ester as the acetate salt (5.0 g), m.p. 87°–89°. $\nu_{max}$ 1760 and 1660 cm$^{-1}$; $\delta(CDCl_3)$ 0.94 (6H, m, $CH(CH_3)_2$); 1.27 (3H, t, J=7 Hz, $OCH_2CH_3$); 1.45–2.35 (7H, m, $CH_2CH_2$, $CH_2CH(CH_3)_2$); 2.2 (3H, s, $CH_3CO_2$); 3.1 (2H, m, $CH_2N$); 4.15 (1H, m, α-CH); 4.19 (2H, q, J=7 Hz, $OCH_2CH_3$); 4.55 (1H, m, α-CH); 7.24 (2H, br, NH, $CO_2H$); 7.87 (1H, d, J=7 Hz, CONH); m/e (100% [m+1]$^+$)].

To a solution of the foregoing amine (3.0 g, 11.7 mM) in $CH_2Cl_2$ (50 ml) was added p-nitrophenylacetate (2 g, 12MM). After stirring the reaction mixture at room temperature for 3 days it was diluted with $CH_2Cl_2$ (350 ml), washed with water, dried ($Na_2SO_4$) and concentrated to an oil in vacuo. Chromatography on silica in 1:1 $CH_2Cl_2$/EtOAc followed by 9:1 $CH_2Cl_2$/MeOH yielded N-acetyl-L-prolyl-L-leucine ethyl ester as a pale yellow oil (2.2 g); (Found [m+1]$^+$=299.19704. $C_{15}H_{27}N_2O_4$ requires [m+1]$^+$=299.19707); $\gamma_{max}$ ($CHCl_3$) 3600–3100 (broad), 1735, 1675 and 1625 cm$^{-1}$; $\delta(CDCl_3)$ 0.95 (6H, m, $CH(CH_3)_2$); 1.25 (3H, t, J=7 Hz, $OCH_2CH_3$); 1.44–2.5 (7H, m, $CH_2CH_2$, $CH_2CH(CH_3)_2$); 2.12 (3H, s, $CH_3CO$); 3.36–3.7 (2H, m, $CH_2N$); 4.18 (2H, t, J=7 Hz, $OCH_2CH_3$); 4.25–4.55 (1H, m, CH Pro); 4.6 (1H, CH Leu); 6.38 and 7.35 (1H, each d, J=7 Hz, CONH).

(c) N-[4-N-[N-(Acetyl)-L-prolyl-L-leucyl]amino-1-(R)-methoxycarbonylbutyl]-L-leucyl-O-methyl-L-tyrosine N-methylamide To a solution of N-[4-N-(benzyloxycarbonyl)amino-1-(R)-methoxycarbonylbutyl]-L-leucyl-O-methyl-L-tyrosine N-Methylamide (570 mg, 0.97 mM) in methanol (8 ml) was added 10% Pd/C and dilute HCl (1M, 2 ml). After stirring the reaction mixture under hydrogen for 2 h at room temperature it was filtered and concentrated in vacuo to a solid, (490 mg) (100%), which was used as such in the next step.

N-Acetyl-L-prolyl-L-leucine (271 mg, 1.06MM; obtained from the foregoing ethyl ester by hydrolysis in methanol with one equivalent of 1N-sodium hydroxide solution at 20° over 16 h followed by neutralisation with dilute HCl) in $CH_2Cl_2$ (2 ml) and DMF (2 ml) was stirred at 0° and 1-hydroxy benzotriazole (162 mg, 1.06 mM) and N-ethyl-N'-(dimethylaminopropyl)carbodiimide hydrochloride (240 mg, 1.06 mM) were then added. After 5 min N-methylmorphine (107 mg, 1.06 mM) was added followed, after 15 min, by the amine hydrochloride (prepared above) (485 mg, 0.96 mM). After stirring overnight at 0°–4°, the reaction mixture was concentrated in vacuo, dissolved in $CH_2Cl_2$ and washed in turn with water, saturated aq. $NaHCO_3$ and dilute HCl. The acid layer was separated, neutralised with $NaHCO_3$ and extracted with $CH_2Cl_2$. The organic extracts were dried, ($Na_2SO_4$) and evaporated in vacuo to yield the title compound as a foam (570 mg); m.p. 68°–72°; (Found: C, 59.99; H, 8.35; N, 11.65. $C_{36}H_{56}N_6O_8 \cdot 1H_2O$ requires C, 59.98; H, ;b 8.39; N, 11.66;1 %); $\delta(d^6 DMSO)$ 0.82 (12H, m, $CH(CH_3)_2$×2); 1.0–2.34 (14H, m, $CH_2CH_2$×2, $CH_2CH(CH_3)_2$×2); 1.98 and 2.0 (together 3H, each s, $CH_3CO$); 2.50–3.08 (8H, m, $CH_2C_6H_4$, $CH_2N$×2 and 2×α-CH); 2.56 (3H, d, J=5 Hz, $CH_3N$); 3.54 (3H, s, $OCH_3$); 3.70 (3H, s, OCH$_3$); 4.0–4.5 (3H, m, α-CH); 6.78 (2H, d, J=8 Hz Tyr H-3 and H-5); 7.11 (2H, d, J=8.6 Hz, Tyr H-2 and H-6); 7.5–8.35 (4H, m, CONH).

(d) N-[4-N-[N-(Acetyl)-L-prolyl-L-leucyl]amino-1-(R)-carboxybutyl]-L-leucyl-O-methyl-L-tyrosine N-Methylamide To a solution of the preceeding ester (380 mg, 0.54 mM) in methanol (5 ml) was added dilute NaOH (1M, 1 ml). After stirring overnight at room temperature, the reaction mixture was neutralised with acetic acid and concentrated in vacuo. Chromatography on reverse phase silica in 1:1 MeOH/H$_2$O gave the title compound (280 mg); m.p. 97°–101°; (Found: C, 58.52; H, 7.93; N, 11.46. C$_{36}$H$_{56}$N$_6$O$_8$.1.5H$_2$O requires C, 58.72; H, 8.31; N, 11.74%). $\nu_{max}$ (Nujol) 3700–3140 (broad) and 1635 cm$^{-1}$; δ(CD$_3$OD) 0.9 (12H, M, 2×CH(CH$_3$)$_2$); 1.4–2.25 (14H, M, 2×CH$_2$CH$_2$, 2×CH$_2$CH(CH$_3$)$_2$); 1.98 and 2.0 (together 3H, each s, CH$_3$CO); 2.68 and 2.72 (together 3H, each s, CH$_3$N), 2.75–3.8 (8H, m, CH$_2$C$_6$H$_5$, CH$_2$N×2, 2×CH); 3.75 (3H, s, OCH$_3$); 4.25–4.65 (3H, m, αCH), 6.78 (2H, d, J=8.6 Hz, Tyr H-3 and H-5); 7.11 (2H, d, J=8.6 Hz, Tyr H-2 and H-6).

EXAMPLE 11

N-[3-N-(Benzyloxycarbonyl)amino-1-(R)-carboxypropyl]-L-leucyl-O-methyl-L-tyrosine N-Methylamide This was prepared in two stages from methyl 4-N-(benzyloxycarbonyl)amino-2-bromo-butanoate and L-leucyl-O-methyl-L-tyrosine N-methylamide as described below:

(a) N-[3-N-(Benzyloxycarbonyl)amino-1-(R)-methoxycarbonyl propyl]-L-leucyl-O-methyl-L-tyrosine N-Methylamide Methyl 4-N-(benzyloxycarbonyl)amino-2-bromobutanoate (30 g), L-leucyl-O-methyl-L-tyrosine N-methylamide (30 g) and N-methyl morpholine (9.4 g) in acetonitrile (250 ml) was stirred and heated under reflux overnight. A further portion of the amine (1.1 g) was then added and the solution was heated under reflux for a further 4 h. The reaction mixture was then concentrated in vacuo, dissolved in chloroform and the solution washed with saturated aq. sodium bicarbonate solution. The material isolated from the organic layer was chromatographed on silica with ethyl acetate as eluant to yield N-[3-N-(Benzyloxycarbonyl)amino-1-(R)-methoxycarbonylpropyl]-L-leucyl-O-methyl-L-tyrosine N-methylamide (11.7 g); (Found: C, 63.09; H, 7.46; N, 9.59. C$_{30}$H$_{42}$N$_4$O$_7$ requires C, 63.16; H, 7.37; N. 9.83%); $\nu_{max}$ (CHCl$_3$) 3400, 1720 and 1660 cm$^{-1}$; δ(CDCl$_3$) 0.86 (6H, m, CH(CH$_3$)$_2$); 1.2–2.1 (6H, m, NHCH$_2$CH$_2$CH, CH$_2$CH(CH$_3$)$_2$, NH); 2.77 (3H, d, J=5 Hz, NCH$_3$); 2.95–3.45 (5H, m, NHCH$_2$, CH$_2$C$_6$H$_4$, αCH); 3.66 and 3.76 (each 3H, each s, 2×OCH$_3$); 3.8 and 4.61 (each 1H, each m, 2×CH); 5.10 (2H, m, CH$_2$C$_6$H$_5$); 5.21 (1H, m, OCONH); 672 (1H, m, CONH); 6.81 (2H, d, J=8.6 Hz, Tyr H-3 and H-5); 7.12 (2H, d, J=8.6 Hz, Tyr H-2 and H-6); 7.35 (5H, s, C$_6$H$_5$); 7.55 (1H, d, J=8 Hz, CONH); m/e 571 (100% [m+1]$^+$).

The methyl 4-N-(benzyloxycarbonyl)amino-2-bromobutanoate required in this preparation was made from L-glutamic acid as described in the following paragraphs:

L-Glutamic acid (105 g, 0.713M) was dissolved in concentrated sulphuric acid (300 ml) and to this was added chloroform (300 ml). To the stirred bi-phasic mixture at 0° was added portionwise over 30 min. sodium azide (60 g, 0.9 mole). The reaction mixture was stirred at 5°–10° for 30 min. and was then allowed to slowly warm to room temperature. The reaction mixture was then slowly heated to 80° for one hour the reaction was cooled, poured into water (1.5 l) and the aqueous layer was separated. The aqueous extract was diluted (to 20 liters) and was then applied to Dowex 50WX8, 16–40 mesh, H$^+$ resin. The column was washed with water and then with 1:1 880 Ammonia/Water and the fractions containing the product were lyophilised.

The crude product obtained above was dissolved in water (1 liter) and to this was added basic copper carbonate (100 g). The stirred mixture was heated under reflux for 40 min. and the hot solution was filtered. The solution was cooled to 35° and NaHCO$_3$ (60 g) and CHCl$_3$ (300 ml) were added. After stirring for 30 min. at room temperature, benzyloxycarbonyl chloride (75 ml) was added and the mixture was then allowed to stir at room temperature overnight. A further portion of benzyloxycarbonyl chloride (30 ml) was then added and stirring was continued for a further 24 h. The crystalline copper complex which had precipitated was then filtered, washed with water and added to a solution of EDTA (di Na salt) (120 g) in water (1.5 liter). The resulting mixture was stirred and heated under reflux for 3 h and was then cooled to 5°. After 40 h at 5° the crystalline product was collected by filtration, washed with water and acetone and dried in vacuo at 45°.

The 4-Z-diamino-butyric acid from above (120 g) was suspended in a mixture of dilute sulphuric acid (1M, 600 ml), water (200 ml) and potassium bromide (240 g). Sufficient water (200 ml) was then added to form a single phase. To the resulting solution stirred at −7° to −9°, was added a solution of sodium nitrite (44 g) in H$_2$O dropwise over 1 h. After 30 min at −7°, the mixture was warmed to room temperature over 1 h. Diethyl ether (1.5 liters) was added and the separated aqueous layer was washed with a further portion of ether. The dried ethereal extracts were concentrated in vacuo and the residue in methanol (1 liter) was cooled to 0° and treated dropwise with thionyl chloride (65 ml). The reaction was then concentrated in vacuo and the residue was partitioned between diethyl ether and saturated aq. sodium bicarbonate. The material isolated from the ether was chromatographed on silica eluting with a gradient of ethyl acetate in hexane to give methyl 4-N-(benzyloxycarbonyl)amino-2-bromo-butanoate (90 g) as an oil which crystallised on standing, m.p. 46°–50°; (Found: C,47.17; H,5.01; N,4.16. C$_{13}$H$_{16}$BrNO$_4$ requires C,47.29; H,4.88; N,4.24%); δ (CDCl$_3$) 2.08–2.45 (2H,m,CH$_2$); 3.37 (2H,m,NHCH$_2$); 3.76 (3H,s,OCH$_3$); 4.32 (1H,dd,J=10 Hz and 6 Hz, CH); 4.97 (1H,broad s, OCONH); 5.09 (2H,s,OCH$_2$) and 7.34 (5H,s,C$_6$H$_5$).

(b) N-[3-N-(Benzyloxycarbonyl)amino-1-(R)-carboxypropyl]-L-leucyl-O-methyl-L-tyrosine N-Methylamide To a solution of the preceeding ester (171 mg, 0.3 mM) in methanol (10 ml) stirred at 0° was added dilute NaOH (1N, 0.6 ml). After stirring overnight at 0° a further portion of NaOH (1N, 0.3 ml) was added and the solution was then stirred for 6 h at room temperature. The reaction mixture was then acidified with acetic acid and concentrated to a solid in vacuo. Recrystallisation of this material from methanol/H$_2$O gave the title compound (150 mg); m.p. 170°–172°; (Found: C,60.97; H,7.11; N,9.68. C$_{29}$H$_{40}$N$_4$O$_7$+0.8H$_2$O requires C,60.99; H,7.34; N,9.81%); $\nu_{max}$ (Nujol) 3330, 1690 and 1640 cm$^{-1}$; δ(CD$_3$OD) 0.88 (6H,dd,J=14 Hz and 7 Hz, CH(CH$_3$)$_2$); 1.2-1.95 (5H,m,NHCH$_2$CH$_2$, CH$_2$CH(CH$_3$)$_2$); 2.69 (3H,s,NCH$_3$); 2.75-3.65 (6H,m,NHCH$_2$, CH$_2$C$_6$H$_4$, and α-CH×2); 3.74 (3H,s,OCH$_3$); 4.54 (1H,dd,J=10 Hz and 6 Hz, α-CH); 5.08 (2H,m,CH$_2$C$_6$H$_5$); 6.82 (2H,d,J=8.6 Hz, Tyr H-3 and H-5); 7.12 (2H,d,J=8.6 Hz, Tyr H-2 and H-6); 7.35 (5H,m,C$_6$H$_5$).

EXAMPLE 12

N-[3-N-(Benzyloxycarbonyl)amino-1-(R)-methoxycarbonylpropyl]-L-leucyl-O-methyl-L-tyrosine N-Methylamide To a solution of N-(Tertiarybutoxycarbonyl)-L-leucyl-O-methyl-L-tyrosyl N-methylamide (4.2 g, 0.01M) in CH$_2$Cl$_2$ (5 ml) at 18° was added trifluoroacetic acid (8 ml). After stirring for 2 h at room temperature the reaction was concentrated in vacuo and was then trituated with dry ether to yield a gum. This was taken up in methanol (25 ml), methyl 4-N-(benzyloxycarbonyl)amino-2-oxo-butanoate (4.0 g; 0.015M; Synthesis, (1982), 41) was added and the pH of the solution adjusted to 6.5 with triethylamine. To this solution stirred at 0° was added sodium cyanoborohydride (400 mg) portionwise whilst the pH was periodically re-adjusted to 6.5 by the addition of acetic acid. After 1 h further sodium cyanoborohydride (400 mg) was added and the reaction was stirred overnight at room temperature. After concentration in vacuo the residue was partitioned between CH$_2$Cl$_2$ (100 ml) and water (50 ml). The CH$_2$Cl$_2$ layer was separated, washed in turn with dilute HCl (1M, 20 ml), water (25 ml), saturated sodium bicarbonate solution (2×30 ml), dried and evaporated to an oil. Chromatography on silica in CH$_2$Cl$_2$ in an increasing ethyl acetate gradient gave the title compound as a foam (1.0 g) which had physical data identical to that given above in Example 11.

EXAMPLE 13

N-[3-Amino-1-(R)-carboxypropyl]-L-leucyl-O-methyl-L-tryosine N-Methylamide

The acid (320 mg, 0.56 mM) from Example 11 in methanol (10 ml) was treated with dilute HCl (1M, 1 ml). This solution was hydrogenated over 10% palladium on charcoal (60 mg) for 90 min. at room temperature, filtered and then concentrated in vacuo to give the title compound as its dihydrochloride salt; m.p. 149°-152° (from CH$_2$Cl$_2$-ether); (Found: C,48.17; H,6.98; N,10.49. C$_{21}$H$_{34}$N$_4$O$_5$.2HCl+0.5 CH$_2$Cl$_2$ requires C,48.01; H,6.93; N,10.42%); ν$_{max}$ (Nujol) 3650-2400 (br), 1730 and 1650 cm$^{-1}$; δ(CD$_3$OD) 0.92 and 0.95 (each 3H, each d, each J=15 Hz,CH(CH$_3$)$_2$); 1.45-1.90 (3H,m,CH$_2$CH(CH$_3$)$_2$); 2.25 (2H,m,NHCH$_2$CH$_2$); 2.68 (3H,s,OCH$_3$); 3.04 (4H,m,NHCH$_2$ and CH$_2$C$_6$H$_4$); 3.58 (1H,dd,J=8 Hz and 6 Hz,α-CH); 3.77 (3H,s,OCH$_3$); 3.94 (1H,dd,J=8 Hz and 4 Hz,α-CH); 4.64 (1H,dd,J=13 Hz and 6 Hz,α-CH); 6.88 (2H,d,J=8.6 Hz, Tyr H-3 and H-5) and 7.10 (2H,d,J=8.6 Hz, Tyr H-2 and H-6).

EXAMPLE 14

N-[3-N-(p-Nitrobenzyloxycarbonyl)amino-1-(R)-carboxypropyl]-L-leucyl-O-methyl-L-tyrosine N-Methylamide (a) N-[3-N-(p-Nitrobenzyloxycarbonyl)amino-1-(R)-methoxycarbonylpropyl]-L-leucyl-O-methyl-L-tyrosine N-Methylamide A solution of N-[3-N-(benzyloxycarbonyl)amino-1-(R)-methoxycarbonyl propyl]-L-leucyl-O-methyl-L-tyrosine N-methylamide (1.24 g, mM) in methanol (25 ml) containing ethereal HCl (1 ml of a 2.6M solution) was hydrogenated over 10% palladised charcoal (0.3 g) for 6 h at 20°. The solution was filtered and concentrated in vacuo to give N-[3-N-amino-1-(R)-methoxycarbonylpropyl]-L-leucyl-O-methyl-L-tyrosine N-methylamide dihydrochloride as a foam (1.2 g) which was used in the next step without further purification.

To a suspension of N-[3-N-amino-1-(R)-methoxycarbonylpropyl]-L-leucyl-O-methyl-L-tyrosine N-methylamide dihydrochloride (400 mg, 0.808 mM) in dry CH$_2$Cl$_2$ (6 ml) cooled in an ice bath, was added p-nitrobenzyloxycarbonyl chloride (400 mg) in dry CH$_2$Cl$_2$. To this was then added dropwise a solution of N-methyl morpholine (270 mg, 2.67 mM) in dry CH$_2$Cl$_2$ (2 ml). After 30 min at 0°, a further portion of p-nitrobenzyloxycarbonyl chloride (400 mg) in dry CH$_2$Cl$_2$ (1 ml) was added followed by a solution of NMM (100 mg) in dry CH$_2$Cl$_2$ (1 ml). After a further 0.5 h at 0° the reaction mixture was diluted with CH$_2$Cl$_2$ (20 ml), washed in turn with water (20 ml), aq. citric acid solution (20 ml) and saturated aq. NaHCO$_3$-(20 ml). The organic extract was concentrated in vacuo and purified by chromatography on silica eluting with CH$_2$Cl$_2$ in a rapidly increasing ethyl acetate gradient to give the title compound as a foam (450 mg, 90%); (Found: [m+1]$^+$=616.3012. C$_{30}$H$_{42}$N$_5$O$_9$ requires [m+1]$^+$=616.2983); $_{max}$ (CHCl$_3$) 3380, 1742 and 1660 cm$^{-1}$; m/e 616 (5% [m+1]$^+$); 153 (100% [O$_2$NC$_6$H$_4$CH$_2$OH]$^+$). δ(CDCl$_3$) 0.87 (6H,m,CH(CH$_3$)$_2$); 1.1-2.0 (5H,m,NHCH$_2$CH$_2$, CH$_2$CH(CH$_3$)$_2$,NH) 2.76 (3H,d,J=5 Hz,NCH$_3$); 2.9-3.5 (6H,m,NHCH$_2$,CH$_2$C$_6$H$_4$,α-CH×2) 3.68 and 3.77 (each 3H, each s, 2×OCH$_3$); 4.60 (1H,dd,J=13 Hz and 6 Hz,α-CH); 5.10 (2H,s,CH$_2$C$_6$H$_4$NO$_2$); 5.45 (1H,m,OCONH); 6.50 (1H, broad s, OCONH); 6.82 (2H,d,J=8.6 Hz, Tyr H-3 and H-5); 7.11 (2H,d,J=8.6 Hz, Tyr H-2 and H-6); 7.45 (1H,d,J=8 Hz, CONH); 7.52 (2H,d,J=9 Hz, benzoyl H-2 and H-6); 8.21 (2H,d, J=9 Hz, benzoyl H-3 and H-5).

(b) N-[3-N-(p-Nitrobenzyloxycarbonyl)amino-1-(R)-carboxypropyl]-L-leucyl-O-methyl-L-tyrosine N-methylamide To a solution of the preceeding ester (360 mg, 0.58 mM) in methanol (6 ml) at 0° was added dilute NaOH (1N, 1.2 ml). After standing at 0° for 48 h, the solution was acidified with acetic acid and concentrated to a solid in vacuo. Trituration with ethyl acetate and water gave the title compound (56 mg); m.p. 167°-170°; (Found: C,56.56; H,6.58; N,11.21. C$_{29}$H$_{39}$N$_5$O$_9$+0.8-H$_2$O requires C,56.54; H,6.64; N,11.37%); ν$_{max}$ (Nujol) 3250, 1690 and 1642 cm$^{-1}$; δ(d$^6$DMSO) 0.8 (6H,m,CH(CH$_3$)$_2$; 1.1-2.0 (5H,m,NHCH$_2$CH$_2$, CH$_2$CH(CH$_3$)$_2$); 2.57 (3H,d,J=5 Hz,NCH$_3$); 2.62-3.85 (7H,m,NCH$_2$, α-CH×2, CH$_2$C$_6$H$_4$, OH); 3.67 (3H,s,OCH$_3$); 4.43 (1H,m,α-CH); 5.10 (2H,s,OCH$_2$); 6.78 (2H,d,J=8.6 Hz, Tyr H-3 and H-5); 7.13

(2H,d,J=8.6 Hz, Tyr H-2 and H-6); 7.95 (1H,m,CONH); 8.07 (2H,d,J=8.6 Hz, Benzoyl H-2 and H-6); 8.25 (1H,m,CONH); 8.31 (2H,d,J=8.6 Hz, Benzoyl H-3 and H-5); 9.12 (1H,m,CONH).

EXAMPLE 15

N-[3-N-(Benzoyl)amino-1-(R)-carboxy-propyl]-L-leucyl-L-tyrosine N-Methylamide

This was prepared in two steps from N-[3-N-amino-1-(R)-methoxycarbonylpropyl]-L-leucyl-O-methyl-L-tyrosine N-methylamide as described below:

(a) N-[3-N-(Benzoyl)amino-1-(R)-methoxycarbonylpropyl]-L-leucyl-L-tyrosine N-Methylamide To a stirred suspension of N-[3-N-amino-1-(R)-methoxycarbonylpropyl]-L-leucyl-O-methyl-L-tyrosine N-methylamide dihydrochloride (539 mg, 1 mM) and benzoyl chloride (186 mg, 1 mM) in dry $CH_2Cl_2$ (30 ml) at 0° was added dropwise N-methyl morphline (439 mg, 4.3 mM). The reaction mixture was then stirred overnight, concentrated in vacuo and chromatographed on silica eluting with ethyl acetate in an ethyl acetate/methanol gradient to yield the title compound (350 mg); m.p. 145°–148°; (Found: C,63.97; H,7.38; N,10.20. $C_{29}H_{40}N_4O_6+0.2H_2O$ requires C,64.00; H,7.48; N,10.29%). $\delta(CDCl_3)$ 0.85 and 0.86 (each 3H, each d, each J=6.5 Hz, $CH(CH_3)_2$); 1.18–1.80 (4H,m,$NHCH_2CH_2CH$ and $CH_2CH(CH_3)_2,NH$); 2.0 (2H,dd,J=13 and 6 Hz, $CH_2CH(CH_3)_2$); 2.75 (3H,d,J=5 Hz,$NCH_3$); 3.06 and 3.4–3.7 (6H,m,$NHCH_2$, $CH_2C_6H_4$ and α-CH×2); 3.64 and 3.74 (each 3H, each s, 2×$OCH_3$) 4.60 (1H,dd,J=15 Hz and 6 Hz,α-CH); 6.5 and 6.75 (each 1H, each m, 2×CONH); 6.82 (2H,d,J=8.6 Hz, Tyr H-3 and H-5); 7.15 (2H,d,J=8.6 Hz, Tyr H-2 and H-6); 7.5 (5H,m,$C_6H_4$) and 7.77 (1H,d,J=8 Hz,CONH).

(b) N-[3-N-(Benzoyl)amino-1-(R)-carboxypropyl]-L-leucyl-L-tyrosine N-Methylamide To the preceeding ester (150 mg, 0.27 mM) in methanol (10 ml) was added dilute NaOH (1N, 1 ml) and the solution was then stirred at room temperature for 3 days. The reaction mixture was acidified with acetic acid and was concentrated in vacuo. Recrystallisation of the residue from methanol-$H_2O$ gave the title compound (110 mg); m.p. 175°–177°; (Found: C,61.41; H,7.71; N,10.17. $C_{28}H_{38}N_4O_6+1.2H_2O$ requires C,61.34; H,7.34; N,10.22%); $\nu$max (Nujol) 3320 and 1640 cm$^{-1}$; $\delta(d^6DMSO)$ 0.82 (6H,m,$CH(CH_3)_2$); 1.05–2.0 (5H,m,$NHCH_2CH_2,CH(CH_3)_2$); 2.58 (3H,d,J=5 Hz,$NCH_3$); 3.65–4.55 (6H,m,$NHCH_2$),$CH_2C_6H_4$ and α-CH×2);3.68 (3H,s,$OCH_3$); 4.42 (1H,m,α-CH); 6.78 (2H,d,J=8.6 Hz, Tyr H-3 and H-5); 7.11 (2H,d,J=8.6 Hz, Tyr H-2 and H-6); 7.46 (3H,m,CONH and 2 protons from $C_6H_5$); 7.86 (3H,m, 3 protons from $C_6H_5$); 8.20 (2H,d,J=8 Hz,CONH); 8.51 (1H,m,CONH).

EXAMPLE 16

N-[3-N-(P-Nitrobenzoyl)amino-1-(R)-carboxypropyl]-L-leucyl-O-methyl-L-tyrosine. N-Methylamide This was prepared exactly as described for the N-benzoyl derivative in Example 15 except that p-nitrobenzoyl chloride was used in place of benzoyl chloride in the first step. After hydrolysis of the intermediate ester, the resulting solid was recrystallised from methanol-water to give the title compound, (450 mg); m.p. 170°–180°; (Found: C,57.38; H,6.82; N,11.86. $C_{28}H_{37}N_5O_8+0.8H_2O$ requires C,57.39; H,6.64; N,11.95%; $\nu$max (Nujol) 3340 and 1645 cm$^{-1}$; $\delta(d^6DMSO)$ 0.82 (6H,m,$CH(CH_3)_2$; 1.05–2.05 (5H,m,$NCH_2CH_2CH$, $CH_2CH(CH_3)_2$)); 2.58 (3H,m,$NCH_3$); 2.6–3.65 (6H,m,$NHCH_2$α-CH×2 and $CH_2C_6H_4$); 3.7 (3H,m,$OCH_3$); 4.45 (1H,m,α-CH); 6.8 (2H,d,J=8.6 Hz, Tyr H-3 and H-5); 7.12 (2H,d,J=8.6 Hz, Tyr H-2 and H-6); 7.88 (1H,m,CONH); 8.08 (2H,d,J=8 Hz, Benzoyl H-2 and H-6); 8.2 (1H,d,J=8 Hz,CONH); 8.33 (2H,d,J=8 Hz, Benzoyl H-3 and H-5) and 8.88 (1H,m,CONH).

EXAMPLE 17

N-[3-N-(p-Aminobenzoyl)amino-1-(R)-carboxypropyl]-L-leucyl-O-methyl-L-tyrosine N-Methylamide The acid (351 mg), from Example 16 was dissolved in methanol (25 ml) and to this solution was added 10% Pd/C (400 mg) and dilute ethereal HCl (2.6M, 2 ml). after stirring the reaction mixture under hydrogen for 2.5 h at room temperature it was filtered and concentrated in vacuo to yield the title compound as a foam (290 mg);

m.p. 155°–160°; (Found: C,50.39; H,6.68; N,10.23. $C_{28}H_{39}N_5O_6$ 3HCl+1H_2O requires C,50.26; H,6.62; N,10.46%); $\nu$max (Nujol) 3650–2120 (broad), 1730 and 1645 cm$^{-1}$; $\delta$ (d$^6$DMSO) 0.81 and 0.87 (each 3H, each s, $CH(CH_3)_2$); 1.3–1.8 (3H,m,$CH(CH_3)_2$); 2.05 (2H,m,$NHCH_2CH_2CH$); 2.58 (3H,d,$NCH_3$); 2.75 and 2.98 (together 2H, each m, $CH_2C_6H_4$); 3.2–3.5 (3H,m,$NHCH_2$ and α-CH); 3.7 (3H,s,$OCH_3$); 3.97 (1H,m,α-CH); 4.58 (1H,m,α-CH); 6.83 (2H,d,J=8.6 Hz, Tyr H-3 and H-5); 7.01 (2H,d,J=8 Hz, benzoyl H-3 and H-5); 7.10 (2H,d,J-6.8 Hz, Tyr H-2 and H-6); 7.81 (2H,d,J=8 Hz, benzoyl H-2 and H-6); 8.17 (1H,m,CONH); 8.67 (1H,m,CONH); 9.11 (1H,d,J=8 Hz,CONH) and 9.5 (3H,br,$NH_3$).

EXAMPLE 18

N-[3-(N'-Benzyl)carbamoyl-1-(R)-carboxypropyl]-L-leucyl-O-methyl-L-tyrosine N-Methylamide This was prepared according to the following steps:

(a) N-[3-(N'-Benzyl)carbamoyl-1-(R)-methoxycarbonylpropyl]-L-leucyl-O-methyl-L-tyrosine N-Methylamide To a stirred suspension of N-[3-N-amino-1-(R)-methoxy-carbonylpropyl]-L-leucyl-O-methyl-L-tyrosyl N-Methylamide dihydrochloride (406 mg, 0.78 mM) in dry $CH_2Cl_2$ (10 ml) at 0° was added benzyl isocyanate (104 μl, 1.56 mM). A solution of N-methyl morpholine (189 mg, 1.87 mM) in dry $CH_2Cl_2$ (5 ml) was then added dropwise over 5 min. After 30 min at 0°, a further portion of benzyl isocyanate (25 μl) was added and this was repeated after an additional 30 min. at 0°. The reaction mixture was then allowed to warm to room temperature over 3 h. Water (50 ml) and $CH_2Cl_2$ (50 ml) were then added and the material isolated from the organic extracts was chromatographed on silica in 5% MeOH in $CH_2Cl_2$ to afford the title compound (223 mg); 61°–69°; (Found: C,62.77; H,7.64; N,12.03. $C_{30}H_{43}N_5O_6+0.3$-$H_2O$ requires C,62.65; H,7.64; N,12.08%); $\delta(CDCl_3)$ 0.87 (6H,m,$CH(CH_3)_2$) 1.10–2.0 (6H,m,$NHCH_2CH_2,CH_2CH(CH_3)_2$ and NH) 2.64 (3H,d,J=5 Hz,$NCH_3$); 2.85–3.54 (6H,m,$NHCH_2$, $CH_2C_6H_4$ and α-CH×2); 3.67 and 3.78 (each 3H, each s, 2×$OCH_3$); 4.37 (2H,dd,15 Hz and 2 Hz,$CH_2C_6H_5$); 4.56 (1H,dd,J=13 Hz and 6 Hz,α-CH); 5.16, 5.42 and 6.44 (each 1H, each broad s, 3×CONH) 6.80 (2H,d,J=8.6 Hz, Tyr H-3 and H-5); 7.08 (2H,d,J=8.6

Hz, Tyr H-2 and H-6); 7.3 (5H,m,C$_6$H$_5$) and 7.7 (1H,d,J=8 Hz,CONH).

(b) N-[3-(N'-Benzyl)carbamoyl-1-(R)-carboxypropyl]-L-leucyl-O-methyl-L-tyrosine N-Methylamide To a solution of the preceeding ester (240 mg, 0.42 mM) in methanol (25 ml) at room temperature, was added dilute NaOH (1N, 1.5 ml). After standing overnight at room temperature the reaction mixture was acidified with acetic acid and concentrated in vacuo. Chromatography on reverse phase silica eluting with a methanol/H$_2$O gradient gave the title compound (107 mg); m.p. 104°-108°; (Found: C,60.88; H,7.44; N,12.12. C$_{29}$H$_{41}$N$_5$O$_6$H$_2$O requires C,60.71; H,7.55; N,12.20%); $\nu_{max}$ (Nujol) 3300 and 1640 cm$^{-1}$; δ(d$^6$DMSO) 0.8 (6H,m,CH(CH$_3$)$_2$) 0.95-1.85 (5H,m,NHCH$_2$CH$_2$ and CH$_2$CH(CH$_3$)$_2$); 2.2-3.4 (6H,m,NHCH$_2$, α-CH×2 and CH$_2$C$_6$H$_4$); 2.56 (3H,d,J=5 Hz, NHCH$_3$); 3.70 (3H,s,OCH$_3$); 4.22 (2H,m,CH$_2$C$_6$H$_5$); 4.45 (1H,m,α-CH); 6.0 and 6.42 (each 1H, each m, 2×CONH); 6.82 (2H,d,J=8.6 Hz, Tyr H-3 and H-5); 7.12 (1H,d,J=8.6 Hz, Tyr H-2 and H-6); 7.28 (5H,m,C$_6$H$_5$); 7.94 (1H,m,CONH) and 8.25 (1H,d,J=Hz,CONH).

EXAMPLE 19

N-[3-N-(Benzyloxycarbonyl)amino-1-(R)-carboxypropyl]-L-leucine N-Phenethylamide

N-(Tertiarybutoxycarbonyl)-L-leucine (10 g, 0.04M in a mixture of CH$_2$Cl$_2$ (100 ml) and DMF (10 ml) was cooled to 0°. to this was added 1-hydroxybenzotriazole (6.2 g, 0.04M) followed dropwise by a solution of DCC (8.2 g, 0.04 mole) in CH$_2$Cl$_2$. After 10 min. at 0° a solution of phenethylamine (4.84 g, 0.04M) in CH$_2$Cl$_2$ (15 ml) was added dropwise and the stirred solution was then allowed to warm to room temperature overnight. The reaction mixture was then filtered, concentrated in vacuo and dissolved in ethyl acetate (150 ml). The ethyl acetate solution was washed in turn with water (40 ml), saturated aq. NaHCO$_3$ (50 ml×2), aqueous citric acid (50 ml) and saturated aq. NaHCO$_3$ (50 ml). The residue after evaporation of the solvent was recrystallised from ethyl acetate/hexane to give N-(tertiarybutoxycarbonyl)-L-leucyl-N-phenethylamide as a white powder (9.6 g); m.p. 86°-88°; $\nu_{max}$ (CHCl$_3$) 3415 and 1670 cm$^{-1}$; δ (CDCl$_3$) 0.85 (6H,m,CH(CH$_3$)$_2$); 1.35 (9H,s,OC(CH$_3$)$_3$); 1.3-1.75 (3H,m,CH$_2$CH(CH$_3$)$_2$); 2.69 (2H,t,J=7.2 Hz, CH$_2$C$_6$H$_5$); 3.3-3.6 (2H,m,NCH$_2$); 4.05 (1H,m,α-CH); 4.9 (1H,m,OCONH); 6.2 (1H,m,CONH); 7.2-7.4 (5H,m,C$_6$H$_5$).

N-(tertiarybutoxycarbonyl)-L-leucine N-phenethylamide (6.17 g, mole) was dissolved in a 1:1 TFA/CH$_2$Cl$_2$ mixture (60 ml). After stirring for 6 h at 20° the reaction mixture was concentrated in vacuo and the residue in CH$_2$Cl$_2$ (50 ml) washed with saturated aq. NaHCO$_3$ (100 ml). The aqueous extract was back extracted with CH$_2$Cl$_2$ (50 ml×3) and the combined organic extracts concentrated to an oil in vacuo. The crude L-leucine N-phenethylamide so obtained was used as such in the next step.

To a solution of methyl 4-N-(benzyloxycarbonyl)amino-2-bromo-butanoate (330 mg, 1 mmole) in dry acetonitrile (10 ml) was added L-leucine N-phenethylamide (235 mg, 1 mM) and N-methyl morpholine (110 mg, 1 mM). The solution was heated at reflux overnight, sodium iodide (150 mg, 1 mM) was added and the reaction was reheated to reflux for a further 7 h. The reaction mixture was then filtered and concentrated to an oil in vacuo. Chromatography of the residue on silica in 1:1 EtOAc/Hexane gave N-[3-N-(benzyloxycarbonyl)amino-1-(R,S)-methoxycarbonylpropyl]-L-leucine N-phenethylamide (310 mg). Rechromatography on silica then gave the R diastereoisomer as an oil.

To a solution of the foregoing R-isomer (110 mg) in methanol (4 ml) was added dilute NaOH (1N, 0.5 ml). After standing overnight at 20° the reaction mixture was acidified with acetic acid and concentrated to a solid in vacuo. Chromatography on reverse phase silica eluting with 1:1 MeOH/H$_2$O gave the title compound as a white powder (55 mg), m.p. 130°-135°; (Found: C,65.62; H,7.59; N,8.85. C$_{28}$H$_{35}$N$_3$O$_5$+0.3H$_2$O requires C,65.75; H,7.55; N,8.85%); $\nu_{max}$ (Nujol) 1690, 1655 and 1630 cm$^{-1}$; δ(d$^6$DMSO) 0.83 (6H,m,CH(CH$_3$)$_2$); 1.1-1.85 (6H,m,NCH$_2$CH$_2$CH$_2$CH(CH$_3$)$_2$ and NH); 2.69 (2H,t,J=7.2 Hz,CH$_2$C$_6$H$_5$); 3.0-3.6 (7H,NCH$_2$×2,α-CH×2, CO$_2$H); 5.0 (2H,s,OCH$_2$C$_6$H$_5$); 7.1-7.5 (10H,m,C$_6$H$_5$×2); 8.05 (1H,m,CONH).

EXAMPLE 20

N-[5-N-(Benzyloxycarbonyl)amino-1-(R)-methoxycarbonyl pentyl)-L-leucyl-O-methyl-L-tyrosine N-Methylamide To a stirred solution of crude methyl 6-N-(benzyloxycarbonyl)amino-2-oxo-hexanoate (7.03 g, 24 mM; Tet.-Lett., (1982), 23, 1875) and L-leucyl-O-methyl-L-tyrosine N-Methylamide (1.86 g, 6 mM) in methanol (50 ml) was added acetic acid to bring the pH to 6.5. Sodium cyanoborohydride (400 mg, 6.5 mM) was then added portionwise whilst the pH of the solution was continually re-adjusted to 6.5 by the addition of acetic acid. After 1.5 h at room temperature a further portion of sodium cyanoborohydride (400 mg) was added and the pH was again re-adjusted to 6.5 with acetic acid. After a further 1 h at room temperature, the reaction mixture was concentrated in vacuo and the residue in CH$_2$Cl$_2$ (50 ml) was washed in turn with water (30 ml), dilute HCl (1M, 30 ml) and saturated aq.NaHCO$_3$. The material isolated from the organic layer was purified by column chromatography on silica in CH$_2$Cl$_2$ in an increasing ethyl acetate gradient to give the title compound as an oil (360 mg); (Found: [m+1]$^+$=xxx.xxxx. C$_{32}$H$_{44}$N$_4$O$_7$ requires [m+1]$^+$=xx.xxxx); δ (CDCl$_3$) 0.88 CH(CH$_3$)$_2$); 1.0-1.86 (10H,m,NHCH(CH$_2$)$_3$), CH$_2$CH(CH$_3$)$_2$ and NH); 2.74 (3H,d,J=5 Hz,NCH$_3$); 2.85-3.4 (6H,m,NHCH$_2$,CH$_2$C$_6$H$_4$ and α-CH×2); 3.65 and 3.75 (each 3H, each s, 2×OCH$_3$); 4.64 (1H,dd,J=13 Hz and 6 Hz, α-CH); 5.10 (2H,s,CH$_2$C$_6$H$_5$); 6.78 (2H,d,J=8.6 Hz, Tyr H-3 and H-5); 7.10 (2H,d,J=8.6 Hz, Tyr H-2 and H-6); 7.35 (5H,m,C$_6$H$_5$) and 7.64 (1H,d,J=10 Hz,CONH).

EXAMPLE 21

N-[5-N-(Benzyloxycarbonyl)amino-1-(R)-carboxypentyl]-L-leucyl-O-methyl-L-tyrosine N-Methylamide To a solution of the ester from Example 20 (140 mg, 0.23 mM) in methanol (10 ml) at 0° was added dilute NaOH (1N, 0.5 ml). After 48 h at 0°, a further portion of NaOH (1N, 0.4 ml) was added and the solution stirred at 20° for a further 24 h. The reaction mixture was then acidified with acetic acid and concentrated in vacuo to give a semi-solid which was purified by partition between ethyl acetate and water at 0°. The resulting solid was filtered, washed with water and ethyl acetate and was dried in vacuo to give the title compound (110 mg); 122°-128°; (Found: [m+1]$^+$=585.3290 C$_{31}$H$_{44}$N$_4$O$_7$ requires [m+1]+ =585.3288) $\nu_{max}$ (Nujol) 3340, 1688 and 1640 cm$^{-1}$; δ(CD$_3$OD) 0.88 (6H, m, CH(CH$_3$)$_2$); 1.0–1.86 (9H, m, NHCH$_2$(CH$_2$)$_3$ and CH$_2$CH(CH$_3$)$_2$); 2.74 (3H, s, NCH$_3$); 2.8–3.6 (6H, m, NHCH$_2$, CH$_2$C$_6$H$_4$ and α-CH×2); 3.77 (3H, s, OCH$_3$); 4.60 (1H, m, α-CH); 5.10 (2H, s, CH$_2$C$_6$H$_5$); 6.78 (2H, d, J=8.6 Hz, Tyr H-3 and H-5); 7.05 (1H, m, CONH); 7.10 (2H, d, J=8.6 Hz Tyr H-2 and H-6) and 7.35 (5H, m, C$_6$H$_5$); m/e 585 (1%, [m+1]+), 567 (20% [m+1−H$_2$O]+).

EXAMPLE 22

N-[5-N-[N-Acetyl-L-prolyl]amino-1-(R)-carboxypentyl]-L-leucyl-O-methyl-L-tyrosine N-Methylamide N-[5-N-(Benzyloxycarbonyl)amino-1-(R)-methoxycarbonylpentyl]-L-leucyl-O-methyl-L-tyrosine N-methylamide (400 mg, 0.66 mM) in methanol (20 ml) was treated with dilute HCl (1N, 1.2 ml) and PdCl$_2$ (50 mg). The reaction mixture was stirred under hydrogen for 20 min. at room temperature and was then filtered. Concentration of the resulting solution in vacuo gave N-[5-amino-1-(R)-methoxycarbonylpentyl]-L-leucyl-O-methyl-L-tyrosine N-methylamide hydrochloride as an oil. This was dissolved in CH$_2$Cl$_2$ (20 ml) and DMP (5 ml) and to the resulting solution was added N-methyl morpholine (300 mg) and N-acetyl-L-proline p-nitrophenyl ester (191 mg). After standing at 20° for 72 h, the reaction mixture was concentrated in vacuo and the residue in ethyl acetate (20 ml) was washed with aq. citric acid solution. These aqueous washings were concentrated in vacuo and the resultant oil was purified by chromatography on reverse phase silica eluting with a gradient of methanol in H$_2$O to give N-[5-N-(N-acetyl-L-prolyl)amino-1-(R)-methoxycarbonylpentyl]-L-leucyl-O-methyl-L-tyrosine N-methylamide (350 mg) δ(CDCl$_3$) 0.84 (6H, dd, J=14 Hz and 7 Hz, CH(CH$_3$)$_2$); 1.05–2.4 (13H, m, NHCH$_2$(CH$_2$)$_3$, CH$_2$CH(CH$_3$)$_2$ and CH$_2$CH$_2$); 2.08 (3H, s, COCH$_3$); 2.70 (3H, s, NCH$_3$); 2.76–3.82 (8H, m, NCH$_2$,NHCH$_2$C$_6$H$_4$ and α-CH×2); 3.66 and 3.74 (each 3H, each s, 2×OCH$_3$); 4.32 (1H, m,α-CH); 4.56 (1H, dd, J=13 Hz and 6 Hz, α-CH); 6.80 (2H, d, J=8.6 Hz, tyr H-3 and H-5) and 7.12 (2H, d, J=8.6 Hz, Tyr H-2 and H-6).]

A portion of this material (130 mg) in methanol (5 ml) was treated at 0° with dilute NaOH (1N, 0.5 ml). After standing overnight at room temperature, a further portion of NaOH was added (1N, 0.2 ml) and this was then repeated 6 h later. After a further 18 h at 20° the reaction mixture was acidified with acetic acid and concentrated to an oil in vacuo. Chromatography on reverse phase silica eluting with water in an increasing methanol gradient gave the title compound (100 mg); m.p. 97°–101°; (Found: [m+1]+ =590.3552C$_{30}$H$_{47}$N$_5$O$_7$ requires [m+1]+ =590.3554); $\nu_{max}$ (Nujol 3280 (br) and 1625 (br) cm$^{-1}$; δ(CD$_3$CD) 0.94 (6H, m, CH(CH$_3$)$_2$); 1.2–2.4 (13H, m, NHCH$_2$(CH$_2$)$_3$, CH$_2$CH(CH$_3$)$_2$ and CH$_2$CH$_2$); 2.12 (3H, s, COCH$_3$); 2.68 (3H, s, NCH$_3$); 2.75–4.1 (8H, m, NCH$_2$NHCH$_2$,CHHD 2C$_6$H$_4$ and α-CH×2); 3.77 (3H, s, OCH$_3$); 4.33 and 4.58 (each 1H, each m, 2×2CH); 6.85 (2H, d, J=8.6 Hz, Tyr H-3 and H-5); 7.16 (2H, d, J=8.6 Hz, Tyr H-2 and H-6) and 8.03 (1H, m, CONH); m/e 590 (2%, [m+1]+, 572 (10% [m+1−H$_2$O]+).

EXAMPLE 23

N-[2-(S)-N-(1-(R)-Carboxyethyl)amino-4,4-dimethylpentanoyl]-L-alanine N-Butylamide N-[2-(S)-N(1-(R)-Methoxycarbonylethyl)amino-4,4-dimethylpentanoyl]-L-alanine N-butylamide (65 mg) in methanol (30 ml) was treated with 1N-sodium hydroxide (3 ml) at 20° for 6 h. Excess acetic acid was then added and the solvent evaporated in vacuo. The residue was chromatographed on reverse phase silica (RF 18) in a gradient of 20%–80% methanol in water. Elution in 70% methanol in water afforded the title compound (30 mg) as a freeze-dried powder, m.p. 137°–138°; (Found: [m+1]+ =344.2548. C$_{17}$H$_{34}$N$_3$O$_4$ requires [m+1]+ =344.2549); δ(D$_2$O) 0.9 (3H, t, J=6 Hz, CH$_2$CH$_3$); 0.94 (9H, s, C(CH$_3$)$_3$); 1.2–1.8 (6H, m, (CH$_2$)$_2$ and CH$_2$); 1.4 (3H, d, J=8 Hz, CH$_3$); 1.52 (3H, d, J=7 Hz, CH$_3$); 3.18 (2H, t, J=6 Hz, NHCH$_2$); 3.66 (1H, q, J=5 Hz, CHCO); 3.88 (1H, d, J=10 Hz, CHCH$_2$) and 4.38 (1H, q, J=5 Hz, CHCH$_3$).

The starting material required in the preceeding preparation was synthesised as described in the following paragraphs:

(a) Benzyl 2-Bromo-4,4-dimethylpentanoate 4,4-Dimethylpentanoic acid (40 g; *Chem Lett,* (1980), 571) was treated at 20° for 16 h with thionyl chloride (40 g) and the mixture distilled under reduced pressure to yield 4,4-dimethylpentanoyl chloride (38 g) b.p. 52°–58° at 10 mm Hg; δ (CDCl$_3$) 0.94 (9H, s, C(CH$_3$)$_3$; 1.66 (2H, t, J=9 Hz, CH$_2$) and 2.88 (2H, t, J=9 Hz, CH$_2$CO).

A portion of this material (20 g) was treated at 110° with bromine (20 g) for 4 h. Further bromine (5 g) was then added and the reaction continued for 1 h. Distillation under reduced pressure afforded 2-bromo-4,4-dimethylpentanoyl chloride (26 g), b.p. 92°–96° at 10 mmHg; δ (CDCl$_3$) 1.0 (9H, s, C(CH$_3$)$_3$); 1.94 (1H, dd, J=15 and 5 Hz, CHCHBr); 2.42 (1H, dd, J=15 and 8 Hz, CHCHBr) and 4.64 (1H, dd, J=8 and 5 Hz, CHBr).

The bromo-acid chloride (12 g) in CH$_2$Cl$_2$ (100 ml) was treated with benzyl alcohol (8.8 g) and N-methyl morpholine (4.06 g) at 0° for 16 h. The solution was then washed successively with dilute HCl and Sat.aq.NaHCO$_3$ solution. The residue after evaporation of the solvent was purified by chromatography on silica in 20% ether-hexane to give the desired bromo ester (11.2 g) as an oil; (Found: C, 56.3; H,6.4; Br,26.8; C$_{14}$H$_{19}$Br,O requires C,56.2; H,6.4; Br,26.7%); $\nu_{max}$ 2940 and 1730 cm$^{-1}$ δ(CDCl$_3$) 0.88 (9H, s, (CH$_3$)$_3$C); 1.92 (1H, dd, J=15 and 4 Hz, CHCHBr); 2.38 (1H, dd, J=15 and 10 Hz, CHCHBr); 4.34 (1H, dd, J=10 and 4 Hz CHBr); 5.2 (2H, s, OCH$_2$-C$_6$H$_5$) and 7.4 (5H, m, C$_6$H$_5$).

(b) Benzyl 2-(S)-N-(1-(R)-Methoxycarbonylethyl)amino-4,4-dimethylpentanoate

Benzyl-2-bromo-4,4-dimethylpentanoate (20 g) in dry dimethyl sulphoxide (250 ml) was treated with D-alanine methylester hydrochloride (9.33 g), N-methyl morpholine (6.78 g) and tetrabutyl ammonium iodide (24.7 g) at 90° under an atmosphere of argon for 2 days. The reaction mixture was allowed to cool to room temperature, poured into water (500 ml) and the products recovered by extraction into dichloromethane (3×250 ml). The material isolated from the organic extracts was purified by chromatography on silica developed in a gradient of hexane-ether. Elution with 30% ether-hexane afforded benzyl 4,4-dimethylpent-2-enoate (14 g). Elution with 40% ether in hexane afforded the title compound (350 mg) as a gum; (Found: [m+1]+ =322.2022. C$_{18}$H$_{27}$N$_1$O$_4$ requires [m+1]+ =322.2018); $\nu_{max}$ (film) 1735 cm$^{-1}$; δ(CDCl$_3$) 0.90 (9H, s, C(CH$_3$)$_3$); 1.28 (3H, d, J=7 Hz CHCH$_3$); 2.46 and 2.68 (2H, each dd, J=12 and 5 Hz, CH$_2$(CH$_3$)$_3$); 3.30 (1H, q, J=5 Hz CH-CH$_3$); 3.36 (1H, t, J=5 Hz, CH-CH$_2$); 3.66 (3H, s, OCH$_3$); 5.12 (2H, s, OCH$_2$) and 7.36 (5H, s, C$_6$H$_5$). Elution with 45% ether in hexane afforded benzyl 2-(R)-N-(1-(R)-methoxycarbonylethyl)-amino-4,4-dimethylpentanoate (340 mg); (Found: [m+1]$^+$=322.2022. C$_{11}$H$_{27}$NO$_4$ requires 322.2018); $\nu_{max}$ (film) 3360 and 1735 cms$^{-1}$; δ(CDCl$_3$) 0.90 (9H, s, C(CH$_3$)$_3$); 1.28 (3H, d, J=6 Hz, CHCH$_3$); 1.44 and 1.72 (2H, each dd, J=5 and 12.5 Hz, CH$_2$); 3.32 (1H, q, J=7 Hz, CHCH$_3$); 3.44 (1H, t, J=6 Hz, CHCH$_2$); 3.69 (3H, s, OCH$_3$), 5.24 (2H, s, OCH$_2$) and 7.36 (5H, m, C$_6$H$_5$).

(c) N-[2-(S)-N(1-(R)-Methoxycarbonylethyl)amino-4,4-dimethylpentanoyl]-L-alanine N-Butylamide The foregoing benzyl ester (450 mg) in methanol (50 ml) was treated with palladium on charcoal (10% 400 mg) under 1 atmosphere of hydrogen with continuous stirring. When the uptake of hydrogen has ceased (15 min) the solution was filtered and the filtrate concentrated in vacuo to afford 2-(S)-N-(1-(R)-methoxycarbonylethyl)amino-4,4-dimethylpentanoic acid (210 mg); m.p. 120°-124° (from ether).

This material (200 mg) in CH$_2$Cl$_2$ (50 ml) was treated with L-alanine N-butylamide hydrochloride (220 mg), N-ethyl-N'-(3-dimethylamino propyl)carbodiimide hydrochloride (200 mg) and 1-hydroxybenzotriazole (120 mg) at 0° C. The pH of the reaction mixture was adjusted to 7 by the addition of N-methyl morpholine. After 16 h at 20°, the solution was washed in turn with saturated sodium hydrogen carbonate solution and 1M citric acid solution. The material isolated after evaporation of the dichloromethane was chromatographed on silica developed in a gradient of 20% ethyl acetate in dichloromethane to 60% ethyl acetate in dichloromethane to afford the title compound (110 mg) as a colourless oil, (Found: [m+1]$^+$=358.2705. C$_{18}$H$_{35}$N$_3$O$_4$ requires [m+1]$^+$=358.2706); (CDCl$_3$) 0.92 (3H, t, J=7.5 Hz, CH$_2$CH$_3$); 1.0 (9H, s, C(CH$_3$)$_3$); 1.36 and 1.40 (each 3H, each t, J=6 Hz, 2×CH$_3$); 1.2-1.9 (6H, m, 3×CH$_2$); 3.24 (2H, m, NHCH$_2$); 3.46 (1H, q, J=6 Hz, CH); 3.77 (3H, s, OCH$_3$), 4.46 (1H, t, J=6 Hz, CHCH$_2$); 4.5 (1H, q, J=6 Hz,CH), 7.15 (1H, m, NH) and 7.73 (1H, d, J=8 Hz, NH).

The L-alanine N-butylamide hydrochloride used in step (c) was prepared from N-tertiarybutoxycarbonyl-L-alanine N-butylamide by exposure to TFA in CH$_{23}$Cl$_2$ followed by treatment with ethereal HCl. This in turn was prepared from N-tertiarybutoxy-L-alanine and n-butylamine following the procedure described in Example 2 for N-tertiarybutoxy-O-benzyl-L-tyrosine N-methylamide except that butylamine was used in place of methylamine hydrochloride.

EXAMPLE 24

N-(1-(R)-Carboxyethyl)-S-norleucyl-S-alanine. N-Butylamide

This was prepared from tertiarybutoxycarbonyl-L-norleucine, L-alanine N-butylamide and 2-bromopropionic acid methyl ester as described in the following steps:

(a) Tertiarybutoxycarbonyl-L-norleucyl-L-alanine N-butylamide

Tertiarybutoxycarbonyl-L-norleucine (13.2 g) in CH$_2$Cl$_2$ (200 ml) was treated at 0° with L-alanine N-butylamide (5.25 g), DCC (7.77 g) and 1-hydroxybenzotriazole (5 g). The pH of the reaction mixture was adjusted to 7 with N-methyl morpholine and allowed to warm to room temperature overnight. The precipitated urea was filtered off and the filtrate washed successively with saturated aqueous sodium hydrogen carbonate, water and 1M citric acid. The organic phase was dried over sodium sulphate and the solvent evaporated in vacuo. The residue was chromatographed on silica in a gradient of 30-70% ethyl acetate in dichloromethane. Elution with 50% ethyl acetate in dichloromethane afforded the title compound (7.6 g) which crystallised from ethyl acetate as needles m.p. 108°-112°; (Found: C,60.8; H,9.8; N,11.8. C$_{18}$H$_{35}$N$_3$O$_4$ requires C,60.5; H,9.9; N,11.75%); $\nu_{max}$ (Nujol) 3280, 3340 1675 and 1640 cms$^{-1}$ δ (CDCl$_3$) 0.9 and 0.91 (each 3H, each t, each J=5 Hz, 2×CH$_3$); 1.1-1.9 (10H, m, (CH$_2$)$_3$ and (CH$_2$)$_2$); 1.38 (3H, d, J=5 Hz, 6H$_2$CHCH$_3$); 1.44 (9H, s, C(CH$_3$)$_3$); 3.24 (2H, tt, J=5 Hz NHCH$_2$) and 4.1 and 4.48 (each 1H, each m, 2×CH).

(b) L-Norleucine-L-alanine N-butylamide

Tertiarybutonycarbonyl-L-norleucine-L-alanine N-butylamide (5 g) in dichloromethane (20 ml) was treated with trifluroacetic acid (20 ml) at room temperature for 2 h. The solvents were evaporated in vacuo and the residue in water was treated with excess sodium hydrogen carbonate and the free amine recovered in dichloromethane. Evaporation of the CH$_2$Cl$_2$ and crystallisation of the residue from ether-hexane gave the title compound (3.1 g); m.p. 83°-84°; (Found: C,60.7; H,10.4; N,16.0. C$_{13}$H$_{27}$N$_3$O$_2$ requires C,60.6; H,10.6; N,16.3%); $\nu_{max}$ (Nujol): 3360, 3280, 1635 and 1675 cm$^{-1}$; δ(CDCl$_3$) 0.94 (6H, t, J=5 Hz, 2×CH$_2$CH$_3$); 1.40 (3H, d, J=6 Hz CH—CH$_3$); 1.4-1.9 (10H, m, (CH$_2$)$_3$ and (CH$_2$)$_2$); 3.26 (2H, dt, each J=5 Hz, NH—CH$_2$—); 3.35 (1H, dd, J=4 and 8 Hz, CH—CH$_2$); 4.50 (1H, dq, each J=6 Hz, CH—CH$_3$); 6.9 (1H, m, NH); 7.86 (1H, d, J=7 Hz,NH).

(c) N-(1-(R)-Methoxycarbonylethyl)-S-norleucyl-S-alanine N-Butylamide

L-Norleucine-L-alanine N-butylamide (1 g) in aceto-nitrile (10 ml) was treated with N-methyl morpholine (0.4 g) and methyl 2-bromopropionate (0.64 g) under reflux for 16 h. The solvent was removed in vacuo and the residue in dichloromethane washed successively with 1M citric acid, water and saturated aqueous sodium hydrogen carbonate. The residue after evaporation of the CH$_2$Cl$_2$ was chromatographed on silica in gradient of ethyl acetate in CH$_2$Cl$_2$. Elution with 60% ethyl acetate in CH$_2$Cl$_2$ afforded N-(1-(S)-methoxycarbonylethyl)-S-norleucyl-S-alanine N-butylamide (210 mg); (Found: [m+1]$^+$=344.2547. C$_{17}$H$_{34}$N$_3$O$_4$ requires [m+1]$^+$=344.2582); $\nu_{max}$ (Nujol) 3320 and 1740 cms$^{-1}$; δ(CDCl$_3$) 0.95 (6H, t, J=7 Hz, 2×CH$_2$CH$_3$); 1.2-1.8 (10H, m, (CH$_2$)$_2$ and (CH$_2$)$_3$); 2.98 (1H, dd, J=4 and 5 Hz, CHCH$_2$); 3.24 (3H,m,NHCH$_2$ and CHCO); 3.7 (3H, s, OCH$_3$); 4.56 (1H, dq, J=5 Hz, CH) and 7.04 and 7.9 (each 1H, each m, 2×NH).

Continued elution with 65% ethyl acetate in CH$_2$Cl$_2$ gave the title compound (190 mg), m.p. 84°-88° (from ethyl acetate); (Found: C,59.2; H,9.5; N,12.2. C$_{17}$H$_{33}$N$_3$O$_4$ requires C,59.6; H,9.4; N,12.3%); $\nu_{max}$ (Nujol) 3280 and 1740 cms$^{-1}$; δ(CDCl$_3$) 0.94 (6H, t, J=6 Hz, 2×CH$_2$CH$_3$); 1.38 and 1.42 (each 3H, each d, J=5 Hz, 2×CHCH$_3$); 1.3-1.9 (10H, m, (CH$_2$)$_2$); 3.06 (1H, dd, J=5 and 8 Hz, CHCH$_2$); 3.24 (2H, dt, J=5 and 6 Hz, NHCH$_2$); 3.46 (1H, q, J=6 Hz, CHCO); 3.72 (3H, s, OCH$_3$); 4.67 (1H, dq, J=5 and 7 Hz, CHCH$_3$); 6.84 (1H, m, NH) and 7.82 (1H, d, J=7 Hz, NH).

(d) N-(1-(R)-Carboxyethyl)-S-norleucyl-S-alanine. N-Butylamide

The foregoing methyl ester (150 mg) in CH$_3$OH (50 ml) was treated with 1M NaOH (1 ml) at room temperature for 72 h. Excess acetic acid was added and the solvents evaporated in vacuo. The residue was chromatographed on reverse phase silica (RP18) in a gradient of 0–60% methanol in water. Elution with 50% methanol in water afforded the title compound (110 mg) as needles from ether/hexane; m.p. 185°–190°; (Found: C,56.7; H,9.2; N,12.4. $C_{16}H_{31}N_3O_4.H_2O$ requires C,56.8; H,9.5; N,12.4%); $\nu_{max}$ (Nujol) 3200 and 1650 cm$^{-1}$; $\delta(CD_3OD)$ 0.92 and 0.94 (each 3H, each t, each J=6 Hz, $2\times CH_2CH_3$); 1.36 and 1.48 (each 3H, each d, each J=6 Hz, $2\times C\underline{H}CH_3$); 1.2–1.9 (10H, m, $(CH_2)_2$ and $(CH_2)_3$); 3.20 (2H, t, J=6 Hz NH—$C\underline{H}_2$); 3.56 (1H, q, J=6 Hz, $C\underline{H}CO_2H$); 3.88

EXAMPLE 25

(a) N-[3-N-(Benzyloxycarbonyl)amino-1-(R)-carboxypropyl]-L-leucyl-L-tyrosine N-Methylamide To a stirred solution of the ester from example 11 (0.35 g, 0.63 mM) in methanol (10 ml) was added dilute sodium hydroxide (1.3 ml, 1M). After stirring for 42 h at room temperature the reaction mixture was neutralised with acetic acid, concentrated in vacuo and partitioned between ethyl acetate and water to give the title compound as a solid (121 mg); m.p. 179°–182°; (Found: $[m+1]^+=557.2985$. $C_{28}H_{38}N_4O_7$ requires 557.2975); $\delta(d^6 \text{ DMSO})$ 0.8 (6H, m, $CH(C\underline{H}_3)_2$); 1.18 (2H, m, $C\underline{H}_2CH(CH_3)_2$); 1.46–1.9 (3H, m, $NHCH_2C\underline{H}_2$, $CH_2C\underline{H}(CH_3)_2$); 2.55 (3H, d, J=5 Hz, $CONHC\underline{H}_3$); 2.6–3.8 (6H, m, $NHC\underline{H}_2CH_2C\underline{H}_{CO_2}H$, α-CH, $CH_2Tyr$); 4.38 (1H, dd, J=7 and 15 Hz, α-CH); 5.02 (2H, s, $C\underline{H}_2C_6H_5$); 6.63 (2H, d, J=8 Hz, Tyr); 6.97 (2H, d, J=8 Hz, Tyr); 7.28 (1H, br, CONH); 7.36 (5H, s, $C_6H_5$); 7.84 (1H, br, CONH); 8.14 (1H, d, J=12 Hz, CONH).

(b) N-[3-N-(Benzyloxycarbonyl)amino-1-(R)-methoxycarbonylpropyl]-L-leucyl-L-tyrosine N-Methylamide To a cold (0°) stirred solution of N-[3-N-(Benzyloxycarbonyl)amino-1-(R)-methoxycarbonylpropyl]-L-leucine (422 mg, 1.01 mM) and N-methylmorpholine (204 mg) in dichloromethane (10 ml) was added 1-hydroxybenzotriazole (154 mg, 1.01 mM) and N-ethyl-N'-(3-dimethylaminopropyl)carbodiimide hydrochloride (194 mg, 1.01 mM). After 15 minutes at 0° a solution of L-tyrosine N-methylamide hydrochloride (235 mg, 1.01 mM) in dichloromethane/dimethylformamide (11 ml, 10:1) was added followed by N-methylmorpholine (102 mg, 1.01 mM). The reaction mixture was then allowed to warm and stir to room temperature overnight. The reaction mixture after washing with water, 3N citric acid, saturated aqueous sodium bicarbonate solution and water was dried and concentrated in vacuo to a foam (0.35 g)$\delta(CDCl_3)$ 0.85 (6H, m, $CH_2(CH_3)_2$); 1.1–2.0 (6H, m, $NHCH_2C\underline{H}_2$, $C\underline{H}_2CH(CH_3)_2$); 2.74 (3H, d, J=5 Hz, $CONHC\underline{H}_3$); 2.95–3.4 (6H, m, $NHC\underline{H}_2CH_2C\underline{H}$, α-CH, $C\underline{H}_2C_6H_4$); 3.64 (3H, s, $OCH_3$); 4.62 (1H, dd, J=7 and 15 Hz, α-CH); 5.10 (2H, s, $C\underline{H}_2C_6H_5$); 5.32 (1H, br, CONH); 6.78 (2H, d, J=8 Hz, $C_6H_4$); 6.86 (1H, br, CONH); 7.02 (2H, d, J=8 Hz, $C_6H_4$); 7.35 (5H, s, $C_6H_5$); 7.65 (1H, d, J=10 Hz, CONH).

L-tyrosine N-methylamide hydrochloride used in this preparation was prepared as follows:

(c) L tyrosine N-Methylamide hydrochloride

To a solution of O-benzyl-L-tyrosine N-methylamide HCl (1.13 g) in methanol (50 ml) was added 10% Pd/C and the mixture was stirred in an atmosphere of hydrogen at room temperature and atmospheric pressure for 4 h. The catalyst was then filtered and the solvent was removed in vacuo to yield L-tyrosine N-methylamide HCl as a foam (0.85 g).

(d) N-[3-N-(Benzyloxycarbonyl)amino-1-(R)-methoxycarbonylpropyl]-L-leucine

N-[3-N-(Benzyloxycarbonyl)amino-1-(R)-methoxycarbonylpropyl]-L-leucine t-butyl ester (4.2 g) was treated with Trifluoroacetic acid (50 ml) and water (5 ml) for one hour at room temperature. Volatiles were then removed in vacuo and the residue was coevaporated with ethereal HCl. Recrystallisation of the residue from methanol/ether gave the title compound as its hydrochloride salt (2.2 g) m.p. 103°–109°; (Found: C, 54.55; H, 7.37; N, 6.37. $C_{19}H_{29}N_2O_6Cl$ requires C,54.74; H,7.01; N,6.72%); $\delta(d^6 \text{ DMSO})$ 0.9 (6H, m, $CH(C\underline{H}_3)_2$); 1.72 (3H, m,$C\underline{H}_2CH(CH_3)_2$); 2.05 (2H, m, $NHC\underline{H}_2CH_2$); 3.12 (2H, m, $NHC\underline{H}_2$); 3.74 (3H, s, $OCH_3$); 3.82 (1H, m, α-CH); 4.02 (1H, m, α-CH); 5.02 (2H, s, $C\underline{H}_2C_6H_5$); 7.35 (5H, br s, $C_6H_5$).

The foregoing t-Butyl ester was prepared as described below:

(e) N-[3-N-(Benzyloxycarbonyl)amino-1-(R)-methoxycarbonylpropyl]-L-leucine t-Butyl ester To a solution of methyl 4-N-(benzyloxycarbonyl)amino-2-bromo-butanoate (64 g) and L-leucine t-butyl ester (34 g) in acetonitrile (300 ml) was added N-methylmorpholine (20 g) and the solution was heated under reflux for 48 h. The reaction mixture was then cooled, concentrated in vacuo, taken up in water and extracted with ether. The combined ethereal extracts were then dried and concentrated in vacuo to an oil. Column chromatography of this oil on silica eluting with a gradient of ethyl acetate in hexane gave the title compound as an oil (20 g); $\delta(CDCl_3)$ 0.87 (6H, m, $CH(C\underline{H}_3)_2$); 1.44 (9H, s, $OC(CH_3)_3$); 1.4–1.95 (5H, m, $NHCH_2C\underline{H}_2$, $C\underline{H}_2CH(CH_3)_2$); 3.05–3.5 (4H, m, $NHC\underline{H}_2$, α-CH×2); 3.70 (3H, s, $OCH_3$); 5.10 (2H, s, $C\underline{H}_2C_6H_5$); 5.73 (1H, m, CONH); 7.36 (5H, br s, $C_6H_5$).

EXAMPLE 26

(a) N-(3-N-(Benzyloxycarbonyl)amino-1-(R)-carboxypropyl)-L-leucyl-O-propyl-L-tyrosine N-methyl amide N-(3-N-(Benzyloxycarbonyl)amino-1-(R)-methoxycarbonylpropyl)-L-leucyl-O-propyl-L-tyrosine N-methyl amide (210 mg, 0.35 mM) in methanol (10 ml) was treated with aqueous sodium hydroxide (1.1 ml, 0.5M) at room temperature for 48 h. The reaction was then neutralised with acetic acid and concentrated in vacuo to afford N-(3-N-Benzyloxycarbonyl)amino-1-(R)-carboxylpropyl)-L-leucyl-O-propyl-L-tyrosine N-methyl amide which crystallised from methanol/water as needles m.p. 160°–167° C. (Found: C,63.2; H,7.8; N,9.7. $C_{31}H_{44}N_4O_7+0.3H_2O$ requires: C,63.7; H,7.6; N,9.6%); $\delta(CDCl_3)$ 0.8 (9H, m, $(CH_3)_2CH, CH_3CH_2$); 0.88–1.88 (9H, m, $CH, CH_2, CH_2, CH_2CH_2$); 2.58 (3H, d, J=4 Hz $CH_3NH$); 2.2–3.66 (5H, m, $CH_2, CH, CH_2$); 3.84, (2H, t, J=6 Hz, $CH_2$—O); 4.4 (1H, m, NHCHCO); 5.02 (2H, s, O—$CH_2C_6H_5$); 5.6 (1H, m, NH); 6.76, and 7.08 (4H, each d, each J=7 Hz, $C_6H_4$); 7.24 (1H, m, NH); 7.32 (5H, m, $C_6H_5$); 7.8 (1H, m, NH); 8.14 (1H, m, NH).

The preceeding methyl ester was prepared as follows:

(b) N-(3-N-(Benzyloxycarbonyl)amino-1-(R)methoxycarbonypropyl)-L-leucyl-O-propyl-L-tyrosine N-methyl amide N-Tertiary butyloxycarbonyl-O-propyl-L-tyrosine N-methyl amide (370 mg, 1.1 mM) in dichloromethane (8 ml) was treated with trifluoroacetic acid (2 ml) at 20° C. for 2 h. The solvent was removed in vacuo and the residue redissolved in ether saturated with hydrogen chloride and this procedure repeated twice more to afford O-propyl-L-tyrosine-N-methyl amide hydrochloride (1.1 mM) which was used directly in the next step. N-(3-N-(Benzyloxycarbonyl)amino-1-(R)-methoxycarbonylpropyl)-L-leucine hydrochloride (prepared as described in Example 1) (416 mg, 1 mM) in dichloromethane (10 ml) and dimethyl formamide (2 ml) was treated with 1-hydroxybenzotriazole (159 mg, 1.04 mM), O-propyl-L-tyrosine-N-methyl amide hydrochloride (1.1 mM), N-methyl morpholine (315 mg, 3.3 mM) and N-ethyl-N'-(3-dimethylaminopropyl)-carbodiimide hydrochloride (200 mg, 1.04 mM) at 0° C. The reaction mixture was stirred continuously as it was allowed to warm to 20° C. over 16 h. The reaction was diluted with dichloromethane (30 ml) and washed successively with water, aqueous saturated sodium hydrogen carbonate and aqueous citric acid (1M) dried over anhydrous sodium sulphate and concentrated in vacuo to afford N-(3-N-Benzyloxycarbonyl)amino-1-(R)-methoxycarbonylpropyl)-L-leucyl-O-propyl-L-tyrosine-N-methyl amide (0.22 g, 0.36 mM) which crystallised from ethyl acetate/hexane as needles m.p. 135°–140° C. (Found: C,62.8; H,7.8; N,9.2. $C_{32}H_{46}N_4O_7$+0.5 $H_2O$ requires: C,63.2; H,7.8; N,9.2%); δ(CDCl$_3$) 0.86 (6H,d,d,J=4 Hz J=4 Hz (CH$_3$)$_2$C); 1.02 (3H,t,J=7 Hz CH$_3$CH$_2$); 1.1–1.98 (9H,m,CH,CH$_2$,CH$_2$,CH$_2$CH$_2$); 2.74 (3H,d,J=4 Hz CH$_3$NH); 2.86–3.48, (5H,m,CH$_2$CH$_2$,CH); 3.64 (3H,s,OCH$_3$); 3.86 (2H,t,J=6 Hz,CH$_2$O); 4.58 (1H,m,NHCHCO); 5.06 (2H,s,CH$_2$C$_6$H$_5$); 5.14 (1H,m,NH) 6.54 (1H,m,NH); 6.76, and 7.06 (4H,each d, each J=8 Hz,C$_6$H$_4$); 7.32 (5H,m,C$_6$H$_5$); 7.42 (1H,m,NH).

The intermediate used in the preceeding section was prepared as follows:

(c) N-Tertiarybutyloxycarbonyl-O-propyl-L-tyrosine N-methyl amide

Tertiarybutyloxycarbonyl-L-tyrosine (14.1 g, 50 mM) in dimethyl formamide (200 ml) was cooled to 10° C. and treated with sodium hydride (80%, 3.3 g, 110 mM) with continuous stirring for 1 h. Propyl bromide (6.15 g, 50 mM) was added and the reaction allowed to warm to 20° C. over 16 h. Water (50 ml) was added and the reaction concentrated in vacuo to 100 ml, water 300 ml was added and the solution washed twice with ethyl acetate (300 ml). The reaction was then acidified to pH1 with hydrochloric acid (6N) and extracted twice with ethyl acetate. The organic extract was dried over anhydrous sodium sulphate and concentrated in vacuo to a gum. Column chromatography on silica in ethyl acetate afforded N-tertiarybutyl oxycarbonyl-O-propyl-L-tyrosine (15.1 g 46.7 mM) as a foam which was used directly in the next step. To (13 g, 40 mM) of this foam in dichloromethane (250 ml) was added 1-hydroxybenzotriazole (6.8 g, 45 mM); methylamine hydrochloride (2.5 g, 80 mM); N-methyl morpholine (8 g, 80 mM) and dicyclohexylcarbodiimide (9.1 g, 45 mM) at 0° C. The reaction was stirred continuously whilst allowed to warm to 20° C. over 6 h. The reaction was filtered and the filtrate washed with water, aqueous saturated sodium hydrogen carbonate and aqueous citric acid (1M), dried over anhydrous sodium sulphate and concentrated in vacuo to afford N-tertiarybutyloxycarbonyl-O-propyl-L-tyrosine -N-methyl-amide (8.5 g, 25 mM) which crystallised from ethyl acetate as needles m.p. 134°–135° (Found: C,64.5; H,8.7; N,8.4. $C_{18}H_{28}N_2O_4$ requires: C,64.3; H,8.4; N,8.3%; δ(CDCl$_3$) 0.96 (3H,t,J=8 Hz,CH$_3$CH$_2$); 1.36 (9H,s,(CH$_3$)$_3$C); 1.74 (2H,t,q,J=7 Hz,J=7 Hz,CH$_2$); 2.68 (3H,d,J=4 Hz,CH$_3$NH); 2.92 (2H,m,CH$_2$C$_6$H$_4$); 3.82 (2H,t,J=7 Hz,CH$_2$-O); 4.16 (1H,m,NHCHCO); 4.98 (1H,m,NH); 5.68 (1H,m,NH); 6.74 and 7.0 (4H, each 2H, each d, each J=8 Hz,C$_6$H$_4$).

EXAMPLE 27

(a) N-[3-N-(Benzyloxycarboxyl)amino-1-(R)-carbonypropyl]-L-leucyl-O-isopropyl-L-tyrosine N-methylamide N-[3-N-(Benzyloxycarbonyl)amino-1-(R)-methoxycarbonylpropyl]-L-leucyl-O-isopropyl-L-tyrosine N-methylamide (0.4 g 0.65 mM) in methanol (15 ml) was treated with aqueous sodium hydroxide (2 ml, 0.5M, 0.75 mM) at 20° C. for 24 h. The solution was then adjusted to pH7 with acetic acid and concentrated to low volume. The white solid which crystallised was recrystallised from methanol/water 1:1 to afford N-[3-N-Benzyloxycarbonyl)amino-1-(R)-carboxypropyl]-L-leucyl-O-isopropyl-L-tyrosine-N-methyl amide (100 mg, 0.17 mM) m.p. 148°–160° C. (Found: C,63.3; H,7.6; N,9.6. $C_{31}H_{44}N_4O$ requires: C,63.7; N,7.8; N,9.3%) δ(CDCl$_3$) 0.8 (6H,m, (CH$_3$)$_2$C); 0.98–1.84 (5H,m,CH$_2$,CH$_2$CH); 1.22 (6H,d,J=6 Hz, (CH$_3$)$_2$CHO); 2.56 (3H,d,J=4 Hz CH$_3$NH); 2.64–3.66 (7H,m,CH$_2$,CH$_2$,CH$_2$,CH); 4.4 (1H,m,NHCHCO); 4.52 (1H,m,NHCHCO); 5.0 (2H,s,OCH$_2$C$_6$H$_5$); 6.72, and 7.06 (each 2H,each d,each J=8 Hz C$_6$H$_4$); 7.32 (5H,m,C$_6$H$_5$); 7.88 (1H,m,NH); 8.22 (1H,m,NH).

The preceeding methyl ester was prepared as follows:

(b) N-[3-N-(Benzyloxycarbonyl)amino-1-(R)-methoxycarbonylpropyl]-L-leucyl-O-isopropyl-L-tyrosine N-methylamide N-Tertiary butyloxycarbonyl-O-isopropyl-L-tyrosine-N-methylamide (370 mg, 1.1 mM); in dichloromethane (10 ml) was treated with trifluoroacetic acid (10 ml) at 20° C. for 1 h. The resulting trifluoroacetate was converted to the hydrochloride salt by concentrating to a gum in vacuo and redissolving the residue in ether saturated with hydrogen chloride. This procedure was repeated three times. To the product in dichloromethane (10 ml) was added N-[3-N-(Benzyloxycarbonyl)amino-1-(R)-methoxycarbonylpropyl]-L-leucine hydrochloride (416 mg, 1 mM) (prepared as described in Example 1) 1-hydroxybenzotriazole (159 mg, 1.04 mM), and N-(3-dimethylaminopropyl)-N'-ethylcarbodiimide hydrochloride (200 mg, 1.04 mM) at 0° C. The stirred reaction mixture was adjusted to pH7 with N-methylmorpholine and allowed to warm to room temperature over 16 h. The reaction was diluted with dichloromethane and washed with water, aqueous saturated sodium hydrogen carbonate, and aqueous citric acid (1M), dried over sodium sulphate and concentrated in vacuo to a gum. (Found: [M+H]$^+$=599.3446. $C_{32}H_{46}N_4O_7$ requires: [M+H]$^+$=599.3445); δ(CDCl$_3$) 0.84 (6H,m,(CH$_3$)$_2$CH) 1.3 (6H,d,J=7 Hz, (CH$_3$)$_2$CHO) 1.1–1.96 (5H,m,2×CH$_2$,CH) 2.72 (3H,d,J=4 Hz,CH$_3$NH); 3.04–3.36 (6H,m,2×CH$_2$,2×CH); 3.64 (3H,s,CH$_3$O); 4.46 (1H,m,NHCHCO); 4.56 (1H,m,NHCHCO); 5.06 (2H,s,O—(CH$_2$C$_5$H$_6$); 5.32 (1H,m,NH); 6.76, and 7.04 (each 2H,each d,each J=8 Hz,C$_6$H$_4$); 6.98 (1H,m,NH); 7.3 (5H,m,C$_6$H$_5$); 7.52 (1H,m,NH).

The intermediate used in the preceeding section was prepared as follows:

(c) N-Tertiarybutyloxycarbonyl-O-isopropyl-L-tyrosine N-methylamide

N-Tertiarybutyloxycarbonyl-L-tyrosine (14.1 g 50 mM) in dry dimethylformamide (200 ml) was treated with sodium hydride (3.45 g, 115 mM) with vigorous stirring under an atmosphere of argon at 10° C. for 1 h. 2-Bromopropane (6.15 g, 50 mM) was added and the stirred solution allowed to warm to 20° C. over 16 h. Water (200 ml) was added and the solution extracted with ethyl acetate (2×200 ml). The reaction was adjusted to pH1 with hydrochloric acid (6M) and extracted with dichloromethane 2×300 ml. The combined extracts were columned on silica in ethyl acetate to afford N-tertiarybutyloxycarbonyl-O-isopropyl-L-tyrosine (13.6 g, 42 mM) as a foam. The foam was dissolved in dichloromethane (200 ml) and treated with methylamine hydrochloride (2.5 g, 80 mM), 1-hydroxybenzotriazole (6.75 g, 44 mM), dicyclohexylcarbodiimide (9.1 g, 44 mM) and N-methyl morpholine (2.5 g, 80 mM) at 0° C. with continuous stirring. The solution was allowed to warm to room temperature over 16 h and filtered. The filtrate was washed with water, aqueous saturated sodium hydrogen carbonate solution and aqueous citric acid (1M), dried over sodium sulphate and concentrated in vacuo to afford N-tertiarybutyloxycarbonyl-O-isopropyl-L-tyrosine-N-methyl amide (6.1 g, 18 mM) which crystallised from ethyl acetate/hexane as needles m.p. 110°–114° C. (Found: C,63.5; H,8.4; N,8.7. $C_{18}H_{28}N_2O_4$ 0.25 $H_2O$ requires: C,63.4; H,8.4; N,8.2%) $\delta(CDCl_3)$ 1.32 (6H,d,J=7 Hz, $(CH_3)_2CH$); 1.4 (9H,s,$(CH_3)_3C$); 2.72 (3H,d,J=4 Hz $NHCH_3$); 2.98, (2H,d,J=7 Hz $CH_2C_6H_5$); 4.26 (1H,m,NHCHCO); 4.5 (1H, heptet, J=5 Hz, $CH(CH_3)_2$); 5.08 (1H,m,NH); 5.92 (1H,m,NH); 6.78, and 7.04 (each 2H,each d,each J=8 Hz $C_6H_4$).

EXAMPLE 28

(a) N-[3-N-(Benzyloxycarboxyl)(amino-1-(R)-carboxypropyl)-L-leucyl-O tertiary butyl-L-tyrosine. N-methyl amide N-[3-N-(Benzyloxycarbonyl)amino-1-(R)-methoxycarbonylpropyl]-L-leucyl-O-tertiary butyl-L-tyrosine N-methyl amide (0.26 g, 0.42 mM) in methanol (10 ml) was treated with aqueous sodium hydroxide (1.3 ml, 0.5M) at 20° C. for 24 h. The reaction was then adjusted to pH 7 with hydrochloric acid (6N) and concentrated in vacuo to low volume. The white solid which crystallized out was washed with ether and water and dried in vacuo to afford N-[3-N-(Benzyloxycarbonyl)amino-1-(R)-carboxy propyl-L-leucyl-O-tertiary butyl-L-tyrosine-N-methyl amide m.p. 160° C. dec. (Found: C,62.51; H,7.67; N,9.24; $C_{32}H_{46}N_4O_7.H_2O$ requires: C,62.32; H,7.84; N,9.08%). $\delta(CDCl_3)$ 0.78 (6H,m $(CH_3)_2C$); 1.08–1.86 (5H,m,$CH_2,CH_2CH$); 1.24 (9H,s,$(CH_3)_3C$); 2.56 (3H,d,J=4 Hz,$CH_3NH$); 2.44–3.2 (6H,m,2×$CH_2$,2×CH); 4.4 (1H,m,NHCHCO); 5.0 (2H,s,$CH_2C_5H_6$); 6.82 and 7.08 (each 2H,each d,each J=8 Hz,$C_6H_4$); 7.22 (1H,m,NH); 7.3 (5H,m,$C_6H_5$); 7.84 (1H,m,NH); and 8.2 (1H,m,NH).

The preceeding methyl ester was prepared as follows:

(b) N-[3-N-(Benzyloxycarbonyl)amino-1-(R)-methoxy carbonyl propyl]-L-leucyl-O-tertiary butyl-L-tyrosine N-methyl amide N-Benzyloxycarbonyl-O-tertiarybutyl-L-tyrosine N-methylamide (2.4 g 6.2 mM) in ethanol (10 ml) was heated under reflux with cyclo hexene (4 ml) acetic acid (0.38 g 6.2 mM) and palladium on carbon (10%, 1 g) under an atmosphere of argon for 20 m. The solvents were then removed in vacuo to afford O-tertiarybutyl-L-tyrosine N-methylamide acetate m.p. 121°–123° C. This was dissolved in dichloromethane (50 ml) and shaken with aqueous saturated sodium hydrogen carbonate (50 ml). The organic layer was dried over anhydrous sodium sulphate and concentrated in vacuo to afford O-tertiary butyl-L-tyrosine N-methyl amide as a crude gum which was used directly in the next step. N-[3-N-Benzyloxy carbonyl]amino-1-(R)-methoxycarbonylpropyl]-L-leucine hydrochloride (418 mg, 1 mM) in dichloromethane (10 ml) was treated with 1-hydroxybenzotriazole (159 mg, 1.0 mM) N-methylmorpholine (210 mg, 2 mM), O-tertiarybutyl-L-tyrosine-N-methyl amide (275 mg, 1.1 mM) and N-(3-dimethylaminopropyl)-N'-ethyl carbodiimide hydrochloride (200 mg, 1.04 mM) at 0° C. with continuous stirring. The reaction mixture was adjusted to pH7 with N-methylmorpholine and was allowed to warm to 20° C. over 16 h. The reaction was diluted with dichloromethane and washed successively with water, aqueous saturated sodium hydrogen carbonate and aqueous 3N citric acid, dried over sodium sulphate and concentrated in vacuo to afford N-[3-N-(Benzyloxycarbonyl)amino-1-(R)-methoxy carbonypropyl]-L-leucine-O-tertiary butyl-L-tyrosine-N-methyl amide (350 mg, 0.6 mM) which crystallised from ethyl acetate/hexane as needles m.p. 66°–68° C. (Found: C,64.7; H,8.1; N,9.2. $C_{33}H_{48}N_4O_7$ requires: C,4.7; H,7.9; N,9.1%); $\delta(CDCl_3)$ 0.88 (6H,d,J=7 Hz, $(CH_3)_2C$); 1.32 (9H,s, $(CH_3)_3C$); 1.16–2.0 (5H,m,$CH_2,CH_2CH$); 2.72 (3H,d,J=5 Hz, $CH_3NH$); 3.02 to 3.4 (6H,m,2×CH,2×$CH_2$); 3.66 (3H,s,$CH_3O$); 4.58 (1H,m,NHCHCO); 5.08 (2H,s,$CH_2C_5H_6$); 5.2 (1H,m,NH); 6.54 (1H,m,NH); 6.88 and 7.06 (each 2H,each d,each J=8 Hz,$C_6H_4$); 7.32 (5H,m,$C_6H_5$); 7.52 (1H,m,NH).

The foregoing intermediate was prepared as follows:

(c) N-Benzyloxycarbonyl-O-tertiarybuty-L-tyrosine N-methyl amide

Benzyloxycarbonyl-O-tertiarybutyl-L-tyrosine dicyclohexyclamine salt (5 g, 0.9 mM) was dissolved in aqueous citric acid (25 ml, 1M) and extracted with ethyl acetate (3×50 ml). The organic layer was dried over sodium sulphate and concentrated in vacuo to afford the free acid (4.1 g) as a gum. This was dissolved in dichloromethane (100 ml) and treated with hydroxy benzotriazole (1.5 g, 10 mM), methylamine hydrochloride (0.56 g, 18 mM) and dicyclohexyl carbodiimide (2.1 g 10 mM) at 0° C. with continuous stirring. The reaction was allowed to warm to 20° C. over 16 h and then filtered. The filtrate was diluted with dichloromethane and washed with water. aqueous saturated sodium hydrogen carbonate and aqueous citric acid (1M), dried over sodium sulphate and concentrated in vacuo to afford Benzyloxycarbonyl-O-tertiary butyl-L-tyrosine N-methylamide (2.5 g) which crystallised from ethyl acetate/hexane as needles m.p. 124°–125° C. (Found: C,68.7; H,7.9; N,7.4. $C_{22}H_{28}N_2O_4$ requires: C, 68.7, H,7.3; N,7.3%); $\delta(CDCl_3)$ 1.34 (9H,s,$(CH_3)_3C$); 2.68 (3H,d,J=4 Hz $NHCH_3$); 2.94 and 3.1 (2H,each dd,each J=15 Hz,J=6 Hz,$CH_2C_6H_4$); 4.3 (1H,q,J=5 Hz NHCHCO); 5.08 (2H,s,$CH_2C_6H_5$); 5.34 (1H,m,NH); 5.58 each (1H,m,NH); 6.88, and 7.06 (each 2H,each d, each J=8 Hz,$C_6H_4$); 7.3 (5H,m,$C_6H_5$).

EXAMPLE 29

(a) N-[3-N-(Benzyloxycarbonyl)amino-1-(R)-carboxypropyl]-L-leucyl-O-pentyl-L-tyrosine N-Methylamide To a stirred solution of 1 (280 mg, 0.47 mM) in methanol (10 ml) was added dilute sodium hydroxide (0.7 ml, 1M). After stirring for 48 h at room temperature the reaction was neutralised with acetic acid and was concentrated in vacuo to a solid. Recrystallisation from methanol/water gave the title compound as a solid (107 mg); m.p. 165°–170°; δ(d$^6$DMSO) 0.8 (6H, dd, J=5 Hz, J=CH$_2$CH(CH$_3$)$_2$); 0.87 (3H, t, J=7 Hz, CH$_2$CH$_3$); 1.1–1.25 (2H, m, CH$_2$CH(CH$_3$)$_2$); 1.26–1.85 (9H, m, OCH$_2$(CH$_2$)$_3$(CH$_3$), NHCH$_2$CH$_2$CH, CH$_2$CH(CH$_3$)); 2.56 (3H, d, J=8 Hz, CONHCH$_3$); 2.6–3.65 (6H, m, NHCH$_2$CH$_2$CH CO$_2$H, α-CH, CH$_2$Tyr); 3.87 (2H, t, J=7 Hz, OCH$_2$CH$_2$); 4.42 (1H, dd, J=7 and 15 Hz, α-CH); 5.02 (2H, s, CH$_2$C$_6$H$_5$); 6.77 (2H, d, J=8 Hz, Tyr); 7.10 (2H, d, J=8 Hz, Tyr); 7.26 (1H, br, CONH); 7.35 (5H, s, C$_6$H$_5$); 7.85 (1H, br, CONH); 8.14 (1H, d, J=8 Hz, CONH).

The preceeding ester was synthesised as described below:

(a) N-[3-N-(Benzyloxycarbonyl)amino-1-(R)-methoxycarbonyl propyl]-L-leucyl-O-pentyl-L-tyrosine N-Methylamide To a solution of N-[3-N-(Benzyloxycarbonyl)amino-1-(R)-methoxycarbonylpropyl]-L-leucine hydrochloride (418 mg, 1 mM) in dichloromethane (10 ml), stirred and cooled to 0° was added N-methylmorpholine (101 mg), 1-hydroxybenzotriazole (153 mg, 1 mM) and dicyclohexylcarbodiimide (206 mg, 1 mM). After 15 minutes at 0° a solution of O-pentyl-L-tyrosine N-methylamide (265 mg) (which had been prepared from the N-benzyloxycarbonyl precursor in the usual manner) was added dissolved in dichloromethane (10 ml). The reaction after being allowed to warm and stir to room temperature overnight was filtered, washed with water, 3N citric acid, saturated aqueous sodium bicarbonate and water. The washed organic extract was dried and concentrated to an oil in vacuo. Chromatography on silica eluting with ethyl acetate gave N-[3-N-(benzyloxycarbonyl)amino-1-(R)-methoxycarbonyl propyl]-L-leucyl-O-pentyl-L-tyrosine N-Methylamide as a solid (359 mg); m.p. 81°–85°; (Found: C, 64.78; H, 8.05; N, 8.82. C$_{34}$H$_{52}$N$_4$O$_7$ requires C, 64.94; H, 8.34; N, 8.91%); δ(CDCl$_3$) 0.83 (3H, d, J=5 Hz, CH$_2$CH(CH$_3$) 0.87 (3H, d, J=5 Hz, CH$_2$CH(CH$_3$); 0.92 (3H, d, J=7 Hz, CH$_2$CH$_3$); 1.0–2.0 (12H, NHCH$_2$CH$_2$, NH, CH$_2$CH(CH$_3$)$_2$, OCH$_2$(CH$_2$)$_3$CH$_3$); 2.75 (3H, d, J=5 Hz, CONHCH$_3$); 2.9–3.6 (6H, m, NHCH$_2$CH$_2$CHCO$_2$H, α-CH, CH$_2$Tyr); 3.66 (3H, s, OCH$_3$); 3.9(2H, t J=7 Hz, OCH$_2$CH$_2$); 4.58 (1H, dd, J=7 and 15 Hz, CH); 5.11 (3H, br, CH$_2$C$_6$H$_5$, CONH); 6.58 (1H, br, CONH); 6.81 (2H, d, J=8 Hz, C$_6$H$_4$); 7.10 (2H, d, J=8 Hz, C$_6$H$_4$); 7.36 (5H, s, C$_6$H$_5$); 7.47 (1H, d, J=8 Hz, CONH).

N-Benzyloxycarbonyl-O-pentyl-L-tyrosine N-methylamide used in this preparation was synthesized as follows:

(c) N-(Benzyloxycarbonyl)-O-pentyl-L-tyrosine N-Methylamide

To a cold (0°) stirred solution of N-benzyloxycarbonyl-O-pentyl-L-Tyrosine (8.3 g, 22 mM) in THF (120 ml) was added 1-hydroxybenzotriazole (3.6 g, 24 mM) and dicyclohexylcarbodiimide (4.9 g, 24 mM). After stirring for 25 minutes at 0° a solution of methylamine in THF (7.2 ml, 5M) was added and the reaction was stirred and warmed to room temperature overnight. The reaction mixture was then filtered, evaporated in vacuo and dissolved in dichloromethane (150 ml). The dichloromethane extract after washing with water, 3N citric acid, saturated sodium bicarbonate solution and water was dried, filtered and concentrated in vacuo to a solid. Recrystallisation from ethyl acetate gave the required N-Methylamide as needles (6.43 g); m.p. 132°–135°; (Found: C, 69.30; H, 7.63; N, 7.43. C$_{23}$H$_{30}$N$_2$O$_4$ requires C, 69.32; H, 7.59; N, 7.03%); δ(CDCl$_3$) 0.92 (3H, t, J=7 Hz, CH$_2$CH$_3$); 1.25–2.0 (6H, m, OCH$_2$(CH$_2$)$_3$CH$_3$); 2.71 (3H, t, J=5 Hz, CONHCH$_3$); 3.0 (2H, m, CH$_2$Tyr); 3.92 (3H, t, J=7 Hz, OCH$_2$CH$_3$); 4.29 (1H, dd, J=7 and 15 Hz, α-CH); 5.09 (2H, s, CH$_2$C$_6$H$_5$); 5.37 (1H, br, CONH); 5.69 (1H, br, CONH); 6.82 (2H, d, J=8 Hz, Tyr); 7.08 (2H, d, J=8 Hz, Tyr); 7.33 (5H, m, C$_6$H$_5$).

The preceeding acid was synthesized as described below.

(d) N-(Benzyloxycarbonyl)-O-pentyl-L-tyrosine

To a cold (10°) stirred solution of N-benzyloxycarbonyl-L-tyrosine (12.61 g, 40 mM) in dry DMF (150 ml) under argon was added sodium hydride (2.76 g, 80% dispersion in oil). After stirring for one hour at 10° n-bromopentane (6.0 g, 40 mM) was added and the reaction mixture was allowed to stir and warm to room temperature overnight. Water (800 ml) and ethyl acetate (800 ml) were then added and the separated organic phase was acidified and extracted with ethyl acetate (200 ml×3). This organic extract was dried, filtered and concentrated to an oil in vacuo. Chromatography on silica eluting with ethyl acetate gave N-benzyloxycarbonyl-O-pentyl-L-Tyrosine which was recrystallised from ether/hexane to give a solid (8.5 g), m.p. 77°–81°; (Found: C, 68.58; H, 7.19; N, 3.77. C$_{22}$H$_{27}$NO$_5$ requires C, 68.55; H, 7.06; N, 3.63%); δ (CDCl$_3$) 0.92 (3H, t, J=7 Hz, CH$_2$CH$_3$); 1.29–1.52 (4H, m, CH$_2$ alkyl); 1.66–1.86 (2H, m, CH$_2$ alkyl); 3.0–3.12 (2H, m, CH$_2$Tyr); 3.93 (2H, t, J=7 Hz, OCH$_2$CH$_3$); 4.67 (1H, m, CH); 5.12 (2H, s, CH$_2$C$_6$H$_5$); 5.2 (1H, d, J=8 Hz, CONH); 6.82 (2H, d, J=8 Hz, C$_6$H$_4$); 7.07 (2H, d, J=8 Hz, C$_6$H$_4$); 7.35 (5H, s, C$_6$H$_5$).

EXAMPLE 30

(a) N[3-N-(Benzyloxycarbonyl)amino-1-(R)-carboxypropyl]-L-leucyl-O-3(methyl)butyl-L-tyrosine N-methyl amide N-[3-N-(Benzyloxycarbonyl)amino-1-(R)methoxycarbonylpropyl]-L-leucyl-O-3(methyl)butyl-L-tyrosine N-methyl amide (270 mg 0.43 mM) in methanol (10 ml) was treated with aqueous sodium hydroxide (1.3 ml, 0.5M) at 20° C. for 48 h. The reaction was adjusted to pH4 with acetic acid and the solvent removed in vacuo to afford N-[3-N-(Benzyloxycarbonyl)amino-1-(R)-carboxypropyl]-L-leucyl-O-3(methyl)butyl-L-tyrosine N-methylamide (121 mg) which crystallised from methanol/water as needles m.p. 155°–160° C. (Found: C,63.7; H,7.7; N,9.2. C$_{33}$H$_{48}$N$_4$O$_7$ requires: C,64.7; H,7.9; N,9.1%); δ ((CD$_3$)$_2$SO) 0.8 and 0.92 (12H,each m, 2×(CH$_3$)$_2$C); 1.0–1.9 (8H,m,3×CH$_2$,2×CH) 2.56 (3H,d,J=4 Hz CH$_3$NH) 2.76–3.8 (6H,m,2×,CH$_2$,2×CH); 3.92 (2H,m,CH$_2$O); 4.52 (1H,m,NHCHCO); 5.0 (2H,s,CH$_2$C$_6$H$_5$); 6.76 and 7.1 (each 2H,each d,each J=8 Hz,C$_6$H$_4$); 7.34 (5H,m,C$_6$H$_5$); 7.9 (1H,m,NH); 8.1 (1H,m,NH).

The preceeding methyl ester was prepared as described below:

(b) N-[3-N-(Benzyloxycarbonyl)amino-1-(R)-methoxy carbonylpropyl]-L-leucyl-O-3(methyl)butyl-L-tyrosine N-methyl amide Tertiarybutyloxycarbonyl-O-3-methylbutyl-L-tyrosine-N-methylamide (401 mg, 1.1 mM) in dichloromethane (10 ml) was treated with trifluoroacetic acid (10 ml) at 20° C. for 1.5 h. The solution was concentrated in vacuo to a gum and dissolved in ether saturated with hydrogen chloride, and this procedure repeated twice to afford O-3(methyl)butyl-L-tyrosine-N-methylamide hydrochloride which was used directly in the next step. N(3-N-(Benzyloxycarbonyl)amino-1-(R)-methoxycarbonyl propyl)-L-leucine Hydrochloride (418 mg 1 mM) in dichloromethane (20 ml) and dimethyl formamide (2 ml) was treated with N-methyl morpholine (420 mg, 4 mM), 1-hydroxybenzo-triazole (159 mg 1.04 mM), O-3-Methylbutyl-L-tyrosine N-methyl amide hydrochloride (1.1 mM) and N-ethyl-N'-(3-dimethylaminopropyl)carbodiimide hydrochloride (200 mg, 1.04 mM) at 0° C. with continuous stirring. The reaction was allowed to warm to 20° C. over 16 h. The reaction was diluted with dichloromethane (30 ml) and washed successively with water, aqueous saturated sodium hydrogen carbonate and aqueous citric acid (1M), dried over sodium sulphate and concentrated in vacuo to afford N-[3-N-(Benzyloxycarbonyl)amino-1-(R)-methoxy carbonypropyl)-L-leucyl-O-3(methyl)butyl-L-tyrosine N-methylamide (360 mg, 0.57 mM) which crystallised from ethyl acetate/hexane as needles m.p. 78°-81° C. (Found: C,65.8; H,8.0; N,8.9 $C_{34}H_{50}N_4O_7$ requires: C,64.8; H,8.3; N,8.9); δ ($CDCl_3$) 0.86 (6H,dd,J=6 Hz J=1 Hz $(CH_3)_2C$) 0.94 (6H,d,J=6 Hz, $(CH_3)_2C$); 1.02–2.0 (8H,m,3×$(CH_2)$,2×CH); 2.74 (3H,d,J=4 Hz,$CH_3NH$); 2.92–3.42 (6H,m,2×$CH_2$,2×CH); 3.66 (3H,s,$CH_3O$); 3.92 (2H,t,J=6 Hz,$CH_2O$); 4.58 (1H,m,NHCHCO); 5.1 (2H,s,$CH_2C_6H_5$); 5.16 (1H,m,NH); 6.52 (1H,m,NH); 6.78 and 7.06 (each 2H, each d, each J=8 Hz,$C_6H_4$); 7.3 (5H,m,$C_6H_5$); 7.74 (1H,m,NH).

The intermediate used in the preceeding section was prepared as described below:

(c) Tertairybutyl-oxycarbonyl-O-3(methyl)butyl-L-tyrosine-N-methylamide

Tertiarybutyloxycarbonyl-L-tyrosine (14.1 g, 50 mM) in dry dimethyl formamide (200 ml) was treated with sodium hydride (3.45 g, 115 mM) under an atmosphere of argon at 10° C. for 1 h. 3(Methyl)butyl bromide (8.3 g, 55 mM) was added and the reaction allowed to warm to 20° C. over 20 h. Water (200 ml) was added and the solution washed with ethyl acetate (2×300 ml) and adjusted to pH1 with 6N HCl. The solution was extracted with ethyl acetate and the extract dried over sodium sulphate and concentrated in vacuo to afford tertiary butyl oxycarbonyl-O-3(methyl)butyl-L-tyrosine (15 g, 35 mM) as a gum. The gum was dissolved in dichloromethane (200 ml) and treated with 1-hydroxybenzotriazole (5.8 g, 38 mM) methylamine hydrochloride (2.2 g, 70 mM), dicyclohexyl carbodiimide (7.8 g, 38 mM), adjusted to pH7 with N-methyl morpholine and stirred continuously as the reaction was allowed to warm from 0° C. to 20° C. over 16 h. The reaction was filtered and washed with water, aqueous saturated sodium hydrogen carbonate and aqueous saturated citric acid, dried over sodium sulphate and concentrated in vacuo to afford tertiarybutyloxycarbonyl-O-3(methyl)butyl-L-tyrosine N-methyl amide (6.45 g, 17 mM) which crystallised from ethyl acetate/hexane as needles m.p. 115°-116° C. (Found: C,66.3; H,9.3; N,8.0 $C_{20}H_{32}N_2O_4$ requires: C,65.9; H,8.9; N,7.7%); δ ($CDCl_3$) 0.94 (6H,d,J=6 Hz,$(CH_3)_2C$); 1.42 (9H,s,$(CH_3)_3$); 1.6–2.0 (3H,m,$CH_2CH$) 2.74 (3H,d,J=4 Hz, $CH_3NH$); 3.0 (2H,m,$CH_2C_6H_4$); 3.9 (2H,t,J=8 Hz,$CH_2O$); 4.24 (1H,m,NHCHCO); 5.08 (1H,m,NH) 5.8 (1H,m,NH) 6.8, and 7.06 (each 2H,each d,each J=8 Hz,$C_6H_4$).

EXAMPLE 31

(a) N-[3-N-(Benzyloxycarbonyl)amino-1-(R)-carboxypropyl]-L-leucyl-O-6(methyl)heptyl-L-tyrosine N-methyl amide N-[3-N-(Benzyloxycarbonyl)amino-1-(R)-methoxycarbonylpropyl]-L-leucyl-O-6-methyl heptyl-L-tyrosine N-methyl amide (0.16 g, 0.24 mM) in methanol (10 ml) was treated with aqueous sodium hydroxide (0.7 ml, 0.5M) with continuous stirring at 20° C. for 24 h. The reaction was adjusted to pH7 with acetic acid and concentrated in vacuo to afford a white solid which was washed with ethyl acetate and water and dried in vacuo to yield N-[3-N-(Benzyloxycarbonyl)amino-1-(R)-carboxypropyl]-L-leucyl-O-6(methyl)heptyl-L-tyrosine N-methylamide m.p. 176°-177° C. (Found: C,66.3; H,8.2; N,8.4; $C_{36}H_{54}N_4O_7+H_2O$ requires: C,64.3; H,8.4; N,8.4%); δ ($CDCl_3$) 0.84 (12H,m,2×$(CH_3)_2C$); 1.0–1.8 (14H,m,6×,$CH_2$,2×(CH); 2.56 (3H,d,J=$CH_3NH$); 2.4–3.64 (6H,m,2×$CH_2$,2×CH); 3.88 (2H,m,$CH_2O$); 4.82 (1H,m, NHCHCO); 5.0 (2H,s,$CH_2C_6H_5$); 6.74, and 7.06 (each 2H,each d,each J=8 Hz,$C_6H_4$); 7.18 (1H,m,NH); 7.32 (5H,m,$C_6H_5$); 7.8, (1H,m,NH); 6.08 (1H,m,NH).

The methyl ester used in the preceeding section was prepared as described below:

(b) N-[3-N-(Benzoyloxycarbonyl)amino-1-(R)-methoxycarbonylpropyl]-L-leucyl-O-(methyl)heptyl-L-tyrosine N-Methyl amide N-Tertiarybutyl oxycarbonyl-O-6-methyl heptyl-L-tyrosine-N-methylamide (447 mg, 1.1 mM) in $CH_2Cl_2$ (10 ml) was treated with trifluoroacetic acid (10 ml) at 20° C. for 2 h. The solvent was removed in vacuo and the residue redissolved in ether saturated with hydrogen chloride. This was repeated twice to afford O-6-methyl heptyl-L-tyrosine-N-methylamide hydrochloride and treated with N-methyl morpholine (420 mg, 4.4 mM), 1-hydroxybenzotriazole (159 mg, 1.04 mM), N-[3-N-(Benzoyloxycarbonyl) amino-1-(R)-methoxycarbonylpropyl]-L-leucine hydrochloride (418 mg, 1 mM) prepared as described in Example (1) and N-Ethyl-N'-3'dimethyl aminopropyl carbodiimide hydrochloride (200 mg, 1.04 mM) at 0° C. The reaction was adjusted to pH7 with N-methylmorpholine, stirred continuously and allowed to warm to 20° C. over 1 h. The reaction was diluted with dichloromethane and washed successively with water, aqueous saturated sodium hydrogen carbonate and aqueous citric acid (1M) dried over sodium sulphate and concentrated in vacuo to afford a gum. Column chromatography on silica in ethyl acetate/hexane 1:1 afforded N-[3-N-(Benzyloxycarbonyl)amino-1-(R)-methoxy carbonylpropyl]-L-leucyl-O-6(methyl)heptyl-L-tyrosine N-methylamide (0.17 g, 0.25 mM) as a colourless oil (Found: [M+H]+=694.213. $C_{37}H_{56}N_4O_7$ requires: [M+H]+=699.4227); δ ($CDCl_3$) 0.88 (12H,m,2×$(CH_3)_2CH$); 1.12–1.92 (14H,m,6×$CH_2$,2×CH) 2.74 (3H,d,J=4 Hz$CH_3NH$); 2.9–3.42 (6H,m,$CH_2$,2×CH); 3.64 (3H,s,$CH_3O$); 3.9 (2H,t,J=5 Hz$CH_2NH$); 4.6 (1H,q,NHCHCO) 5.1 (2H,s,$CH_2C_6H_5$); 5.3 (1H,m,NH); 6.7 (1H,m,NH); 6.76; and 7.06 (each 2H,each d,each J=8 Hz,$C_6H_4$); 7.3 (5H,s,$C_6H_5$); 7.5 (1H,m,NH).

The preceeding intermediate was prepared as described below:

(c) N-Tertiary butyl oxycarbonyl-O-6-methyl heptyl-L-tyrosine-N-methylamide

N-Tertiarybutyloxycarbonyl-L-tyrosine (14.1 g, 50 mM) in dry dimethylformamide (200 ml) was treated with sodium hydride (3.45 g, 115 mM) at 10° C. under an atmosphere of argon for 2 h. 6-Methyl hexyl bromide (13.1 g, 50 mM) was added and the reaction stirred at 20° C. for 16 h. Water (200 ml) was added and the reaction extracted twice with ethyl acetate (400 ml). The aqueous phase was adjusted to pH1 with hydrochloric acid (6M) and extracted twice with ethyl acetate (400 ml) and the ethyl acetate extracts combined, dried over sodium sulphate and concentrated in vacuo to a gum. Column chromatography on silica in ethyl acetate afforded crude N-tertiarybutyloxycarbonyl-L-tyrosine (4.9 g) as a colourless foam which was used directly in the next step. This acid (4.9 g) in dichloromethane (150 ml) was treated with methylamine hydrochloride (0.8 g, 25 mM), 1-hydroxybenzotriazole (2.1 g, 14 mM), dicyclohenylcarbodiimide (2.8 g, 14 mM) adjusted to pH7 with N-methylmorpholine at 0° C. and stirred continuously as the reaction was allowed to warm to 20° C. over 16 h. The reaction was filtered, washed with water, aqueous saturated sodium hydrogen carbonate and aqueous citric acid (1M), dried over sodium sulphate and concentrated in vacuo to a gum. Column chromatography on silica in ethyl acetate/hexane 1:1 afforded N-tertiarybutyloxycarbonyl-O-6(methylheptyl)-L-tyrosine-N-methyl amide which crystallised from ethyl acetate as needles m.p. 103°–106° C. (Found: C,67.5; H,9.5; N,.9. $C_{23}H_{38}N_2O_4$ requires: C,68.0; H,9.4; N,6.9%); δ (CDCl$_3$) 0.88 (6H,d,J=6 Hz, (CH$_3$)$_2$C); 1.12–1.86 (9H,m,(CH$_2$)$_4$CH); 1.4 (9H,s,(CH$_3$)$_3$C); 2.72 (3H,d,J=4 Hz, CH$_3$NH); 2.98 (2H,m,CH$_2$C$_6$H$_4$); 3.9 (2H,t,J=6 Hz,O—CH$_2$); 4.2 (1H,m,NHC$\underline{H}$CO); 5.04 (1H,m,NH); 5.72 (1H,m,NH); 6.78, and 7.2$\overline{6}$ (each 2H,each d,each J=9 Hz,C$_6$H$_4$).

EXAMPLE 32

(a) N-[3-N-(Benzyloxycarbonyl)amino-1-(R)-carboxypropyl]-L-leucyl-O-benzyl-L-tyrosine N-Methylamide To a stirred solution of the ester from example (0.36 g) in methanol (10 ml) was added dilute sodium hydroxide (1 ml, 1M). After stirring for 48 h at room temperature the reaction mixture was neutralised with acetic acid and the product was filtered off. Recrystallisation from methanol/water gave the title compound as a solid (159 mg); m.p. 172°–175°; (Found: C, 65.70; H, 6.91; N, 8.40. $C_{35}H_{44}N_4O_7.0.5H_2O$ requires C, 65.50; H, 7.06; N, 8.73%); δ (d$^6$DMSO) 0.80 (6H, m, CH($\underline{CH_3}$)$_2$); 1.0–1.35 and 1.44–1.84 (together 5H, NHCH$_2$CH$_2$, CH$_2$CH(CH$_3$)$_2$); 2.4–3.5 (9H, NHCH$_2$CH$_2$CHCO$_2$H, α-C$\overline{H}$, CH$_2$Tyr, CONHCH$_3$); 4.43 ($\overline{1H}$, m, α-C$\overline{H}$); 5.02 (2H, s, C$\underline{H_2}$C$_6$H$_5$); 6.87 ($\overline{2H}$, d, J=8 Hz, Tyr); 7.11 (2H, d, J=8 Hz, Tyr); 7.2–7.6 (11H, m, C$_6$H$_5$×2, CONH); 7.86 (1H, m, CONH); 8.16 (1H, d, J=8 Hz, CONH).

(b) N-[3-N-(Benzyloxycarbonyl)amino-1-(R)-methoxycarbonylpropyl]-L-leucyl-O-benzyl-L-tyrosine N-Methylamide To a cold (0°) solution of N-[3-N-(Benzyloxycarbonyl)amino-1-(R)-methoxycarbonylpropyl]-L-leucine (418 mg, 1 mM) in dichloromethane (50 ml) was added N-methylmorpholine (0.1 g), 1-hydroxybenzotriazole (153 mg, 1 mM) and dicyclohexylcarbodiimide (206 mg, 1 mM). After stirring for 15 minutes at 0° O-benzyl L-tyrosine N-Methylamide hydrochloride (321 mg, 1 mM) and N-methylmorpholine (0.1 g) were added. The reaction mixture after stirring and warming to room temperature over 4.5 h was filtered and washed with water. 3N citric acid, saturated aqueous sodium bicarbonate solution and water. The organic extract was dried and concentrated in vacuo to an oil. Column chromatography on silica eluting with 1:1 ethyl acetate/hexane in an increasing ethyl acetate gradient then gave the title compound as a foam (0.37 g); (Found: [m+1]$^+$=647.3417. $C_{36}H_{46}N_4O_7$ requires 647.3445); δ (CDCl$_3$) 0.88 (6H, m, CH($\underline{CH_3}$)$_2$); 1.05–2.2 (6H, m, NHCH$_2$CH$_2$, CH$_2$CH(CH$_3$)$_2$; 2.74 (3H, d, J=5 Hz, CONHC$\underline{H_3}$); 2.96–3.44 (6H, m, NHCH$_2$CH$_2$CHCO$_2$, α-CH, C$\overline{H_2}$Tyr); 3.66 (3H, s, OCH$_3$); 4.$\overline{60}$ (1H, $\overline{dd}$, J=7 and 15 Hz, α-CH); 5.02 (2H, s, C$\underline{H_2}$C$_6$H$_5$); 5.09 (2H, s, C$\underline{H_2}$C$_6$H$_5$); 6.56 (1H, br, CONH); 6.90 (2H, d, J=8 Hz, $\overline{Tyr}$); 7.12 (2H, d, J=8 Hz, Tyr); 7.25–7.6 (12H, m, CONH×2, C$_6$H$_5$×2).

O-benzyl-L-tyrosine N-Methylamide hydrochloride used in this preparation was synthesised as follows:

N-tertiarybutoxycarbonyl-O-benzyl-L-tyrosine N-methylamide (3 g) was added to a mixture of TFA and CH$_2$Cl$_2$ (1:1 100 ml) at room temperature. After 15 minutes volatiles were removed in vacuo and the residue was dissolved in water. Neutralisation with solid sodium bicarbonate, extraction into CH$_2$Cl$_2$ and evaporation of the organic extract in vacuo then gave a solid. Co-evaporation of this with ethereal HCl gave O-benzyl-L-tyrosine N-Methylamide hydrochloride.

(c) N-Tertiarybutoxycarbonyl-O-benzyl-L-tyrosine N-methylamide

To a solution of N-tertiarybutoxycarbonyl-O-benzyl-L-tyrosine (7.4 g, 20 mM), 1-hydroxybenzotriazole (3 g, 20 mM), methylamine HCl (1.3 g, 20 mM) and N-methylmorpholine (2 g, 20 mM) in CH$_2$Cl$_2$ (20 ml) stirred and cooled to 0° was added DCC (4.2 g, 20 mM). After being allowed to stir and warm to room temperature overnight the reaction mixture was filtered and washed with saturated aqueous sodium bicarbonate solution, 3N citric acid and brine. The dried organic extract was then concentrated in vacuo to give N-tertiarybutoxycarbonyl-O-benzyl-L-tyrosine N-methylamide as a solid. Recrystallisation from dichloromethane/hexane gave (4.5 g); m.p. 165°–172°; (Found: C, 68.85; H, 7.43; N, 7.39. $C_{22}H_{28}N_2O_4$ requires C, 68.73; H, 7.34; N, 7.29%); δ (CDCl$_3$) 1.40 (9H, s, OC(CH$_3$)$_3$); 2.73 (3H, d, J=5 Hz, CONHCH$_3$); 2.96 (2H, m, CH$_2$Tyr); 4.25 (1H, m, α-CH); 5.$\overline{03}$ (2H, s, C$\underline{H_2}$C$_6$H$_5$); 5.80 (1H, br, CONH); 6.86 (2H, d, J=8 Hz, $\overline{Tyr}$); 7.12 (2H, d, J=8 Hz, Tyr); 7.3–7.5 (5H, m, C$_6$H$_5$).

EXAMPLE 33

(a) N-[3-N-(Benzyloxycarbonyl)amino-1-(R)-carboxypropyl]-L-leucyl-O-cyclopentyl-L-tyrosine N-Methylamide To a solution of N-[3-N-(Benzyloxycarbonyl)amino-1-(R)-methoxycarbonylpropyl]-L-Leucyl-O-cyclopentyl-L-tyrosine N-Methylamide (536 mg, 0.86 mM) in methanol (10 ml) was added dilute sodium hydroxide (1.8 ml, 1M). After stirring for 24 h at room temperature the reaction mixture was filtered, neutralised with acetic acid and concentrated in vacuo to a solid. Purification from ethyl acetate/water gave the title compound as a solid (245 mg); m.p. 160°–170°; (Found: C, 64.36; H, 7.71; N, 9.18. $C_{33}H_{46}N_4O_7+0.25H_2O$ requires C, 64.42; H, 7.62; N, 9.11); δ (d$^6$DMSO) 0.8 (6H, M, CH(CH$_3$)$_2$); 1.17 (2H, m, CH$_2$CH(C$_3$)); 1.45–2.0 (11H, m, NHCH$_2$CH$_2$, CH$_2$CH(C$\overline{H_3}$)$_2$, CH-alkyl); 2.58 (3H, d, J=5 Hz, CONHC$\underline{H_3}$); 2.6–3.65 (6H, M, NHCH$_2$CH$_2$CHCO$_2$H, α-CH, CH$_2$C$_6$H$_4$); 4.42 (1H, q, J=7 and 15 Hz, α-CH); 4.73 (1H, m, O-CH(cyclopentyl)); 5.02 (2H, s, CH$_2$C$_6$H$_5$); 6.77 (2H, d, J=8 Hz, C$_6$H$_4$); 7.08 (2H, d, J=8 Hz, C$_6$H$_4$); 7.25 (1H, br, CONH); 7.35 (5H, s, C$_6$H$_5$); 7.85 (1H, br, CONH); 8.15 (1H, d, J=Hz, CONH).

The preceeding ester was synthesised as described below:

(b) N-[3-N-(Benzyloxycarbonyl)amino-1-(R)-methoxycarbonylpropyl]-L-leucyl-O-cyclopentyl-L-tyrosine N-Methylamide To a solution of N-[3-N-(Benzyoxycarbonyl)amino-1-(R)-methoxycarbonylpropyl]-L-leucine (418 mg, 1 mM) in dichloromethane (10 ml) was added N-methylmorpholine (106 mg, 1 mM) and the solution was stirred and cooled to 0°. 1-hydroxybenzotriazole (161 mg, 1.05 mM), N-ethyl-N'-(3-dimethylaminopropyl)carbodiimide hydrochloride (202 mg, 1.05 mM) and N-methylmorpholine (106 mg, 1 mM) were then added. After 15 minutes a solution of O-cyclopentyl-L-tyrosine N-methylamide (1.1 mM) in dichloromethane (5 ml) (which had been prepared by treatment of the N-tertiarybutoxycarbonyl precursor with trifluoroacetic acid and subsequent neutralisation with N-methylmorpholine) was added. The reaction after being allowed to stir and warm to room temperature overnight was diluted with dichloromethane (30 ml), washed with water, saturated aqueous sodium bicarbonate and water. The dried organic extract was concentrated in vacuo to give the title compound as an oil (0.55 g); (Found: [m+1]$^+$ =625.3608. C$_{34}$H$_{49}$N$_4$O$_7$ requires 625.3601); δ (CDCl$_3$) 0.82 (6H, m, CH(CH$_3$)$_2$); 1.0-2.0 (11H, m, CH$_2$CH(CH$_3$)$_2$, CH-cyclopentyl); 2.7(3H, d, J=Hz, CONHCH$_3$); 2.9-3.5 (6H, m, NHCH$_2$CH$_2$CHCO$_2$H,α-CH, CH$_2$Tyr); 3.65 (3H, s, OCH$_3$); 4.58 (1H, dd, J=7 and 15 Hz, α-CH); 4.68 (1H, br, ?); 5.08 (2H, s, CH$_2$C$_6$H$_5$); 5.22 (1H, br, CONH); 6.68 (1H, br, CONH); 6.78 (2H, d, J=8 Hz, Tyr); 7.10 (2H, d, J=8 Hz, Tyr); 7.32 (5H, s, C$_6$H$_5$); 7.52 (1H, d, J=8 Hz, CONH).

The N-(Tertiarybutoxycarbonyl)-O-cyclopentyl-L-tyrosine N-Methylamide used in this preparation was prepared as follows:

(c) N-(Tertiarybutoxycarbonyl)-O-cyclopentyl-L-tyrosine N-Methylamide

To a cold (0°) solution of N-(Tertiarybutoxycarbonyl)-O-cyclopentyl-L-tyrosine (6.89 g, 20 mM) in dichloromethane (40 ml) was added 1-hydroxybenzotriazole (3.32 g, 21 mM) and dicyclohenylcarbodiimide (4.47 g, 21 mM). After 20 minutes at 0° a solution of methylamine (1.34 g, 40 mM) in dichloromethane (20 ml) was added and the reaction mixture was allowed to stir and warm to room temperature overnight. The reaction mixture after filtration and washing with water, dilute (1M) sodium hydroxide, 3N citric acid and water was dried and concentrated in vacuo to an oil. Recrystallisation from ethyl acetate/hexane gave the title compound as white crystals (1 g); m.p. 152°-154°; (Found: C, 66.77; H, 8.47; N, 7.83. C$_{20}$H$_{30}$N$_2$O$_4$ requires C, 66.27; H, 8.34; N, 7.73%); δ(CDCl$_3$) 1.40 (9H, s, C(CH$_3$)$_3$); 1.5-2.0 (8H, CH-cyclopentyl); 2.72 (3H, d, J=5 Hz, CONHCH$_3$); 2.95 (2H, m, CH$_2$Tyr); 4.22 (1H, dd, J=7 and 15 Hz,α-CH); 4.72 (1H, br, O—CH (cyclopentyl)); 5.07 (1H, br, CONH); 5.75 (1H, br, CONH); 6.78 (2H, d, J=8 Hz, C$_6$H$_4$); 7.10 (2H, d, J=8 Hz, C$_6$H$_4$).

The N-(Tertiarybutoxycarbonyl)-O-cyclopentyl-L-tyrosine used in this preparation was prepared as follows:

(d) N-(Tertiarybutoxycarbonyl)-O-cyclopentyl-L-tyrosine

To a cold (10°) stirred solution of N-tertiarybutoxycarbonyl-L-tyrosine (11.25 g, 40 mM) in dry DMF (150 ml) under argon was added sodium hydride (2.76 g, 80% dispersion in oil, 92 mM). After one hour at 10° cyclopentyl bromide (5.96 g, 40 mM) was added and the reaction was allowed to warm and stir to room temperature overnight. Water (200 ml) and dichloromethane (300 ml) were then added and the aqueous layer was separated. The separated aqueous layer was washed with dichloromethane, acidified with hydrochloric acid and re-extracted with dichloromethane (300 ml×2). These latter dichloromethane extracts were dried and concentrated in vacuo to an oil. Column chromatography of this material on silica eluting with ethyl acetate gave the title compound as a foam (7.05 g). This was used directly in the next step without further purification.

EXAMPLE 34

(a) N-[3-N-(Benzyloxycarbonyl)amino-1-(R)-carboxypropyl]-L-leucyl-O-(2-aminobutyl-2-oxo)ethyl-L-tyrosine N-Methylamide To a solution of N-[3-N-(Benzyloxycarbonyl)amino-1-(R)-methoxycarbonylpropyl]-L-leucyl-O-(2-aminobutyl-2-oxo)ethyl-L-tyrosine N-Methylamide (199 mg, 0.3 mM) in methanol (10 ml) was added dilute sodium hydroxide (0.5 ml, 1M). After stirring for 90 h at room temperature the reaction mixture was neutralised with acetic acid and concentrated in vacuo. Purification from ethyl acetate/water gave the title compound as a solid (143 mg); m.p. 164°-170°; (Found: C, 59.44; H, 7.39; N, 10.49 C$_{34}$H$_{49}$N$_5$O$_8$+1.5H$_2$O requires C, 59.81; H, 7.68; N, 10.26%); δ(d$^6$ DMSO) 0.7-1.0 (9H, m, CH$_2$CH$_3$, CH(CH$_3$)$_2$); 1.2-2.0 (9H, m, NHCH$_2$CH$_2$, NHCH$_2$(CH$_2$)$_2$CH$_3$, CH$_2$CH(CH$_3$)); 2.62-3.64 (9H, m, NHCH$_2$CH$_2$CHCO$_2$H, CH, CH$_2$Tyr, CONHCH$_3$); 4.64 (2H, s, OCH$_2$CO); 4.56 (1H, m,α-CH); 5.07 (2H, s, CH$_2$C$_6$H$_5$); 6.90 (2H, d, J=8 Hz, Tyr); 7.17 (2H, d, J=8 Hz, Tyr); 7.34 (5H, br s, C$_6$H$_5$).

(b) N-[3-N-(Benzyloxycarbonyl)amino-1-(R)-methoxycarbonylpropyl]-L-leucyl-O-(2-aminobutyl-2-oxo)ethyl-L-tyrosine N-Methylamide To a cold (0°) stirred solution of N-[3-N-(Benzyloxycarbonyl)amino-1-(R)-methoxycarbonylpropyl]-L-leucine HCl in CH$_2$Cl$_2$/DMF (11 ml, 10:1) was added N-methylmorpholine (240 mg, 2.4 mM), 1-hydroxybenzotriazole (180 mg, 1.2 mM) and N-ethyl-N'-(3-dimethylaminopropyl)carbodiimide hydrochloride (0.24 g, 1.2 mM). After stirring for 15 min. at 0° a solution of n-butylamine (90 mg, 1.2 mM) in CH$_2$Cl$_2$ was added and the reaction mixture was allowed to warm and stir to room temperature overnight. The reaction mixture after dilution with CH$_2$Cl$_2$ (30 ml) was washed (water (10 ml), 3N citric acid (10 ml) and saturated aqueous sodium bicarbonate (10 ml)), dried, filtered and concentrated in vacuo to an oil. Crystallisation from ethyl acetate/hexane then gave the title compound as a white solid (0.27 g); m.p. 101°-107°; (Found: C, 62.13; H, 7.84; N, 10.42. C$_{35}$H$_{51}$N$_5$O$_8$+0.5H$_2$O requires C, 61.93; H,7.72; N, 10.32%); δ(CDCl$_3$) 0.87 (6H, m, CH$_2$CH(CH$_3$)$_2$); 0.94 (3H, t, J=7 Hz, CH$_2$CH$_3$); 1.04-2.0 (9H, m,NHCH$_2$CH$_2$, CH$_2$CH(CH$_3$)$_2$, NHCH$_2$(CH$_2$)$_2$CH$_3$); 2.75 (3H, d, J=5 Hz, CONHCH$_3$); 2.85-3.45 (9H, M, NHCH$_2$CH$_2$CHCO$_2$H, NHCH$_2$, α-CH, CH$_2$Tyr); 3.66 (3H, s, OCH$_3$); 4.42 (2H, s, OCH$_2$CO); 4.63 (1H, dd, J=7 and 15 Hz, α-CH); 5.07 (2H, s, CH$_2$C$_6$H$_5$); 5.26

(1H, br, CONH); 6.63 (1H, br, CONH); 6.82 (2H, d, J=8 Hz, Tyr); 7.15 (2H, d, J=8 Hz, Tyr); 7.34 (5H, s, C$_6$H$_5$); 7.58 (1H, d, J=10 Hz, CONH).

EXAMPLE 35

(a) N-[3-N-(Benzyloxycarbonyl)amino-1-(R)-carboxypropyl]-L-leucyl-O-(2'-carboxyethyl-L-leucyl N-Methylamide)-L-tyrosine N-Methylamide To a solution of N-[3-N-(Benzyloxycarbonyl)amino-1-(R)-methoxycarbonylpropyl]-L-leucyl-O-(2'-carboxyethyl-L-leucyl N-Methylamide)-L-tyrosine N-Methylamide (300 mg, 0.4 mM) in methanol (10 ml) was added dilute sodium hydroxide (1.2 ml, 0.5M). After stirring for 48 h at room temperature the reaction mixture was neutralised with acetic acid and concentrated in vacuo. Recrystallisation from methanol/water gave the title compound as a solid (115 mg); m.p. 162°-163°; (Found: C, 60.26; H, 7.49; N, 11.09 C$_{37}$H$_{54}$N$_6$O$_9$+0.5-H$_2$O requires C, 60.39; H, 7.53; N, 11.42%); δ(d$^6$DMSO) 0.7–0.9 (12H, m, CH(CH$_3$)$_2$×2); 0.95–1.85(8H, m, CH$_2$CH(CH$_3$)×2, NHCH$_2$CH$_2$); 2.45–3.7 (13H, m, NHCH$_2$CH$_2$CHCO$_2$H, CONHCH$_3$×2, α-CH×2, CH$_2$Tyr); 4.34 (1H, m, —CH); 4.46 (2H, s, OCH$_2$CO); 5.05 (2H, s, CH$_2$C$_6$H$_5$); 6.82 (2H, d, J=8 Hz, Tyr); 7.13 (2H, d, J=8 Hz, Tyr); 7.24 (1H, br, CONH); 7.35 (5H, s, C$_6$H$_5$); 7.85 (1H, br, CONH); 7.98 (2H, br, CONH×2); 8.15 (1H, d, J=10 Hz, CONH).

The ester required in this preparation was prepared as follows:

(b) N-[3-N-(Benzyloxycarbonyl)amino-1-(R)-methoxycarbonylpropyl]-L-leucyl-O-(2'-carboxyethyl-L-leucyl N-Methylamide)-L-tyrosine N-Methylamide To a cold (0°) solution of N-[3-N-(Benzyloxycarbonyl)amino-1-(R)-methoxycarbonylpropyl]-L-leucyl-O-(2'-carboxyethyl)-L-tyrosine N-Methylamide (0.6 g, 1.1 mM) in CH$_2$Cl$_2$/DMF (11 ml 10:1) was added 1-hydroxybenzotriazole (0.18 g, 1.2 mM), N-ethyl-N'-(3-dimethylaminopropyl)carbodiimide hydrochloride (0.24 g, 1.2 mM) and N-methylmorpholine (0.24 g, 2.4 mM). After 5 min. at 0° L-leucine N-methylamide HCl (0.22 g, 1.2 mM) and N-methylmorpholine (120 mg, 1.2 mM) were added and the reaction was allowed to stir and warm to room temperature overnight. The reaction mixture after diluting with CH$_2$Cl$_2$ (30 ml) was washed with water (20 ml), 3N citric acid (30 ml) and saturated aqueous sodium bicarbonate solution. The organic extract was dried and concentrated in vacuo to an oil. Recrystallisation from ethyl acetate/hexane gave the title compound as crystals (350 mg); m.p. 122°-123°; (Found: C,61.16; H,7.45; N,11.14. C$_{38}$H$_{56}$N$_6$O$_9$ requires C,61.60; H,7.62; N,11.34%); δ(CDCl$_3$) 0.8–1.0 (12H, m, CH(CH$_3$)$_2$×2); 1.05–2.05 (8H,m, CH$_2$CH(CH$_3$)$_2$×2, NHCH$_2$CH$_2$); 2.75 (3H, d, J=5 Hz, CONHCH$_3$); 2.80 (3H, d, J=5 Hz, CONHCH$_3$); 2.8–3.5 (7H, m,NHCH$_2$CH$_2$CHCO$_2$, CH$_2$Tyr, α-CH×2); 3.68 (3H, s, OCH$_3$); 4.44 (2H, s,OCH$_2$CO); 4.4–4.7 (2H, m,α-CH×2); 5.10 (2H, s, CH$_2$C$_6$H$_5$); 5.34 (1H, t,J=6 Hz, CONH); 6.42 (1H, br, CONH); 6.73 (1H, br, CONH); 6.82 (2H, d, J=8 Hz, Tyr); 7.0 (1H, br, CONH); 7.15 (2H, d, J=8 Hz, Tyr), 7.36 (5H, s, C$_6$H$_5$); 7.56 (1H, br, CONH).

EXAMPLE 36

(a) N-[3-N-(Benzyloxycarbonyl)amino-1-(R)-carboxypropyl]-L-leucyl-O-methyl-L-tyrosine N-Phenethylamide To a solution of N-[3-(Benzyloxycarbonyl)amino-1-(R)-methoxycarbonylpropyl]-L-leucyl-O-methyl-L-tyrosine N-Phenethylamide (210 mg, 0.33 mM) in methanol (5 ml) was added dilute sodium hydroxide (0.5 ml, 1M). After stirring for 5 h at room temperature the reaction mixture was concentrated in vacuo and diluted with water. The aqueous extract after washing with ether was acidified to pH 3 with dilute (1N) HCl. The resulting solid was filtered and dried to give the title compound as a solid (110 mg); (Found: C, 65.5; H,7.0; N, 9.1. 0.05H$_2$O requires C, 65.5; H, 7.0; N, 8.7%).

(b) N-[3-N-(Benzyloxycarbonyl)amino-1-(R)-methoxycarbonylpropyl]-L-leucyl-O-methyl-L-tyrosine N-Phenethylamide To a cold (0°) solution of N-[3-N-(Benzyloxycarbonyl)amino-1-(R)-methoxycarbonylpropyl]-L-leucyl-O-methyl-L-tyrosine Hydrochloride (400 mg, 0.67 mM) in DMF was added N-methylmorpholine (68 mg, 0.67 mM), 1-hydroxybenzotriazole (107 mg, 0.7 mM) and benzylamine (72 mg, 0.67 mM). The reaction mixture was then cooled to −10° and N-ethyl-N'-(3-dimethylaminopropyl)carbodiimide hydrochloride (134 mg, 0.7 mM) and N-methylmorpholine (71 mg, 0.7 mM) were added. After being allowed to warm and stir to room temperature over 20 h the reaction mixture was concentrated in vacuo. The resultant residue after dissolving in CH$_2$Cl$_2$ and washing (water, saturated aqueous sodium bicarbonate solution) was concentrated in vacuo. Recrystallisation from ethyl acetate/hexane gave the title compound (290 mg); (Found: C, 66.9; H, 7.1; N, 8.7. required C, 67.2; H, 7.3; N, 8.6%); δ(CDCl$_3$) 0.86 (6H, M, CH(CH$_3$)$_2$); 1.1–1.9 (6H, m, NHCH$_2$CH$_2$, CH$_2$CH(CH$_3$)$_2$); 2.95–3.42 (6H, m, NHCH$_2$CH$_2$CHCO$_2$CH$_3$,α-CH, CH$_2$Tyr); 3.45 (3H, s, OCH$_3$); 3.73 (3H, s, OCH$_3$); 4.38 (2H, m, CH$_2$C$_6$H$_5$); 4.65 (1H, q, J=7 and 15 Hz, α-CH); 5.04 (1H, br, CONH); 5.08 (2H, s, CH$_2$C$_6$H$_5$); 6.78 (2H, d, J=8 Hz, Tyr); 6.96 (1H, br, CONH); 7.11 (2H, d, J=8 Hz, Tyr); 7.10–7.30 (5H, m, C$_6$H$_5$); 7.34 (5H, s, C$_6$H$_5$); 7.54 (1H, d, J=8 Hz, CONH).

The starting material for this reaction was prepared as follows:

(c) N-[3-N-(Benzyloxycarbonyl)amino-1-(R)-methoxycarbonylpropyl]-L-leucyl-O-methyl-L-tyrosine N-[3-N-(Benzyloxycarbonyl)amino-1-(R)-methoxy carbonylpropyl]-L-leucyl-O-methyl-L-tyrosine t-butyl ester (3 g) was dissolved in TFA (30 ml) and water (1.5 ml). After 4 h at room temperature volatiles were removed in vacuo and the residue was co-evaporated twice with toluene. Trituation of the resulting solid with ethereal HCl then gave N-[3-N-(Benzyloxycarbonyl)amino-1-(R)-methoxycarbonylpropyl]-L-leucyl-O-methyl-L-tyrosine as its hydrochloride salt.

(d) N-[3-N-(Benzyloxycarbonyl)amino-1-(R)-methoxycarbonylpropyl]-L-leucyl-O-methyl-L-tyrosine 'Butyl ester A solution of methyl 4-N-(benzyloxycarbonyl)amino-2-bromo-butanoate (2.5 g, 7.5 mM), L-leucyl-O-methyl-L-tyrosine t-butyl ester (1.82 g, 5 mM), (which had been prepared by hydrogenolysis of the N-benzloxycarbonyl precursor in the usual manner), and N-methylmorpholine (0.76 g, 7.5 mM) in acetonitrile (15 ml) was heated under reflux for 30 h. The reaction mixture was then concentrated in vacuo, dissolved in CH$_2$Cl$_2$, washed (water, 3N citric acid and saturated aqueous sodium bicarbonate solution), dried and evaporated in vacuo to yield an oil. Column chromatography on silica eluting with 40:60 ethyl acetate/hexane gave the title compound as an oil (670 mg); δ(CDCl$_3$) 0.88 (6H, dd, J=7 Hz, CH(CH$_3$)$_2$); 1.42 (9H, s, OC(CH$_3$)$_3$); 1.62 (3H, m, CH$_2$CH(CH$_3$)$_2$); 1.86 (2H, m, NHCH$_2$CH$_2$); 2.9–3.36 (6H, m, NHCH$_2$CH$_2$CHCO$_2$CH$_3$,α-CH, CH$_2$Tyr); 3.66 (3H, s, OCH$_3$); 3.78 (3H, s, OCH$_3$); 4.68 (1H, dd, J=7 and 15 Hz,α-CH); 5.09 (2H, s, CH$_2$C$_6$H$_5$); 5.16 (1H, br, CONH); 6.80 (2H, d, J=8 Hz, Tyr); 7.01 (1H, br, CONH); 7.07 (2H, d, J=8 HZ, Tyr); 7.35 (5H, s, C$_6$H$_5$).

The N-(benzyloxycarbonyl)-L-leucyl-O-methyl-L-tyrosine t-butyl ester used in this preparation was prepared as follows:

(e) N-(Benzyloxycarbonyl)-L-leucyl-O-methyl-L-tyrosine 'Butyl ester

To a cold (0°) solution of N-tertiarybutoxycarbonyl-L-leucine (4 g, 15.1 mM), O-methyl-L-tyrosine t-butyl ester (3.8 g, 15.1 mM) and 1-hydroxybenzotriazole (2.43 g, 15.9 mM) in DMF (30 ml) was added N-methylmorpholine (1.61 g, 15.9 mM) and N-ethyl-N'-(3-dimethylaminopropyl)carbodiimide hydrochloride (3.04 g, 15.9 mM). After stirring at 0° for 1 h the solution was allowed to warm to room temperature overnight. The reaction mixture was then concentrated in vacuo, dissolved in ethyl acetate, washed (water, 0.5 mole citric acid, brine, saturated aqueous sodium bicarbonate solution and brine), dried and evaporated in vacuo to give an oil. Chromatography on silica eluting with 25% ethyl acetate in hexane then gave the title compound as a foam (4.65 g); (Found: [m+1]$^+$=499.2803. C$_{28}$H$_{39}$N$_2$O$_6$ requires 499.2808); δ(CDCl$_3$) 0.92 (6H, m, CH(CH$_3$)$_3$); 1.42 (9H, s, OC(CH$_3$)$_3$); 1.4–1.83 (3H, m, CH$_2$CH(CH$_3$)$_2$); 3.03 (2H, m, CH$_2$Tyr); 3.76 (3H, s, OCH$_3$); 4.18 (1H, m,α-CH); 4.69 (1H, dd, J=7 and 15 Hz,α-CH); 5.12 (2H, s, CH$_2$C$_6$H$_5$); 5.17 (1H, m, CONH); 6.43 (1H, m, CONH); 6.79 (2H, d, J=8 Hz, Tyr); 7.06 (2H, d, J=8 Hz, Tyr); 7.36 (5H, s, C$_6$H$_5$).

The O-methyl-L-tyrosine t-butyl ester used in this synthesis was prepared as follows:

(f) O-methyl-L-tyrosine t-butyl ester

To a cold, (−5°), stirred solution of N-benzyloxycarbonyl-O-methyl-L-tyrosine (6.58 g, 20 mM) in t-butanol/pyridine (70 ml, 5:2) was added phosphorus oxychloride (3.35 g, 22 mM) dropwise over 0.5 h. After a further 0.5 h at −5° the reaction was warmed to room temperature and was then left to stir overnight. The reaction mixture, after diluting with ethyl acetate and washing (0.5M citric acid, brine, saturated aqueous sodium bicarbonate solution and brine) was concentrated in vacuo to give the required t-butyl ester (7.54 g). To a portion of this (7.4 g, 19.2 mM) in methanol (100 ml) was added 10% Pd/C (1 g) and acetic acid (1.16 g, 19.2 mM). After stirring the reaction mixture under hydrogen at room temperature for 4 h it was filtered and evaporated in vacuo. The residue was then taken up in dichlromethane and saturated aqueous sodium bicarbonate solution and the organic phase was separated, washed with brine, dried and evaporated in vacuo to yield O-methyl-L-tyrosine t-butyl ester as a solid (3.95 g).

The compounds of Examples 37 to 143 and their routes of preparation are exemplified within the following Tables.

Using the methods illustrated in examples 1–24 further examples 37–143 in Table 1 are prepared.

Compounds N-[2-(S)-N-(1-(R)-carboxyethyl)amino-4,4-di-(trifluoromethyl)butanoyl]-O-methyl-L-tyrosine N-methylamide and N-[2-(S)-N-(3-(benzyloxycarbonyl)amino-1-(R)-carboxypropyl)amino-4,4-di-(trifluoromethyl)butanoyl]-O-methyl-L-tyrosine N-methylamide are likewise prepared by methods described in examples 1–24.

TABLE 1

| No | PROCESS | A | A¹ | Y | n | R² | R³ | A³ | STEREO-CHEM¹ | MP. °C² R¹ = OCH₃ | MP. °C² R¹ = OH |
|---|---|---|---|---|---|---|---|---|---|---|---|
| 37 | 1A | — | H | — | 1 | H | CH(CH₃)CH₂CH₃ | GlyNHC₄H₉n | RS | 82-84 | 74-77 |
| 38 | 1A | — | H | — | 1 | H | CH₂CH(CH₃)₂ | GlyNHC₄H₉n | RS | | 87-95 |
| 39 | 1A | — | H | — | 1 | H | CH₂CH(CH₃)₂ | GlyNHC₄H₉n | SS | | 175-180 |
| 40 | 1A | — | H | — | 1 | H | CH₂CH(CH₃)₂ | ValNHC₆H₁₃n | RSS | | 190-193 |
| 41 | 1A | — | H | — | 1 | H | CH₂CH(CH₃)₂ | ValNHC₆H₁₃n | SSS | | 200-203 |
| 42 | 1A | — | H | — | 1 | H | CH₂CH(CH₃)₂ | LeuNHC₄H₉n | RSS | 138-139 | 180-185 |
| 43 | 1A | — | H | — | 1 | H | CH₂CH(CH₃)₂ | LeuNHC₄H₉n | SSS | 180-185 | 183-185 |
| 44 | 1A | — | H | — | 1 | H | CH₂CH(CH₃)₂ | LeuNHC₄H₉n | RSR | 103-107 | 150-160 |
| 45 | 1A | — | H | — | 1 | H | CH₂CH(CH₃)₂ | LeuNHC₄H₉n | SSR | 94-98 | 185-188 |
| 46 | 1A | — | H | — | 1 | H | CH₂CH(CH₃)₂ | Thr(OBZ)NHC₄H₉n | RSSR | 62-67 | 145-148 |
| 47 | 1A | — | H | — | 1 | H | CH₂CH(CH₃)₂ | Thr(OBZ)NHC₄H₉n | SSSR | 61-64 | 147-152 |
| 48 | 1A | — | H | — | 1 | H | CH₂CH(CH₃)₂ | ValGlyOCH₃ | RS | | 87-92 |
| 49 | 1A | — | H | — | 3 | H | CH₂CH(CH₃)₂ | ValGlyOCH₃ | SS | | 177-180 |
| 50 | 1A | — | H | — | 3 | H | CH₂CH(CH₃)₂ | ValGlyOCH₃ | RS | | |
| 51 | 1A | — | H | — | 1 | H | CH₂CH(CH₃)₂ | Thr(OBZ)NHCH₃ | RSSR | 72-76 | 194-197 |
| 52 | 1A | — | H | — | 1 | H | CH₂CH(CH₃)₂ | Thr(OBZ)NH(CH₂)₂—SCH₂CH₃ | RSSR | 162-164³ | 105-109 |
| 53 | 1A | — | H | — | 1 | H | CH₂CH(CH₃)₂ | Thr(OBZ)NH(CH₂)₂—SOCH₂CH₃ | RSSR | | 80-85 |
| 54 | 1A | — | H | — | 1 | H | CH₂CH(CH₃)₂ | Thr(OBZ)NH(CH₂)₃—CONH₂ | RSSR | 97 | 193 |
| 55 | 1A | — | H | — | 1 | H | CH₂CH(CH₃)₂ | Thr(OBZ)NH(CH₂)₅—CONH₂ | RSSR | foam | 115-120 |
| 56 | 1A | — | H | — | 1 | H | CH₂CH(CH₃)₂ | Thr(OBZ)N(CH₃)—C₄H₉n | RSSR | oil | 56-57 |
| 57 | 1A | — | H | — | 1 | H | CH₂CH(CH₃)₂ | Thr(OBZ)NH(CH₂)₂—SO₂CH₂CH₃ | RSSR | 157-161³ | 90-95 |
| 58 | 1A | — | H | — | 1 | H | CH₂CH(CH₃)₂ | Thr(OBZ)NH(CH₂)₅—CO₂H | RSSR | 131-133³ | 105-107 |
| 59 | 1A | — | H | — | 1 | H | CH₂CH(CH₃)₂ | NHCH(CONHCH₃)CH₂—NHCO₂C(CH₃)₃ | RSS | 107-112 | 174-182 |
| 60 | 1A | — | H | — | 1 | H | CH₂CH(CH₃)₂ | Ser(OBZ)NHCH₃ | RS | 61-64 | 188-190 |
| 61 | 1A | — | H | — | 1 | H | CH₂CH(CH₃)₂ | TyrNHCH₃ | RS | | 212-217 |
| 62 | 1A | — | H | — | 2 | H | CH₂CH(CH₃)₂ | NHCH(CONHCH₃)CH₂—NHCOPh | RSS | 71-74 | 186-191 |
| 63 | 1A | — | H | — | 6 | H | CH₂CH(CH₃)₂ | NHCH(CONHCH₃)₂—NHZ | RSS | 110-112 | 163-166 |
| 64 | 1A | — | H | NH | 2 | H | CH₂CH(CH₃)₂ | ThrNH(CH₂)₃CONH₂ | RSSR | 174-176³ | 235 |
| 65 | 1A | — | H | NH | 1 | H | CH₂CH(CH₃)₂ | AlaNHC₄H₉n | RSS | | 158-162 |
| 66 | 1A | Z | Z | — | 2 | H | CH₂CH(CH₃)₂ | AlaNHCH₃ | SSS | | 176-182 |
| 67 | 1A | Z | Z | — | 6 | H | CH₂CH(CH₃)₂ | AlaNHCH₃ | RSS | | 166-168 |
| 68 | 1A | Z | Z | — | 2 | H | CH₂CH(CH₃)₂ | Thr(OBZ)NHCH₃ | SSSR | 62-64 | 112-120 |
| 69 | 1A | — | H | — | 6 | H | CH₂CH(CH₃)₂ | Thr(OBZ)NHCH₃ | RSSR | 79-80 | 63-66 |
| 70 | 1A | Z | Z | NH | 2 | H | CH₂CH(CH₃)₂ | Thr(OBZ)NHCH₃ | RSSR | 92-94 | 160-164 |
| 71 | 1A | — | H | — | 1 | H | CH₂CH(CH₃)₂ | AlaNHCH₃ | RSS | 87-90 | 84-88 |
| 72 | 1A | — | H | — | 1 | H | CH₂CH(CH₃)₂ | PheNHCH₃ | RSS | 116-119 | 115-116 |
| 73 | 1A | — | H | — | 1 | H | CH₂CH(CH₃)₂ | SarNHCH₃ | RS | 160-175 | 77-80 |
| 74 | 1A | Z | Leu | — | 2 | H | CH₂CH(CH₃)₂ | ProNHCH₃ | RSS | 99-102 | 100-105 |
| 75 | 1A | — | H | — | 1 | H | CH₂CH(CH₃)₂ | NHCH(CONHCH₃)—(CH₂)₆CH₃ | RS(RS) | 155-159³ | 186-191 |
| 76 | 1A | — | H | — | 1 | H | CH₂CH(CH₃)₂ | N—CH₃—Tyr(OBZ)—NHCH₃ | RS | 115-120³ | 115-121 |
| 77 | 1A | — | H | — | 1 | H | CH₂CH(CH₃)₂ | iso-AbaNHCH₃ | RS | 150-153³ | 177-179 |
| 78 | 1A | — | H | — | 1 | H | CH₂CH(CH₃)₂ | N—Z—LysNHCH₃ | RSS | 170-172³ | 162-164 |
| 79 | 1A | — | H | NH | 2 | H | CH₂CH(CH₃)₂ | Tyr(OCH₃)NHCH₃ | SRSS | | 145-150 |
| 80 | 1A | — | H | — | 1 | H | CH₂CH(CH₃)₂ | SerNHCH₃ | SSS | | 191-198 |
| 81 | 1A | — | H | NH | 2 | H | CH₂CH(CH₃)₂ | AlaNHCH₃ | SSS | | 176-182 |
| 82 | 1A | — | H | NH | 2 | H | CH₂CH(CH₃)₂ | AlaNHCH₃ | RSS | | 166-168 |
| 83 | 1B | — | CH₃CO | NH | 1 | H | CH₂CH(CH₃)₂ | Thr(OBZ)NHCH₃ | RSSR | 131-132 | 105-107 |
| 84 | 1B | — | CH₃CO | NH | 1 | H | CH₂CH(CH₃)₂ | Thr(OBZ)NHCH₃ | RRSR | 133-134 | 108-112 |
| 85 | 1B | — | (CH₃)₃COCO | NH | 1 | H | CH₂CH(CH₃)₂ | Thr(OBZ)NHCH₃ | RSSR | 95-97 | 100-102 |
| 86 | 1B | — | (CH₃)₃COCO | NH | 1 | H | CH₂CH(CH₃)₂ | Thr(OBZ)NHCH₃ | RSSR | 123-124 | 114-118 |
| 87 | 1B | — | (CH₃)₃COCO | NH | 1 | H | CH₂CH(CH₃)₂ | Thr(OBZ)NHCH₃ | RSSR | | 80-90 |

TABLE 1-continued

| No | PROCESS | A | A¹ | Y | n | R² | R³ | A³ | STEREO-CHEM¹ | MP. °C² R¹ = OCH₃ | MP. °C² R¹ = OH |
|---|---|---|---|---|---|---|---|---|---|---|---|
| 88 | 1B | DnpPro Leu | | NH | 1 | H | CH₂CH(CH₃)₂ | Thr(OBZ)NHCH₃ | SSRSSR | | 112–115 |
| 89 | 1B | DnpPro Leu | | NH | 1 | H | CH₂CH(CH₃)₂ | Thr(OBZ)NHCH₃ | SSRRSR | | 100–115 |
| 90 | 1B | — | Ph(CH₂)₂NHCO | — | 1 | H | CH₂CH(CH₃)₂ | Tyr(OCH₃)NHCH₃ | R(RS)S | 124–128 | 130–132 |
| 91 | 1B | — | HO₂C | — | 1 | H | CH₂CH(CH₃)₂ | Tyr(OCH₃)NHCH₃ | RSS | 64–66 | 193–196 |
| 92 | 2A | — | H | — | 1 | H | CH₂CH(CH₃)₂ | Tyr(OBZ)NH₂ | RSS | 117–119⁴ | 200–202 |
| 93 | 2A | — | H | — | 1 | H | CH₂CH(CH₃)₂ | Tyr(OCH₃)NH₂ | RSS | 96–97 | 100–105 |
| 94 | 2A | — | H | — | 1 | H | CH(CH₃)₂ | AlaNHC₄H₉n | SSS | 60–62 | 165–170 |
| 95 | 2A | — | H | — | 1 | H | CH(CH₃)₂ | AlaNHC₄H₉n | RSS | | 220–223 |
| 96 | 2A | — | H | — | 1 | H | CH₃ | AlaNHC₄H₉n | (RS)SS | | 231–234 |
| 97 | 2A | — | H | — | 1 | H | CH₃ | AlaNHC₄H₉n | (SR)SS | | |
| 98 | 2A | — | H | — | 1 | H | CH₂CH(CH₃)₂ | His(BZ)NHCH₃ | RSS | | 192–196 |
| 99 | 2A | — | H | — | 1 | H | CH₂CH(CH₃)₂ | AlaNHOCH₃ | RSS | 95–103 | 98–108 |
| 100 | 2A | — | H | — | 1 | H | CH₂CH(CH₃)₂ | Thr(OC₄H₉t)NHCH₃ | RSSR | | 219–230 |
| 101 | 2A | — | H | — | 1 | H | CH₂CH(CH₃)₂ | TyrNH₂ | RSS | | 199–201 |
| 102 | 2A | — | H | — | 1 | H | (CH₂)₂CH₃ | AlaNHC₄H₉n | R(RS)S | 84–85 | 150 |
| 103 | 2A | — | CH₃CO | NH | 3 | H | CH₂CH(CH₃)₂ | Tyr(OCH₃)NHCH₃ | RSS | 101–104 | 155–159 |
| 104 | 2A | — | H | — | 1 | H | (CH₂)₂SCH₃ | AlaNHC₄H₉n | RSS | foam | |
| 105 | 2A | — | H | — | 1 | H | CH₂CH(VH₃)₂ | NHCH(CH₃)CH₂Ph | RS(RS) | | 173–178 |
| 106 | 2A | — | H | — | 1 | H | CH₂C₆H₅ | AlaNHC₄H₉n | (RS)SS | | 158–162 |
| 107 | 2A | — | H | — | 1 | H | CH₂OCH₂Ph | AlaNHC₄H₉n | RSS | | 162–164 |
| 108 | 2A | — | Ph(CH₂)₂CO | NH | 2 | H | CH(CH₃)CH₂CH₃ | Tyr(OCH₃)NHCH₃ | RSS | 90–94 | 162–163 |
| 109 | 2A | — | H | — | 1 | H | —(CH₂)₅— | AlaNHC₄H₉n | (RS)S | 114–118 | 95–105 |
| 110 | 2A | — | (CH₃)₂CHCH₂CO | NH | 2 | H | CH₂CH(CH₃)₂ | Tyr(OCH₃)NHCH₃ | RSS | | 168–172 |
| 111 | 2A | — | CH₃OCO | NH | 2 | H | CH₂CH(CH₃)₂ | Tyr(OCH₃)NHCH₃ | RSS | | 149–153 |
| 112 | 2A | Z | Pro | NH | 2 | H | CH₂CH(CH₃)₂ | Tyr(OCH₃)NHCH₃ | SRSS | 102–103 | 174–179 |
| 113 | 2A | — | (CH₃)₂CHCH₂OCO | NH | 2 | H | CH₂CH(CH₃)₂ | Tyr(OCH₃)NHCH₃ | RSS | | 171–175 |
| 114 | 2A | — | PhCH=CHCO | NH | 2 | H | CH₂CH(CH₃)₂ | Tyr(OCH₃)NHCH₃ | RSS | | 188–191 |
| 115 | 2A | — | 2-Cl—C₆H₄CO | NH | 2 | H | CH₂CH(CH₃)₂ | Tyr(OCH₃)NHCH₃ | RSS | 109 | 158–163 |
| 116 | 2A | — | 4-Cl—C₆H₄CO | NH | 2 | H | CH₂CH(CH₃)₂ | Tyr(OCH₃)NHCH₃ | RSS | 105–108 | 187–192 |
| 117 | 2A | — | Z | NH | 2 | H | CH₂CH(CH₃)₂ | Tyr(OCH₃)OC₄H₉t | RSS | | 101–102 |
| 118 | 2A | — | 4-CH₃—C₆H₄CH₂—OCO | NH | 2 | H | CH₂CH(CH₃)₂ | Tyr(OCH₃)NHCH₃ | RSS | 141–143 | 164–167 |
| 119 | 2A | — | 4-Cl—C₆H₄CH₂OCO | NH | 2 | H | CH₂CH(CH₃)₂ | Tyr(OCH₃)NHCH₃ | RSS | | 167–171 |
| 120 | 2A | — | HO₂C(CH₂)₂CO | NH | 2 | H | CH₂CH(CH₃)₂ | Tyr(OCH₃)NHCH₃ | RSS | 50–55 | 160–171 |
| 121 | 2A | — | 4-CH₃—C₆H₄CO | NH | 2 | H | CH₂CH(CH₃)₂ | Tyr(OCH₃)NHCH₃ | RSS | 98 | 190–194 |
| 122 | 2A | — | PhCH₂CO | NH | 2 | H | CH₂CH(CH₃)₂ | Tyr(OCH₃)NHCH₃ | RSS | | 173–179 |
| 123 | 2A | — | 2-Cl—C₆H₄CH₂OCO | NH | 2 | H | CH₂CH(CH₃)₂ | Tyr(OCH₃)NHCH₃ | RSS | | 168–174 |
| 124 | 2A | — | 4-CH₃O—C₆H₄CH₂—OCO | NH | 2 | H | CH₂CH(CH₃)₂ | Tyr(OCH₃)NHCH₃ | RSS | | 162–166 |
| 126 | 2A | — | Bornyl-OCO | NH | 2 | H | CH₂CH(CH₃)₂ | Tyr(OCH₃)NHCH₃ | RSS | | 145–150 |
| 127 | 2A | — | 2-CH₃—C₆H₄CH₂—OCO | NH | 2 | H | CH₂CH(CH₃)₂ | Tyr(OCH₃)NHCH₃ | RSS | | 170–173 |
| 128 | 2A | — | Ph(CH₂)₂OCO | NH | 2 | H | CH₂CH(CH₃)₂ | Tyr(OCH₃)NHCH₃ | RSS | 50–60 | 147–151 |
| 129 | 2A | — | PhCH₂SO₂ | NH | 2 | H | CH₂CH(CH₃)₂ | Tyr(OCH₃)NHCH₃ | RSS | 65–70 | 174–178 |
| 130 | 2A | — | PhCH₂N(CH₃)CO | NH | 2 | H | CH₂CH(CH₃)₂ | Tyr(OCH₃)NHCH₃ | RSS | 148–153 | 90–95 |
| 131 | 2A | — | 2-NaphthylCO | NH | 2 | H | CH₂CH(CH₃)₂ | Tyr(OCH₃)NHCH₃ | RSS | 67–71 | 162–172 |
| 132 | 2A | — | 1-NaphthylCO | NH | 2 | H | CH₂CH(CH₃)₂ | Tyr(OCH₃)NHCH₃ | RSS | | 167–173 |
| 133 | 2A | — | Ph | — | 1 | H | CH₂CH(CH₃)₂ | Tyr(OCH₃)NHCH₃ | RSS | | 161–166 |
| 134 | 2A | — | 1-NaphthylCH₂—OCO | NH | 2 | H | CH₂CH(CH₃)₂ | Tyr(OCH₃)NHCH₃ | RSS | 85–86 | 182–184 |
| 135 | 2A | — | 2-NaphthylCH₂—OCO | NH | 2 | H | CH₂CH(CH₃)₂ | Tyr(OCH₃)NHCH₃ | RSS | 92–98 | 168–171 |

TABLE 1-continued

| No | PROCESS | A | A¹ | Y | n | R² | R³ | A³ | STEREO-CHEM[1] | MP. °C.[2] R¹ = OCH₃ | MP. °C.[2] R¹ = OH |
|---|---|---|---|---|---|---|---|---|---|---|---|
| 136 | 2A | — | PhC=CCO | NH | 2 | H | CH₂CH(CH₃)₂ | Tyr(OCH₃)NHCH₃ | RSS | | |
| 137 | 2A | — | H | — | 1 | H | CH₂CH(CF₃)₂ | Tyr(OCH₃)NHCH₃ | RSS | | |
| 138 | 2A | — | Z | NH | 2 | H | CH₂CH(CF₃)₂ | Tyr(OCH₃)NHCH₃ | RSS | | |
| 139 | 2A | — | Z | NH | 2 | H | CH₂CH(CH₃)₂ | Tyr(OBZ)NHCH₃ | RSS | 81–85 | |
| 140 | 2A | — | Z | NH | 2 | H | CH₂CH(CH₃)₂ | Tyr(OC₅H₁₁m)NHCH₃ | RSS | | 172–175 |
| 141 | 2A | ZPro | Leu | NH | 2 | H | CH₂CH(CH₃)₂ | Tyr(OCH₃)NHCH₃ | SSRSS | | 155–157 |
| 142 | 2A | ZPro | Pro | NH | 2 | H | CH₂CH(CH₃)₂ | Tyr(OCH₃)NHCH₃ | SSRSS | 133–135 | |
| 143 | 2B | — | HO₂C | — | 2 | H | CH₂CH(CH₃)₂ | Tyr(OCH₃)NHCH₃ | RSS | | 110–120 |

Notes for TABLE 1:
[1]Stereochemistry-optical centres labelled from left to right.
[2]Of hydrated form where appropriate.
[3]m.p. of HCl salt.
[4]R¹ = OC₂H₅ not OCH₃    Gly = glycyl = NHCH₂CO
Phe = phenylalanyl = NHCHCO
       |
       CH₂C₆H₅

16 Val = valyl = NHCHCOH₂C₆H₅
                |
                CH(CH₃)₂

Ph = phenyl = C₆H₅
Bz = CH₂C₆H₅
Z = PhCH₂O.CO
DMP = 2,4-dinitrophenyl
Leu = leucyl = NH—CHCO
                   |
                   CH₂CH(CH₃)₂
Sar = Sarcosyl = N(CH₃)CH₂CO
Thr = threonyl = NH—CHCO
                     |
                     CH(CH₃)OH Tyr = tyrosyl = NH—CHCHCO
                    |
                    CH₂
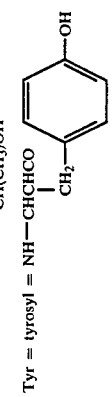

Ser = seryl = NHCHCO
                |
                CH₂OH

Pro = prolyl = N 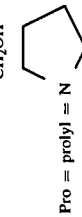

Lys = lysyl = NHCHCO
               |
               (CH₂)₄NH₂ iso-Aba = iso-aminobutyryl = NH 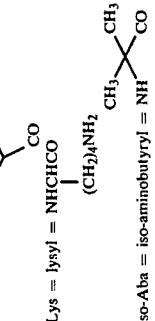

The activities of representative compounds according to the invention are given below in Table II.

TABLE II

| Example No. | IC$_{50}$ ($\mu$M) Human Rheumatoid Synovial Collagenase |
|---|---|
| 5 | 1.7 |
| 6 | 42 |
| 7 | 5.5 |
| 9 | 9.5 |
| 11 | 0.8 |
| 13 | 91 |
| 14 | 1.2 |
| 15 | 3.1 |
| 16 | 4.9 |
| 18 | 1.3 |
| 19 | 51 |
| 21 | 11 |
| 22 | 42 |
| 23 | 25 |
| 24 | 19 |
| 25 | 1.2 |
| 26 | 0.74 |
| 27 | 2.1 |
| 28 | 3.6 |
| 29 | 0.54 |
| 30 | 1.1 |
| 31 | 2.5 |
| 32 | 0.91 |
| 33 | 0.74 |
| 34 | 2.6 |
| 35 | 2.4 |
| 36 | 1.0 |

One of the preferred compounds in accordance with the present invention was tested in vivo to demonstrate the antiarthritic activity thereof in a standardized animal model test and compared against prednisolone which has been shown to be clinically effective in the treatment of rheumatoid arthritis.

The therapeutic effectivness is assessed in the rat model of inflammatory arthritis described by Trentham et al. (1977). In this model, the arthritis, induced by an intradermal injection of Type II collagen, generally develops in both hind paws and the progression and severity of the lesion are monitored by physical measurements of the malleolar width and ankle extensibility.

The compound of Example II in the present specification was administered by intraperitoneal injections at 100 mg/kg twice daily for 21 days commencing seven days after the injection of the disease.

The results of the foregoing test are set forth in Table III below.

TABLE III

The effect of N-[3-N-(benzyloxycarbonyl)amino-1-(R)-carboxypropyl]-L-leucyl-O-methyl-L-tyrosine-N-methylamide (Example 11) on the Physical Parameters of Arthritic Rats' Paws

| PARAMETER | PERCENTAGE CHANGE FROM CONTROL | | | |
|---|---|---|---|---|
| | EXPERIMENT NUMBER | | | MEAN |
| | 1 | 2 | 3 | x |
| MALLEOLAR WIDTH | | | | |
| Example 11 | 65 | 43 | 41 | 50 |
| Prednisolone | 98 | 96 | 97 | 97 |
| ANKLE EXTENSION | | | | |
| Example 11 | 66 | 39 | 39 | 48 |
| Prednisolone | 100 | 96 | 95 | 97 |

Drugs (Example 11 or prednisolone) and vehicle were administered to groups of 10 rats each. Physical measurements on the rat paws were made weekly for four weeks and consisted of (a) the distance between the medial and lateral malleolus (malleolar width) and (b) the ankle extension which was measured by applying a standard force to th rat paw and measuring the angle formed between the flexor surface of the foot and the tibia. Evidence of a therapeutic effect was denoted by a significant reduction in malleolar width and a significant increase in ankle extension. Both measurements were carried out in apparatus designed for the purpose. Area-under-the-curve data from these time course experiments was examinaed by non-parametic statistical analysis. The prednisolone standard was given at a dose of 0.625 mg/kg b.i.d. Prednisolone was chosen as a standard since steroids are known to be effective both clinically in Rheumatoid Arthritis and in animal models of arthritis.

References

Trentham, D. E., Townes, A. S. & Kang, A. H. (1977) "Autoimmunity to Type II Collagen: An Experimental Model of Arthritis" J. Expt. Med. 146. 857–868.

What is claimed is:

1. A compound of the formula:

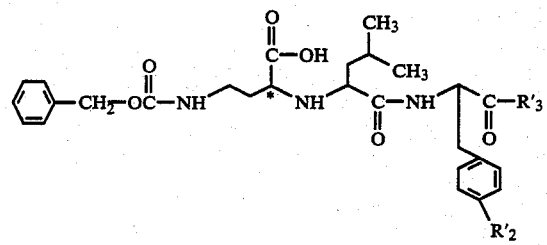

and the pharmaceutically acceptable acid addition salts thereof wherein R'$_2$ represents hydroxy, alkoxy, cycloalkoxy, aralkoxy or substituted alkoxy wherein the substituent is selected from alkylaminocarbonyl or the group

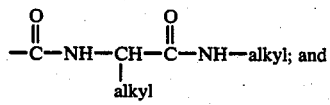

R'$_3$ represents alkylamino or aralkylamino; and the stereochemistry of the carbon atom marked by the asterisk is R or S or a diastereomeric mixture thereof.

2. A compound according to claim 1 wherein R'$_2$ is straight or branched chain alkoxy of from about 1 to 6 carbon atoms.

3. A compound according to claim 2 wherein R'$_2$ is selected from n-propoxy or n-pentoxy.

4. A compound according to claim 1 wherein R'$_3$ is alkylamino.

5. A compound according to claim 4 wherein said alkylamino is methylamino.

6. A compound according to claim 1 wherein the stereochemistry of the carbon atom marked by the asterisk is R.

7. A compound according to claim 1 of the formula.

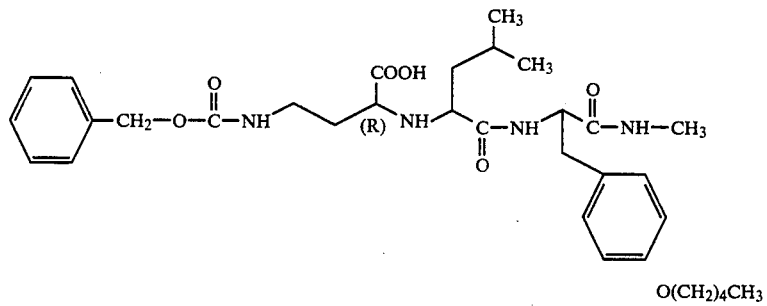

or a pharmaceutically acceptable acid addition salt thereof.

8. A compound according to claim 1 of the formula

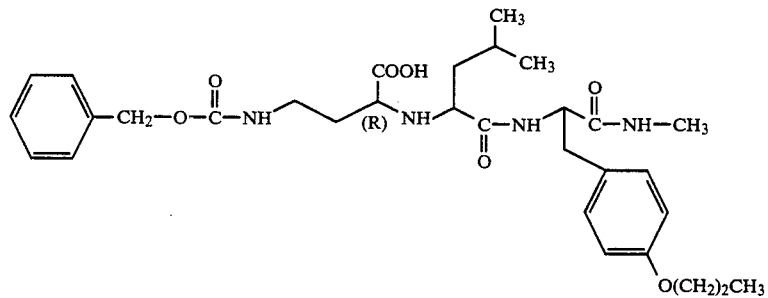

or a pharmaceutically acceptable acid addition salt thereof.

9. A method of promoting an antiarthritic effect in a mammal in need thereof comprising administering thereto a collagenase inhibiting effective amount of a compound according to claim 1.

10. A method according to claim 9 wherein said compound is of the formula:

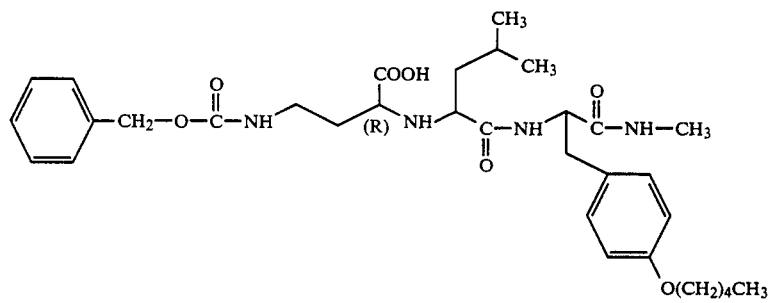

* * * * *